(12) United States Patent
Ling et al.

(10) Patent No.: US 9,465,519 B2
(45) Date of Patent: Oct. 11, 2016

(54) METHODS AND SYSTEMS FOR IN SILICO EXPERIMENTAL DESIGNING AND PERFORMING A BIOLOGICAL WORKFLOW

(71) Applicant: LIFE TECHNOLOGIES CORPORATION, Carlsbad, CA (US)

(72) Inventors: Maurice Ling, Singapore (SG); Kok Hien Gan, Johor Bahru (MY); Kevin Clancy, Oceanside, CA (US); Raymond Tecotzky, Carlsbad, CA (US); Kin Chong Sam, Singapore (SG)

( * ) Notice: Subject to any disclaimer, the term of this patent is extended or adjusted under 35 U.S.C. 154(b) by 226 days.

(21) Appl. No.: 13/724,765

(22) Filed: Dec. 21, 2012

(65) Prior Publication Data

US 2013/0205240 A1 Aug. 8, 2013

Related U.S. Application Data

(60) Provisional application No. 61/578,820, filed on Dec. 21, 2011.

(51) Int. Cl.
*G06F 3/0481* (2013.01)
*G06F 3/0484* (2013.01)
(Continued)

(52) U.S. Cl.
CPC ............ *G06F 3/0484* (2013.01); *G06F 19/28* (2013.01); *G06F 19/26* (2013.01)

(58) Field of Classification Search
CPC .................................................. G06F 3/0481
See application file for complete search history.

(56) References Cited

U.S. PATENT DOCUMENTS 5,334,575 A    8/1994  Noonan et al.
5,434,796 A *  7/1995  Weininger ........... B01J 19/0046
                                                     703/12

(Continued)

FOREIGN PATENT DOCUMENTS

EP         1494156        1/2005
WO       WO96/19497       6/1996

(Continued)

OTHER PUBLICATIONS

Oikawa Marcio Katsumi et al., GenFlow: Generic flow for integration, management and analysis of molecular biology data; Dec. 1, 2004; Brazilian Society of Genetics; vol. 27, No. 4; pp. 691-695.*

(Continued)

*Primary Examiner* — Phenuel Salomon

(74) *Attorney, Agent, or Firm* — Peter G. Foiles; Priya Subrumony

(57) ABSTRACT

Embodiments describe a non-transitory computer-readable storage medium encoded with instructions, executable by a processor, comprising instructions for a method for performing a biological workflow in silico comprising: presenting to a user a plurality of subroutines listed in a sequential order of the workflow, wherein at least two subroutines comprise two steps; providing the user ability to navigate to any subroutine and/or step, to select a subroutine, to view, set, or change one or more parameters associated with step/subroutine; providing option to display biomolecule(s) resulting from execution of the subroutines/steps; and providing an option to navigate to a prior subroutine and change a parameter of a step of the prior subroutine and execute the step of the prior subroutine, if the user is not satisfied with the displayed biomolecule(s). Computer systems and methods for performing a biological workflow in silico are also described.

25 Claims, 31 Drawing Sheets

(51) Int. Cl.
  G06F 19/28 (2011.01)
  G06F 19/26 (2011.01)

(56) References Cited

U.S. PATENT DOCUMENTS

| | | | |
|---|---|---|---|
| 5,766,891 A | 6/1998 | Shuman | |
| 5,851,808 A | 12/1998 | Elledge et al. | |
| 5,888,732 A | 3/1999 | Hartley et al. | |
| 5,888,795 A | 3/1999 | Hamilton | |
| 6,143,557 A | 11/2000 | Hartley et al. | |
| 6,171,861 B1 | 1/2001 | Hartley et al. | |
| 6,219,622 B1* | 4/2001 | Schmidt | C07K 1/00 435/6.11 |
| 6,270,969 B1 | 8/2001 | Hartley et al. | |
| 6,277,608 B1 | 8/2001 | Hartley et al. | |
| 6,505,249 B1* | 1/2003 | Rehkopf | 709/224 |
| 6,509,974 B1* | 1/2003 | Hansen | 358/1.12 |
| 7,024,363 B1* | 4/2006 | Comerford | G10L 15/22 704/270 |
| 7,670,823 B1 | 3/2010 | Hartley et al. | |
| 7,805,252 B2 | 9/2010 | Gustafsson et al. | |
| 7,933,786 B2* | 4/2011 | Wargin | G06Q 10/06 705/4 |
| 8,005,620 B2 | 8/2011 | Gustafsson et al. | |
| 2001/0032108 A1* | 10/2001 | Sieron et al. | 705/7 |
| 2002/0007051 A1 | 1/2002 | Cheo et al. | |
| 2002/0052771 A1* | 5/2002 | Bacon et al. | 705/8 |
| 2002/0068269 A1* | 6/2002 | Allen et al. | 435/4 |
| 2002/0156756 A1* | 10/2002 | Stanley et al. | 706/47 |
| 2002/0178252 A1* | 11/2002 | Balabhadrapatruni et al. | 709/223 |
| 2002/0194154 A1* | 12/2002 | Levy et al. | 707/1 |
| 2003/0044941 A1 | 3/2003 | Crooke | |
| 2004/0259138 A1* | 12/2004 | Klapproth | 435/6 |
| 2005/0004766 A1 | 1/2005 | Ramnarayan et al. | |
| 2005/0021877 A1* | 1/2005 | Varpela et al. | 710/1 |
| 2005/0038776 A1* | 2/2005 | Cyrus et al. | 707/3 |
| 2005/0064484 A1 | 3/2005 | Kasai et al. | |
| 2007/0016377 A1 | 1/2007 | Ho | |
| 2007/0054331 A1 | 3/2007 | Kirnasovsky et al. | |
| 2007/0111256 A1* | 5/2007 | Grobrecht et al. | 435/7.1 |
| 2008/0195570 A1* | 8/2008 | Alsafadi et al. | 706/53 |
| 2008/0294404 A1 | 11/2008 | Zauhar et al. | |
| 2010/0305997 A1* | 12/2010 | Ananian | G06F 9/5038 705/7.27 |
| 2011/0137617 A1* | 6/2011 | Desmet et al. | 703/1 |
| 2014/0180660 A1 | 6/2014 | Clancy et al. | |

FOREIGN PATENT DOCUMENTS

| | | |
|---|---|---|
| WO | WO98/56943 | 12/1998 |
| WO | WO2013/096842 | 6/2013 |
| WO | WO2014/093956 | 6/2014 |

OTHER PUBLICATIONS

Invitrogen, "Vector NTI Advance 11.5®: The Industrial Standard for Sequence Analysis", User Manual, Part No. 1260154, Version 12605019, Jan. 12, 2011, 1-832.

Bonfield et al., "A new DNA sequence assembly program", Nucleic Acids Research, vol. 23, No. 24, 1995, 4992-4999.

Chen et al., "Computational structure-based redesign of enzyme activity", Proceedings of the National Academy of Sciences, vol. 106, No. 10, Mar. 10, 2009, 3764-3769.

Georgiev et al., "OSPREY User Manual Version 1.0", www.cs.duke.edu/donaldlab/sofware/osprey/osprey1.0/OSPREY.pdf, retrieve Mar. 10, 2014, Dec. 31, 2009, 1-77.

Intl Application No. PCT/US2012/071379, International Preliminary Report on Patentability mailed Jun. 24, 2014, 1-7.

Intl Application No. PCT/US2012/071379, International Search Report and Written Opinion mailed Oct. 7, 2013, 1-10.

Intl Application No. PCT/US2013/075217, International Search Report and Written Opinion mailed Mar. 21, 2014, 1-12.

Liu et al., "Rosetta Design server for protein design", Nucleic Acids Research, vol. 34, No. (Web Server Issue), Jul. 1, 2006, W235-W238.

Oikawa et al., "GenFlow: Generic flow for integration, management and analysis of molecular biology data", Genetics and Molecular Biology, vol. 27, No. 4, 2004, 691-695.

Qu et al., "Semantics-Enabled Service Discovery Framework in the SIMDAT Pharma Grid", IEEE Transactions of Information Technology in BioMedicine, vol. 12, No. 2, Mar. 1, 2008, 182-190.

Rieche et al., "A Federated DBMS-Based Integrated Enviroment for Molecular Biology", Scientific and Statistical Database Management, Proceedings, SE Venth Intenrational Working Conference on Charlottesville, VA 28-30, Los Alamitos, CA, IEEE Comput. Soc., Sep. 28, 1994, 118-127.

Suarez et al., "PROTDES: CHARMM toolbox for computational protein design", Systems and Synthetic Biology, vol. 2, Nos. 3-4, Dec. 1, 2008, 105-113.

Tsai et al., "In silico protein design by combinatorial assembly of protein building blocks", Protein Science, vol. 13, No. 10, Oct. 1, 2004, 2753-2765.

Yin et al., "TileSoft: Sequence Optimization Software for Designing DNA Secondary Structures", Department of Computer Science, Duke University, Department of Computer Science, Caltech, Jan. 28, 2004, 1-15.

Zhang et al., "Interactive DNA Sequence and Structure Design for DNA Nanoapplications", IEEE Transactions on Nanobioscience, vol. 3, No. 4, Dec. 2004, 286-292.

Abremski et al., "Bacteriophage P1 Cre-loxP site-specific recombination Site-specific DNA Topoisomerase Activity of the Cre Recombination Protein", The Journal of Biological Chemistry, vol. 261, No. 1, Jan. 5, 1986, 391-396.

Araki et al., "Site-specific Recombinase, R, Encoded by Yeast Plasmid pSR1", Journal of Molecular Biology, vol. 225, No. 1, May 5, 1992, 25-37.

Argos et al., "The integrase family of site-specific recombinases: regional similarities and global diversity", The EMBO Journal, vol. 5, No. 2, 1986, 433-440.

Bisson, et al., "APIC: A Generic Interface for Sequencing Projects", Association for the Advancement of Artificial Intelligence, Proceedings of the Third International Conference of Intelligent Systems for Molecular Biology, 1995, 57-65.

Broach et al., "Recombination within the Yeast Plasmid, 2 mu Circle is Site Specific", Cell, vol. 29, No. 1, May 1982, 227-234.

Campbell, "Chromosomal insertion sites for phages and plasmids", Journal of Bacteriology, vol. 174, No. 23, Dec. 1992, 7495-7499.

Esposito et al., "The integrase family of tyrosine recombinases: evolution of a conserved active site domain", Nucleic Acids Research, vol. 25, No. 18, Sep. 15, 1997, 3605-3614.

Hoess et al., "The Cre-lox Recombination System", Nucleic Acids and Molecular Biology, vol. 4, 1990, 99-109.

Hoess et al., "The role of the loxP spacer region in P1 site-specific recombination", Nucleic Acids Research, vol. 14, No. 5, Mar. 11, 1986, 2287-2300.

Informax, Inc., "Vector NTI Suite Mac OS User's Manual", 2000, 1-416.

Jayaraj et al., "GeMS: an advanced software package for designing synthetic genes", Nucleic Acids Research, vol. 33, No. 9, May 23, 2005, 3011-3016.

Landy, "Dynamic, structural and regulatory aspects of lambda site-specific recombination.", Annual Reviews of Biochemistry, vol. 58, 1989, 913-949.

Landy, "Mechanistic and structural complexity in the site-specific recombination pathways of Int and FLP.", Current Opinion in Genetics and Development, vol. 3, No. 5, Oct. 1993, 699-707.

Maeser et al., "The Gin Recombinase of Phage Mu Can Catalyse Site-Specific Recombination in Plant Protoplasts.", Molecular and General Genetics, vol. 230, No. 1-2, Nov. 1991, 170-176.

Medique et al., "Imagene: an integrated computer environment for sequence annotation and analysis.", Bioinformatics, vol. 15, No. 1, Jan. 1999, 2-15.

(56) References Cited

OTHER PUBLICATIONS

Qian et al., "Reactions between Half-and Full-FLP Recombination Target Sites: A Model System for Analyzing Early Steps in FLP Protein-Mediated Site-Specific Recombination", *The Journal of Biological Chemistry*, vol. 267, No. 1, Apr. 15, 1992, 7794-7805.

Sauer, "Site-specific recombination: developments and applications", *Current Opinion in Biotechnology*, vol. 5, No. 5, Oct. 1994, 521-527.

Sekiguchi et al., "Requirements for noncovalent binding of vaccina topoisomerase I to duplex DNA", *Nucleic Acids Research*, vol. 22, No. 24, Dec. 11, 1994, 5360-5365.

Shuman, "Site-specific interaction of Vaccinia Virus Topoisomerase I with Duplex DNA.Minimal DNA Substrate for Strand Cleavage In Vitro", *Journal of Biological Chemistry*, vol. 266, No. 17, Jun. 15, 1991, 11372-11379.

Voziyanov et al., "A general model for site-specific recombination by the integrase family recombinases", *Nucleic Acids Research*, vol. 27, No. 4, 1999, 930-941.

Kuntz, "Structure-Based Strategies for Drug Design and Discovery", *Science*, vol. 257, No. 5073, Aug. 21, 1992, 1078-1082.

PCT/US2013/075217, International Preliminary Report on Patentability mailed Jun. 25, 2015, 1-9.

\* cited by examiner

FIG. 7L
FIG. 7K
FIG. 7M

Fragments

| Name | Accession | From | To | Length | Form | Description |
|------|-----------|------|-----|--------|------|-------------|
| ADRA1A | ADRA1A | 1 | 2306 | 2306 | Linear | Homo sapiens adrenergic, alpha-1A, r... |
| BRAF | NM_004333 | 1 | 2510 | 2510 | Linear | Homo sapiens v-raf murine sarcoma vi... |

Add

FIG. 8F

```
                        SEQUENCE LISTING

<160> NUMBER OF SEQ ID NOS: 14

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
acaactttgt ataataaagt tgct                                           24

<210> SEQ ID NO 2
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
acaactttgt atagaaaagt tgggtg                                         26

<210> SEQ ID NO 3
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ggggacaagt ttgtaca                                                   17
```

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
taacatttcc aaggccat                                                     18

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
taaccaatgg ctatgggc                                                     18

<210> SEQ ID NO 6
<211> LENGTH: 819
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (1)..(1)
<223> OTHER INFORMATION: a, c, t, g, unknown or other
<220> FEATURE:
<221> NAME/KEY: modified_base
<222> LOCATION: (4)..(39)
<223> OTHER INFORMATION: a, c, t, g, unknown or other
<220> FEATURE:
<221> NAME/KEY: modified_base
<222> LOCATION: (42)..(54)
<223> OTHER INFORMATION: a, c, t, g, unknown or other
<220> FEATURE:
<221> NAME/KEY: modified_base
<222> LOCATION: (65)..(65)
<223> OTHER INFORMATION: a, c, t, g, unknown or other
<220> FEATURE:
<221> NAME/KEY: modified_base
<222> LOCATION: (69)..(69)
<223> OTHER INFORMATION: a, c, t, g, unknown or other
<220> FEATURE:
<221> NAME/KEY: modified_base
<222> LOCATION: (208)..(209)
<223> OTHER INFORMATION: a, c, t, g, unknown or other
<220> FEATURE:
<221> NAME/KEY: modified_base
<222> LOCATION: (422)..(422)
<223> OTHER INFORMATION: a, c, t, g, unknown or other
<220> FEATURE:
<221> NAME/KEY: modified_base
<222> LOCATION: (525)..(525)
<223> OTHER INFORMATION: a, c, t, g, unknown or other
<220> FEATURE:
<221> NAME/KEY: modified_base
<222> LOCATION: (778)..(778)
<223> OTHER INFORMATION: a, c, t, g, unknown or other

<400> SEQUENCE: 6
nacnnnnnnn nnnnnnnnnn nnnnnnnnnn nnnnnnnna gnnnnnnnnn nnnnttcaca        60
ttctncgcng atggttgaga tgtgtataag agacagttag gtgacactat agaatacaag      120
cttgcttgtt cttttttgcag aagctcagaa taaacgctca actttggcag atccgcggcc    180
gcagatctga attccggaga tttgtccnng cagatgctgc tggccttctg ggaatcctgg     240

```
actgtgatta ctgcgctgga gagctgttat ctgtaactgg aagactctcc attaacctgc    300
attaacaata ttgacctgga tttcacagca gtcctataaa aagttgacta gtcacaatga    360
atgtgacgag cttgttctcc ttcaccagcc cagcagtgaa gaggctgctt ggttggaaac    420
anggagacga agaagagaaa tgggcagaga agcagtaga tgccttggtg aaaaagctga    480
agaagaaaaa aggagccatg gaggaactgg aaaaggccct gagantgtcc tggacagccc    540
agtaactgtg tcaccattcc tcgttccttg gatggcaggc tgcaagtgtc acaccgcaag    600
ggcctaccac atgtgattta ttgccgtgtg tggcgttggc cggatctaca aagtcaccat    660
gaactgaaac ccttggagtg ctgcgagtat ccctttggtt ctaaacagaa ggaggtctgc    720
atcaacccgt atcattacaa acgagtggag agtcctgtct tgccacctgt ccttgttnca    780
cggtacagtg agtacaaccc acagcacagt ctccttgcg                           819

<210> SEQ ID NO 7
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
gtggcgggga tcctctagag tcgacctgca ggcatgcaag cttcagg                  47

<210> SEQ ID NO 8
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (32)..(32)
<223> OTHER INFORMATION: a, c, t, g, unknown or other

<400> SEQUENCE: 8
ctgtgctgtg ggttgtactc actgtaccgt gnaacaagga caggtggcaa gacaggactc    60
tccactcg                                                             68

<210> SEQ ID NO 9
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
atgtgtactc ctta                                                      14

<210> SEQ ID NO 10
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ggggacaagt ttgtacaaaa aagcaggct                                      29
```

```
<210> SEQ ID NO 11
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ggggaccact ttgtacaaga aagctgggt                                      29

<210> SEQ ID NO 12
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
actgactaat ataatataca tcatcta                                        27

<210> SEQ ID NO 13
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (44)..(44)
<223> OTHER INFORMATION: a, c, t, g, unknown or other

<400> SEQUENCE: 13
ctgtgctgtg ggttgtactc actgtgcccg tggaacaagg acangtggca agacaggact    60
ctccactcg                                                            69

<210> SEQ ID NO 14
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
ctgtgctgtg ggttgtactc actgtacccg tggaacaagg acaggtggca agacaggact    60
ctccactcgt                                                           70
```

METHODS AND SYSTEMS FOR IN SILICO EXPERIMENTAL DESIGNING AND PERFORMING A BIOLOGICAL WORKFLOW

CROSS REFERENCE TO OTHER APPLICATIONS

This application claims priority to U.S. Provisional Patent Application having Ser. No. 61/578,820, filed Dec. 21, 2011, the entire contents of which are incorporated herein by reference.

SEQUENCE LISTING

The instant application contains a Sequence Listing which has been submitted in ASCII format via EFS-Web and is hereby incorporated by reference in its entirety. Said ASCII copy, created on Apr. 4, 2013, is named LT00642_SL.txt and is 5,806 bytes in size.

FIELD OF THE DISCLOSURE

The present disclosure is directed to bioinformatics, especially to computer systems and computer software relating to methods for in silico designing of and performing biological workflows.

BACKGROUND

Biotechnology research that is important for improving agricultural products, discovering new treatments for diseases, and for identifying and developing new diagnostic methods, relies on complex technologies, methods and experimental design. This research would be greatly facilitated by computer assisted experimental design programs.

SUMMARY OF THE DISCLOSURE

The present disclosure relates, in some embodiments, to a non-transitory computer-readable storage medium encoded with instructions, executable by a processor, the instructions comprising: instructions for providing a method for performing a biological workflow in silico comprising presenting to a user a plurality of subroutines that comprise the biological workflow listed in a sequential order, wherein at least two subroutines of the plurality of subroutines comprise two steps; providing the user ability to navigate to any subroutine of the plurality of sequential subroutines, to select a subroutine and view, set, or change one or more parameters associated with a step of the selected subroutine; providing an option to display to the user, one or more biomolecules resulting from execution of one or more of the plurality of subroutines; and providing an option to the user to navigate to a prior subroutine and change a parameter of a step of the prior subroutine, if the user is not satisfied with the one or more displayed biomolecules.

Non limiting examples of a biological workflow include cloning methods, recombination methods, ligation methods, vector designing methods, methods for synthesis of a nucleic acid, primer design methods, methods for synthesis of a polypeptide, methods for analysis of a cloned molecule, methods of protein analysis, methods for making a modified host.

In some embodiments, instructions on a computer-readable storage medium, according to the present disclosure, can further comprise providing an indication to a user of a current subroutine of the method for performing a biological workflow for the user to review. Indications can also be provided to a user of a current step and/or parameter being selected. In some embodiments, an indication may comprise a highlighted tab in a GUI pane and/or a flashing tab.

In some embodiments, a parameter being viewed, set or changed is a parameter that results from ambiguous user data In some embodiments, one or all parameters that result from ambiguous user data may be highlighted. Non-limiting examples of ambiguous data includes "fuzzy ends" that occur when a DNA sequence cannot be clearly read.

In some embodiments, instructions on a computer-readable storage medium can further comprise receiving at least one selection desired by a user, from the user, for one or more parameters associated with at least one step of the plurality of subroutines of the method for performing a biological workflow; and providing to the user an option for storing in a memory a user defined workflow comprising settings selected by the user for parameters used in the biological workflow.

In some embodiments, instructions on the computer-readable storage medium can further comprise providing to a user or a plurality of users (community of users) the ability to rate or comment on the user defined workflow and storing the rating associated with the user defined workflow in the memory. This can comprise receiving and storing from user(s) at least one comment about the entire user defined workflow, and/or about one or more subroutine(s) in a workflow, and/or about one or more step(s) in a workflow and/or about one or more parameters in a workflow. In some embodiments, instructions on the computer-readable storage medium can further comprise, providing to a user, preset settings for parameters based on user defined workflows with the highest ratings or the most positive comments. In other words a computer readable medium of the present disclosure can learn and suggest to a user the best possible options for a parameter based in highest ratings or positive comments to the parameter in that workflow from other users.

In some embodiments, instructions on the computer-readable storage medium can further comprise providing to a user the ability to save a log of all selected parameters for each step of the user defined method. In some examples this provides an electronic log book or a lab notebook type of recording of all parameters, steps that were user-defined or user selected for a workflow.

In some embodiments, one or more external files (that may be related to the biological workflow) can be uploaded and stored by a user and the computer-readable medium can have instructions for providing additional users the ability to view the external files uploaded.

Parameters viewed, selected, set or changed by a user can comprise default parameters, which are pre-determined parameters stored in the computer-readable storage medium, and/or user input parameter, which are either modified default parameters, parameters input by user, and/or a parameter imported by the user into the computer system. In some embodiments one or more parameters viewed, selected, set or changed by a user comprise a combination of one or more default parameters and one or more user defined parameters.

Providing a user ability to navigate to any subroutine of the plurality of subroutines can be by a graphical user interface (GUI) which can comprise displaying on a first display screen pane all the subroutines of a sequential subroutine comprising the biological workflow and, following selection by the user of any one subroutine, displaying on a second display screen, one or more steps associated with the selected subroutine. Providing the user the ability to navigate to any step of a subroutine can also be accomplished by a graphical user interface (GUI) which comprises displaying on a first display screen pane a subroutine and displaying on a second display screen, one or more steps associated with the selected subroutine.

Selections received from a user of one or more parameters for each step of the plurality of subroutines of the biological workflow can be saved as a selected plurality of steps, which comprise a user-defined method which can be saved and named by a user.

In some embodiments, instructions on the computer-readable storage medium can comprise: a) displaying on a display screen pane a prescribed plurality of subroutines in a sequential order of the biological workflow, wherein the prescribed plurality of subroutines are comprised in a computer readable format; b) navigation by a user using a graphical user interface (GUI) on the display screen of each subroutine of the prescribed plurality of subroutines of the biological workflow; c) selection by the user of one of the subroutines; d) navigation by a user using a GUI on the display screen of each step of a selected subroutine; e) selection by the user of one or more parameters in each step of a selected subroutine to obtain a modified plurality of steps; f) storing the modified plurality of steps by the user, wherein the stored modified plurality of steps comprise the user defined subroutine g) repeating steps b)-f) till all the plurality of sub routines are stored as user defined subroutines; and h) saving and executing the plurality of user defined subroutines to perform a user defined biological workflow.

In some embodiments, navigation by a user of any subroutine or step of the workflow can be in a sequential order of the steps or the subroutine. In some embodiments, navigation by a user of any subroutine or step of the workflow can be in a non-sequential order of the steps or the subroutine.

In some embodiments, a non-transitory computer-readable storage medium encoded with instructions, executable by a processor as described herein can further comprise: executing a user defined workflow comprising executing in silico all the steps of the user defined workflow in sequential order; viewing a first biomolecule obtained by executing the user defined workflow in silico; generation of at least a second user defined workflow, comprising changing the selection of at least one parameter to have a different value relative to the same parameter that was selected in claim 1; executing in silico the at least second user defined workflow to obtain a second biomolecule; viewing the second biotechnology product in silico; and comparing the first biomolecule with the second biomolecule, thereby allowing a user to determine if the first user defined workflow or the second user defined method produces a preferred biomolecule. This can be repeated for several user-defined workflows, till the user finds an optimum biomolecule and/or an optimum workflow to create a desired biomolecule. In some embodiments, users may select a workflow based on a biomolecule that is preferred.

In some embodiments a non-transitory computer-readable storage medium encoded with instructions, executable by a processor, comprises instructions for: providing a pipeline of a method for performing a biological workflow for display to a user, the pipeline of a method comprising a plurality of methods, each method generating at least one biomolecule that may be used in the next method to produce another biomolecule, wherein subroutines of each of the plurality of methods are listed in a sequential order; and executing the pipeline of the method. Additionally, a non-transitory computer readable medium can further comprise providing an option to display to a user, one or more biomolecules resulting from reexecution of the subroutines of the workflow.

In some embodiments, a non-transitory computer readable medium can further comprise providing the ability to input data from a biological instrument wherein the data is used during execution of a subroutine.

The present disclosure, in some embodiments also relates to a computer-implemented method comprising: presenting to a user a plurality of subroutines that comprise the biological workflow listed in a sequential order, wherein at least two subroutines of the plurality of subroutines comprise two steps; providing the user ability to navigate to any subroutine of the plurality of sequential subroutines, to select a subroutine and view, set, or change one or more parameters associated with a step of the selected subroutine; providing an option to display to the user, one or more biomolecules resulting from execution of one or more of the plurality of subroutines; and providing an option to the user to navigate to a prior subroutine and change a parameter of a step of the prior subroutine, if the user is not satisfied with the one or more displayed biomolecules.

In some embodiments, the disclosure describes a system comprising: a processor; and a memory for storing instructions executable by the processor, the instructions comprising instructions for: presenting to a user a plurality of subroutines that comprise the biological workflow listed in a sequential order, wherein at least two subroutines of the plurality of subroutines comprise two steps; providing the user ability to navigate to any subroutine of the plurality of sequential subroutines, to select a subroutine and view, set, or change one or more parameters associated with a step of the selected subroutine; providing an option to display to the user, one or more biomolecules resulting from execution of one or more of the plurality of subroutines; and providing an option to the user to navigate to a prior subroutine and change a parameter of a step of the prior subroutine, if the user is not satisfied with the one or more displayed biomolecules.

BRIEF DESCRIPTION OF THE FIGURES

FIGS. 7A-7O depicts a graphical user interface (GUI) in accordance to one embodiment of a workflow method of the disclosure wherein: FIG. 7A depicts a Gateway® Project GUI; FIG. 7C depicts a Current Task GUI (FIG. 7C discloses SEQ ID NOS 1-2, respectively, in order of appearance); FIG. 7F depicts a Fragments to Amplify GUI; FIG. 7K depicts tools of a GUI for magnifying and zooming; FIG. 7L depicts tools of the GUI to Display a Molecule as linear or circular; FIG. 7M depicts a Create Expression Clones by LR task pane GUI; FIG. 7O depicts GUI pane showing an example Preview Expression Clones task pane showing an example expression clone created.

FIGS. 8A-8H depicts a graphical user interface (GUI) in accordance to one embodiment of a workflow method of the disclosure wherein: FIG. 8A depicts a GUI showing a TOPO® Project screen; FIG. 8B depicts a GUI showing a Task List screen; FIG. 8C depicts a GUI showing a Current Task screen; FIG. 8D depicts a GUI showing a TOPO® Project screen with options for navigating to additional screens such as Saving, Editing and Closing Projects;

FIG. 8E depicts a GUI showing a TOPO® Project screen showing a Projects screen; FIG. 8F depicts a GUI showing a Fragments to Amplify in TOPO® Reaction screen; FIG. 8G depicts a GUI showing a screen when Amplify button is selected (FIG. 8G discloses SEQ ID NOS: 4-5, respectively, in order of appearance); FIG. 8H depicts a GUI showing a screen for Create TOPO® Clones task pane.

FIGS. 9A-9G depicts a graphical user interface (GUI) in accordance to one embodiment of a workflow method of the disclosure wherein: FIG. 9A depicts a GUI showing Launching ContigExpress® screen; FIG. 9B depicts a GUI showing a ContigExpress® Project screen with options for selecting ABI filed from a file system; FIG. 9C depicts a GUI showing a View Fragments panel (FIG. 9C discloses SEQ ID NO: 6); FIG. 9D depicts a GUI showing an example screen for Trim Ends of all Fragments viewing (FIG. 9D discloses SEQ ID NO: 7); FIG. 9E depicts a GUI screen showing a view of specific details of ends trimming by selecting a fragment of interest (FIG. 9E discloses SEQ ID NO: 6); FIG. 9F depicts a screen of Contig assembly parameters; and FIG. 9 G depicts an example screen viewing Resultant Contig (FIG. 9G discloses SEQ ID NOS: 8, 8, 13 and 13-14, respectively, in order of appearance).

Figure 1:
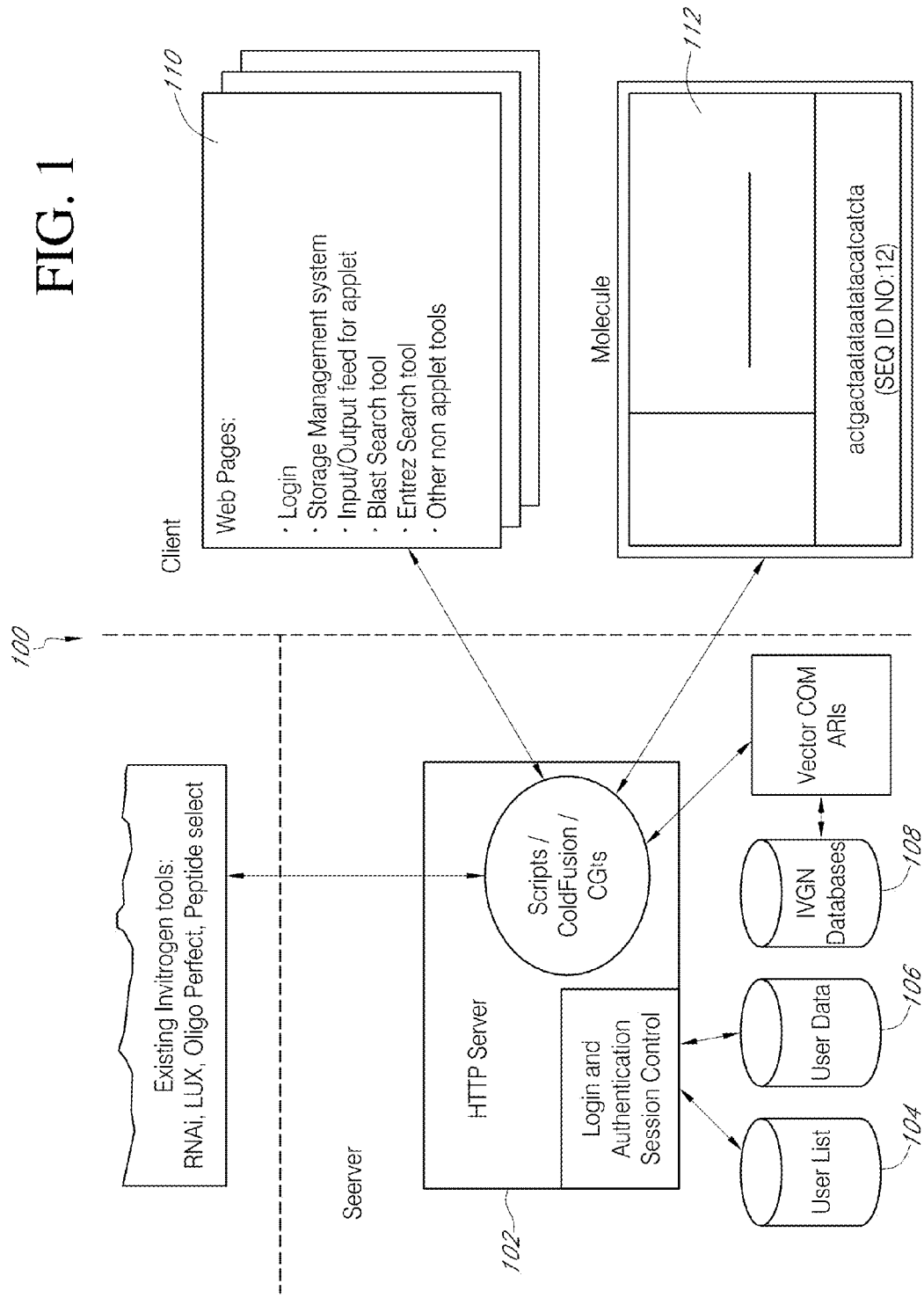
FIG. 1 illustrates a general computer system architecture schematic according to an embodiment of the disclosure.

Additional figures and figure explanations are provided within the illustrative examples provided herein.

DETAILED DESCRIPTION OF THE EMBODIMENTS

In the description that follows, a number of terms used in recombinant nucleic acid technology are utilized extensively. In order to provide a clear and more consistent understanding of the specification and claims, including the scope to be given such terms, the following definitions are provided.

Genomic Products and Services: As used herein, the term genomic products and services refers to products and services that may be used to conduct research involving nucleic acids, including RNA interference (RNAi).

Proteomic Products and Services: As used herein, the term proteomic products and services refers to products and services that may be used to conduct research involving polypeptides.

Clone Collection: As used herein, "clone collection" refers to two or more nucleic acid molecules, each of which comprises one or more nucleic acid sequences of interest.

Customer: As used herein, the term customer refers to any individual, institution, corporation, university, or organization seeking to obtain genomic and proteomic products and services.

Provider: As used herein, the term provider refers to any individual, institution, corporation, university, or organization seeking to provide genomic and proteomic products and services.

Subscriber: As used herein, the term subscriber refers to any customer having an agreement with a provider to obtain public and private genomic and proteomic products and services at subscriber rates.

Non-subscriber: As used herein, the term non-subscriber refers to any customer who does not have an agreement with a provider to obtain public and private genomic and proteomic products and services at subscriber rates.

Host: As used herein, the term "host" refers to any prokaryotic or eukaryotic (e.g., mammalian, insect, yeast, plant, avian, animal, etc.) cell and/or organism that is a recipient of a replicable expression vector, cloning-vector or any nucleic acid molecule. The nucleic acid molecule may contain, but is not limited to, a sequence of interest, a transcriptional regulatory sequence (such as a promoter, enhancer, repressor, and the like) and/or an origin of replication. As used herein, the terms "host," "host cell," "recombinant host" and "recombinant host cell" may be used interchangeably. For examples of such hosts, see Sambrook, et al., Molecular Cloning: A Laboratory Manual, Cold Spring Harbor Laboratory, Cold Spring Harbor, N.Y.

Transcriptional Regulatory Sequence: As used herein, the phrase "transcriptional regulatory sequence" refers to a functional stretch of nucleotides contained on a nucleic acid molecule, in any configuration or geometry, that act to regulate the transcription of (1) one or more nucleic acid sequences that may comprise ORFs, (e.g., two, three, four, five, seven, ten, etc.) into messenger RNA or (2) one or more nucleic acid sequences into untranslated RNA. Examples of transcriptional regulatory sequences include, but are not limited to, promoters, enhancers, repressors, operators (e.g., the tet operator), and the like.

Promoter: As used herein, a promoter is an example of a transcriptional regulatory sequence, and is specifically a nucleic acid generally described as the 5'-region of a gene located proximal to the start codon or nucleic acid that encodes untranslated RNA. The transcription of an adjacent nucleic acid segment is initiated at or near the promoter. A repressible promoter's rate of transcription decreases in response to a repressing agent. An inducible promoter's rate of transcription increases in response to an inducing agent. A constitutive promoter's rate of transcription is not specifically regulated, though it can vary under the influence of general metabolic conditions.

Insert: As used herein, the term "insert" refers to a desired nucleic acid segment that is a part of a larger nucleic acid molecule. In many instances, the insert will be introduced into the larger nucleic acid molecule using techniques known to those of skill in the art, e.g., recombinational cloning, topoisomerase cloning or joining, ligation, etc.

Target Nucleic Acid Molecule: As used herein, the phrase "target nucleic acid molecule" refers to a nucleic acid molecule comprising at least one nucleic acid sequence of interest, preferably a nucleic acid molecule that is to be acted upon using the compounds and methods of the present disclosure. Such target nucleic acid molecules may contain one or more (e.g., two, three, four, five, seven, ten, twelve, fifteen, twenty, thirty, fifty, etc.) sequences of interest.

Recognition Sequence: As used herein, the phrase "recognition sequence" or "recognition site" refers to a particular sequence to which a protein, chemical compound, DNA, or RNA molecule (e.g., restriction endonuclease, a topoisomerase, a modification methylase, a recombinase, etc.) recognizes and binds. In the present disclosure, a recognition sequence may refer to a recombination site. For example, the recognition sequence for Cre recombinase is loxP which is a 34 base pair sequence comprising two 13 base pair inverted repeats (serving as the recombinase binding sites) flanking an 8 base pair core sequence (see FIG. 1 of Sauer, B., Current Opinion in Biotechnology 5:521-527 (1994)). Other examples of recognition sequences are the attB, attP, attL, and attR sequences, which are recognized by the recombinase enzyme X Integrase attB is an approximately 25 base pair sequence containing two 9 base pair core-type Int binding sites and a 7 base pair overlap region. attP is an approximately 240 base pair sequence containing core-type Int binding sites and arm-type Int binding sites as well as sites for auxiliary proteins integration host factor (IHF), FIS and excisionase (Xis) (see Landy, Current Opinion in Biotechnology 3:699-707 (1993)). Such sites may also be engineered according to the present disclosure to enhance production of products, such as biomolecules, in the methods of the disclosure. For example, when such engineered sites lack the P1 or H1 domains to make the recombination reactions irreversible (e.g., attR or attP), such sites may be designated attR' or attP' to show that the domains of these sites have been modified in some way.

Recombination Proteins: As used herein, the phrase "recombination proteins" includes excisive or integrative proteins, enzymes, co-factors or associated proteins that are involved in recombination reactions involving one or more recombination sites (e.g., two, three, four, five, seven, ten, twelve, fifteen, twenty, thirty, fifty, etc.), which may be wild-type proteins (see Landy, Current Opinion in Biotechnology 3:699-707 (1993)), or mutants, derivatives (e.g., fusion proteins containing the recombination protein sequences or fragments thereof), fragments, and variants thereof. Examples of recombination proteins include Cre, Int, IHF, X is, Flp, F is, Hin, Gin, .PHI.C31, Cin, Tn3 resolvase, TndX, XerC, XerD, TnpX, Hjc, Gin, SpCCE1, and ParA.

Recombinases: As used herein, the term "recombinases" is used to refer to the protein that catalyzes strand cleavage and re-ligation in a recombination reaction. Site-specific recombinases are proteins that are present in many organisms (e.g., viruses and bacteria) and have been characterized as having both endonuclease and ligase properties. These recombinases (along with associated proteins in some cases) recognize specific sequences of bases in a nucleic acid molecule and exchange the nucleic acid segments flanking those sequences. The recombinases and associated proteins are collectively referred to as "recombination proteins" (see, e.g., Landy, A., Current Opinion in Biotechnology 3:699-707 (1993)).

Numerous recombination systems from various organisms have been described. See, e.g., Hoess, et al., Nucleic Acids Research 14(6):2287 (1986); Abremski, et al., J. Biol. Chem. 261(1):391 (1986); Campbell, J. Bacteriol. 174(23): 7495 (1992); Qian, et al., J. Biol. Chem. 267(11):7794 (1992); Araki, et al., J. Mol. Biol. 225(1):25 (1992); Maeser and Kahnmann, Mol. Gen. Genet. 230:170-176 (1991); Esposito, et al., Nucl. Acids Res. 25(18):3605 (1997). Many of these belong to the integrase family of recombinases (Argos, et al., EMBO J. 5:433-440 (1986); Voziyanov, et al., Nucl. Acids Res. 27:930 (1999)). Perhaps the best studied of these are the Integrase/att system from bacteriophage .lamda. (Landy, A. Current Opinions in Genetics and Devel. 3:699-707 (1993)), the Cre/loxP system from bacteriophage P1 (Hoess and Abremski (1990) In Nucleic Acids and Molecular Biology, vol. 4. Eds.: Eckstein and Lilley, Berlin-Heidelberg: Springer-Verlag; pp. 90-109), and the FLP/FRT system from the *Saccharomyces cerevisiae* 2μcircle plasmid (Broach, et al., Cell 29:227-234 (1982)).

Recombination Site: A used herein, the phrase "recombination site" refers to a recognition sequence on a nucleic acid molecule that participates in an integration/recombination reaction by recombination proteins. Recombination sites are discrete sections or segments of nucleic acid on the participating nucleic acid molecules that are recognized and bound by a site-specific recombination protein during the initial stages of integration or recombination. For example, the recombination site for Cre recombinase is loxP, which is a 34 base pair sequence comprised of two 13 base pair inverted repeats (serving as the recombinase binding sites) flanking an 8 base pair core sequence (see FIG. 1 of Sauer, B., Curr. Opin. Biotech. 5:521-527 (1994)). Other examples of recombination sites include the attB, attP, attL, and attR sequences described in U.S. provisional patent applications 60/136,744, filed May 28, 1999, and 60/188,000, filed Mar. 9, 2000, and in co-pending U.S. patent application Ser. Nos. 09/517,466 and 09/732,91-all of which are specifically incorporated herein by reference—and mutants, fragments, variants and derivatives thereof, which are recognized by the recombination protein .lamda. Int and by the auxiliary proteins integration host factor (IHF), FIS and excisionase (Xis) (see Landy, Curr. Opin. Biotech. 3:699-707 (1993)).

Mutating specific residues in the core region of the att site can generate a large number of different att sites. As with the att I and att2 sites utilized in GATEWAY™, each additional mutation potentially creates a novel att site with unique specificity that will recombine only with its cognate partner att site bearing the same mutation and will not cross-react with any other mutant or wild-type att site. Novel mutated att sites (e.g., attB 1-10, attP 1-10, attR 1-10 and attL 1-10) are described in previous patent application Ser. No. 09/517, 466, filed Mar. 2, 2000, which is specifically incorporated herein by reference. Other recombination sites having unique specificity (i.e., a first site will recombine with its corresponding site and will not recombine or not substantially recombine with a second site having a different specificity) may be used to practice the present disclosure. Examples of suitable recombination sites include, but are not limited to, loxP sites; loxP site mutants, variants or derivatives such as loxP511 (see U.S. Pat. No. 5,851,808); frt sites; frt site mutants, variants or derivatives; dif sites; dif site mutants, variants or derivatives; psi sites; psi site mutants, variants or derivatives; cer sites; and cer site mutants, variants or derivatives.

Recombination sites may be added to molecules by any number of known methods. For example, recombination sites can be added to nucleic acid molecules by blunt end ligation, PCR performed with fully or partially random primers, or inserting the nucleic acid molecules into a vector using a restriction site flanked by recombination sites.

Recombinational Cloning: As used herein, the phrase "recombinational cloning" refers to a method whereby segments of nucleic acid molecules or populations of such molecules are exchanged, inserted, replaced, substituted or modified, in vitro or in vivo. Preferably, such cloning method is an in vitro method.

Suitable recombinational cloning systems that utilize recombination at defined recombination sites have been previously described in U.S. Pat. Nos. 5,888,732, 6,143,557, 6,171,861, 6,270,969, and 6,277,608, and in pending U.S. application Ser. No. 09/517,466, and in published United States application no. 20020007051, (each of which is fully incorporated herein by reference), all assigned to the Invitrogen Corporation, Carlsbad, Calif. In brief, the GATEWAY™ Cloning System described in these patents utilizes vectors that contain at least one recombination site to clone desired nucleic acid molecules in vivo or in vitro. In some embodiments, the system utilizes vectors that contain at least two different site-specific recombination sites that may be based on the bacteriophage lambda system (e.g., att1and att2) that are mutated from the wild-type (att0) sites. Each mutated site has a unique specificity for its cognate partner att site (i.e., its binding partner recombination site) of the same type (for example attB1 with attP1, or attL1 with attR1) and will not cross-react with recombination sites of the other mutant type or with the wild-type att0 site. Different site specificities allow directional cloning or linkage of desired molecules thus providing desired orientation of the cloned molecules. Nucleic acid fragments flanked by recombination sites are cloned and subcloned using the GATEWAY™ system by replacing a selectable marker (for example, ccdB) flanked by att sites on the recipient plasmid molecule, sometimes termed the Destination Vector. Desired clones are then selected by transformation of a ccdB sensitive host strain and positive selection for a marker on the recipient molecule. Similar strategies for negative selection (e.g., use of toxic genes) can be used in other organisms such as thymidine kinase (TK) in mammals and insects.

Topoisomerase recognition site: As used herein, the term "topoisomerase recognition site" means a defined nucleotide sequence that is recognized and bound by a site specific topoisomerase. For example, the nucleotide sequence 5'-(C/T)CCTT-3' is a topoisomerase recognition site that is bound specifically by most poxvirus topoisomerases, including vaccinia virus DNA topoisomerase I, which then can cleave the strand after the 3'-most thymidine of the recognition site to produce a nucleotide sequence comprising 5'-(C/T)CCTT-PO.sub.4-TOPO, i.e., a complex of the topoisomerase covalently bound to the 3' phosphate through a tyrosine residue in the topoisomerase (see, Shuman, J. Biol. Chem. 266: 11372-11379, 1991; Sekiguchi and Shuman, Nucl. Acids Res. 22:5360-5365, 1994; each of which is incorporated herein by reference; see, also, U.S. Pat. No. 5,766,891; PCT/US95/16099; and PCT/US98/12372). In comparison, the nucleotide sequence 5'-GCAACTT-3' is the topoisomerase recognition site for type IA $E.$ $coli$ topoisomerase III.

Repression Cassette: As used herein, the phrase "repression cassette" refers to a nucleic acid segment that contains a repressor or a selectable marker present in the subcloning vector.

Selectable Marker: As used herein, the phrase "selectable marker" refers to a nucleic acid segment that allows one to select for or against a molecule (e.g., a replicon) or a cell that contains it, often under particular conditions. These markers can encode an activity, such as, but not limited to, production of RNA, peptide, or protein, or can provide a binding site for RNA, peptides, proteins, inorganic and organic compounds or compositions and the like. Examples of selectable markers include but are not limited to: (1) nucleic acid segments that encode products that provide resistance against otherwise toxic compounds (e.g., antibiotics); (2) nucleic acid segments that encode products that are otherwise lacking in the recipient cell (e.g., tRNA genes, auxotrophic markers); (3) nucleic acid segments that encode products that suppress the activity of a gene product; (4) nucleic acid segments that encode products that can be readily identified (e.g., phenotypic markers such as (beta-galactosidase, green fluorescent protein (GFP), yellow fluorescent protein (YFP), red fluorescent protein (RFP), cyan fluorescent protein (CFP), and cell surface proteins); (5) nucleic acid segments that bind products that are otherwise detrimental to cell survival and/or function; (6) nucleic acid segments that otherwise inhibit the activity of any of the nucleic acid segments described in Nos. 1-5 above (e.g., antisense oligonucleotides); (7) nucleic acid segments that bind products that modify a substrate (e.g., restriction endonucleases); (8) nucleic acid segments that can be used to isolate or identify a desired molecule (e.g., specific protein binding sites); (9) nucleic acid segments that encode a specific nucleotide sequence that can be otherwise non-functional (e.g., for PCR amplification of subpopulations of molecules); (10) nucleic acid segments that, when absent, directly or indirectly confer resistance or sensitivity to particular compounds; and/or (11) nucleic acid segments that encode products that either are toxic (e.g., Diphtheria toxin) or convert a relatively non-toxic compound to a toxic compound (e.g., Herpes simplex thymidine kinase, cytosine deaminase) in recipient cells; (12) nucleic acid segments that inhibit replication, partition or heritability of nucleic acid molecules that contain them; and/or (13) nucleic acid segments that encode conditional replication functions, e.g., replication in certain hosts or host cell strains or under certain environmental conditions (e.g., temperature, nutritional conditions, etc.).

Site-Specific Recombinase: As used herein, the phrase "site-specific recombinase" refers to a type of recombinase that typically has at least the following four activities (or combinations thereof): (1) recognition of specific nucleic acid sequences; (2) cleavage of said sequence or sequences; (3) topoisomerase activity involved in strand exchange; and (4) ligase activity to reseal the cleaved strands of nucleic acid (see Sauer, B., Current Opinions in Biotechnology 5:521-527 (1994)). Conservative site-specific recombination is distinguished from homologous recombination and transposition by a high degree of sequence specificity for both partners. The strand exchange mechanism involves the cleavage and rejoining of specific nucleic acid sequences in the absence of DNA synthesis (Landy, A. (1989) Ann. Rev. Biochem. 58:913-949).

Suppressor tRNAs: As used herein, the phrase "suppressor tRNA" refers to a molecule that mediates the incorporation of an amino acid in a polypeptide in a position corresponding to a stop codon in the mRNA being translated.

Homologous Recombination: As used herein, the phrase "homologous recombination" refers to the process in which nucleic acid molecules with similar nucleotide sequences associate and exchange nucleotide strands. A nucleotide sequence of a first nucleic acid molecule that is effective for engaging in homologous recombination at a predefined position of a second nucleic acid molecule will therefore have a nucleotide sequence that facilitates the exchange of nucleotide strands between the first nucleic acid molecule and a defined position of the second nucleic acid molecule. Thus, the first nucleic acid will generally have a nucleotide sequence that is sufficiently complementary to a portion of the second nucleic acid molecule to promote nucleotide base pairing.

Homologous recombination: requires homologous sequences in the two recombining partner nucleic acids but does not require any specific sequences. As indicated above, site-specific recombination that occurs, for example, at recombination sites such as att sites, is not considered to be "homologous recombination," as the phrase is used herein.

Vector: As used herein, the term "vector" refers to a nucleic acid molecule (preferably DNA) that provides a useful biological or biochemical property to an insert. Examples include plasmids, phages, viruses, autonomously replicating sequences (ARS), centromeres, and other sequences that are able to replicate or be replicated in vitro or in a host cell, or to convey a desired nucleic acid segment to a desired location within a host cell. A vector can have one or more restriction endonuclease recognition sites (e.g., two, three, four, five, seven, ten, etc.) at which the sequences can be cut in a determinable fashion without loss of an essential biological function of the vector, and into which a nucleic acid fragment can be spliced in order to bring about its replication and cloning. Vectors can further provide primer sites (e.g., for PCR), transcriptional and/or translational initiation and/or regulation sites, recombinational signals, replicons, selectable markers, etc. Clearly, methods of inserting a desired nucleic acid fragment that do not require the use of recombination, transpositions or restriction enzymes (such as, but not limited to, uracil N-glycosylase (UDG) cloning of PCR fragments (U.S. Pat. Nos. 5,334,575 and 5,888,795, both of which are entirely incorporated herein by reference), T:A cloning, and the like) can also be applied to clone a fragment into a cloning vector to be used according to the present disclosure. The cloning vector can further contain one or more selectable markers (e.g., two, three, four, five, seven, ten, etc.) suitable for use in the identification of cells transformed with the cloning vector.

Subcloning Vector: As used herein, the phrase "subcloning vector" refers to a cloning vector comprising a circular or linear nucleic acid molecule that includes, preferably, an appropriate replicon. In the present disclosure, the subcloning vector can also contain functional and/or regulatory elements that are desired to be incorporated into the final product to act upon or with the cloned nucleic acid insert. The subcloning vector can also contain a selectable marker (preferably DNA).

Primer: As used herein, the term "primer" refers to a single stranded or double stranded oligonucleotide that is extended by covalent bonding of nucleotide monomers during amplification or polymerization of a nucleic acid molecule (e.g., a DNA molecule). In one aspect, the primer may be a sequencing primer (for example, a universal sequencing primer). In another aspect, the primer may comprise a recombination site or portion thereof.

Adapter: As used herein, the term "adapter" refers to an oligonucleotide or nucleic acid fragment or segment (preferably DNA) that comprises one or more recombination sites (or portions of such recombination sites) that can be added to a circular or linear nucleic acid molecule as well as to other nucleic acid molecules described herein. When using portions of recombination sites, the missing portion may be provided by the nucleic acid molecule. Such adapters may be added at any location within a circular or linear molecule, although the adapters are preferably added at or near one or both termini of a linear molecule. Preferably, adapters are positioned to be located on both sides (flanking) a particular nucleic acid molecule of interest. In accordance with the disclosure, adapters may be added to nucleic acid molecules of interest by standard recombinant techniques (e.g., restriction digest and ligation). For example, adapters may be added to a circular molecule by first digesting the molecule with an appropriate restriction enzyme, adding the adapter at the cleavage site and reforming the circular molecule that contains the adapter(s) at the site of cleavage. In other aspects, adapters may be added by homologous recombination, by integration of RNA molecules, and the like. Alternatively, adapters may be ligated directly to one or more and preferably both termini of a linear molecule thereby resulting in linear molecule(s) having adapters at one or both termini. In one aspect of the disclosure, adapters may be added to a population of linear molecules, (e.g., a cDNA library or genomic DNA that has been cleaved or digested) to form a population of linear molecules containing adapters at one and preferably both termini of all or substantial portion of said population.

Adapter-Primer: As used herein, the phrase "adapter-primer" refers to a primer molecule that comprises one or more recombination sites (or portions of such recombination sites) that can be added to a circular or to a linear nucleic acid molecule described herein. When using portions of recombination sites, the missing portion may be provided by a nucleic acid molecule (e.g., an adapter) of the disclosure. Such adapter-primers may be added at any location within a circular or linear molecule, although the adapter-primers are preferably added at or near one or both termini of a linear molecule. Such adapter-primers may be used to add one or more recombination sites or portions thereof to circular or linear nucleic acid molecules in a variety of contexts and by a variety of techniques, including but not limited to amplification (e.g., PCR), ligation (e.g., enzymatic or chemical/synthetic ligation), recombination (e.g., homologous or non-homologous (illegitimate) recombination) and the like.

Template: As used herein, the term "template" refers to a double stranded or single stranded nucleic acid molecule, all or a portion of which is to be amplified, synthesized, reverse transcribed, or sequenced. In the case of a double-stranded DNA molecule, denaturation of its strands to form a first and a second strand is preferably performed before these molecules may be amplified, synthesized or sequenced, or the double stranded molecule may be used directly as a template. For single stranded templates, a primer complementary to at least a portion of the template hybridizes under appropriate conditions and one or more polypeptides having polymerase activity (e.g., two, three, four, five, or seven DNA polymerases and/or reverse transcriptases) may then synthesize a molecule complementary to all or a portion of the template. Alternatively, for double stranded templates, one or more transcriptional regulatory sequences (e.g., two, three, four, five, seven or more promoters) may be used in combination with one or more polymerases to make nucleic acid molecules complementary to all or a portion of the template. The newly synthesized molecule, according to the disclosure, may be of equal or shorter length compared to the original template. Mismatch incorporation or strand slippage during the synthesis or extension of the newly synthesized molecule may result in one or a number of mismatched base pairs. Thus, the synthesized molecule need not be exactly complementary to the template. Additionally, a population of nucleic acid templates may be used during synthesis or amplification to produce a population of nucleic acid molecules typically representative of the original template population.

Incorporating: As used herein, the term "incorporating" means becoming a part of a nucleic acid (e.g., DNA) molecule or primer.

Library: As used herein, the term "library" refers to a collection of nucleic acid molecules (circular or linear). In one embodiment, a library may comprise a plurality of nucleic acid molecules (e.g., two, three, four, five, seven, ten, twelve, fifteen, twenty, thirty, fifty, one hundred, two hundred, five hundred one thousand, five thousand, or more), that may or may not be from a common source organism, organ, tissue, or cell. In another embodiment, a library is representative of all or a: portion or a significant portion of the nucleic acid content of an organism (a "genomic" library), or a set of nucleic acid molecules representative of all or a portion or a significant portion of the expressed nucleic acid molecules (a cDNA library or segments derived therefrom) in a cell, tissue, organ or organism. A library may also comprise nucleic acid molecules having random sequences made by de novo synthesis, mutagenesis of one or more nucleic acid molecules, and the like. Such libraries may or may not be contained in one or more vectors (e.g., two, three, four, five, seven, ten, twelve, fifteen, twenty, thirty, fifty, etc.). In some embodiments, a library may be "normalized" library (i.e., a library of cloned nucleic acid molecules from which each member nucleic acid molecule can be isolated with approximately equivalent probability).

Normalized: As used herein, the term "normalized" or "normalized library" means a nucleic acid library that has been manipulated, preferably using the methods of the disclosure, to reduce the relative variation in abundance among member nucleic acid molecules in the library to a range of no greater than about 25-fold, no greater than about 20-fold, no greater than about 15-fold, no greater than about 10-fold, no greater than about 7-fold, no greater than about 6-fold, no greater than about 5-fold, no greater than about 4-fold, no greater than about 3-fold or no greater than about 2-fold.

Amplification: As used herein, the term "amplification" refers to any in vitro method for increasing the number of copies of a nucleic acid molecule with the use of one or more polypeptides having polymerase activity (e.g., one, two, three, four or more nucleic acid polymerases or reverse transcriptases). Nucleic acid amplification results in the incorporation of nucleotides into a DNA and/or RNA molecule or primer thereby forming a new nucleic acid molecule complementary to a template. The formed nucleic acid molecule and its template can be used as templates to synthesize additional nucleic acid molecules. As used herein, one amplification reaction may consist of many rounds of nucleic acid replication. DNA amplification reactions include, for example, polymerase chain reaction (PCR). One PCR reaction may consist of 5 to 100 cycles of denaturation and synthesis of a DNA molecule.

Nucleotide: As used herein, the term "nucleotide" refers to a base-sugar-phosphate combination. Nucleotides are monomeric units of a nucleic acid molecule (DNA and RNA). The term nucleotide includes ribonucleoside triphosphates ATP, UTP, CTG, GTP and deoxyribonucleoside triphosphates such as dATP, dCTP, dITP, dUTP, dGTP, dTTP, or derivatives thereof. Such derivatives include, for example, [.alpha.-S]dATP, 7-deaza-dGTP and 7-deaza-dATP. The term nucleotide as used herein also refers to dideoxyribonucleoside triphosphates (ddNTPs) and their derivatives. Illustrated examples of dideoxyribonucleoside triphosphates include, but are not limited to, ddATP, ddCTP, ddGTP, ddITP, and ddTTP. According to the present disclosure, a "nucleotide" may be unlabeled or detectably labeled by well known techniques. Detectable labels include, for example, radioactive isotopes, fluorescent labels, chemiluminescent labels, bioluminescent labels and enzyme labels.

Nucleic Acid Molecule: As used herein, the phrase "nucleic acid molecule" refers to a sequence of contiguous nucleotides (riboNTPs, dNTPs, ddNTPs, or combinations thereof) of any length. A nucleic acid molecule may encode a full-length polypeptide or a fragment of any length thereof, or may be non-coding. As used herein, the terms "nucleic acid molecule" and "polynucleotide" may be used interchangeably and include both RNA and DNA.

Oligonucleotide: As used herein, the term "oligonucleotide" refers to a synthetic or natural molecule comprising a covalently linked sequence of nucleotides that are joined by a phosphodiester bond between the 3' position of the pentose of one nucleotide and the 5' position of the pentose of the adjacent nucleotide. \

Open Reading Frame (ORF): As used herein, an open reading frame or ORF refers to a sequence of nucleotides that codes for a contiguous sequence of amino acids. ORFs of the disclosure may be constructed to code for the amino acids of a polypeptide of interest from the N-termius of the polypeptide (typically a methionine encoded by a sequence that is transcribed as AUG) to the C-terminus of the polypeptide. ORFs of the disclosure include sequences that encode a contiguous sequence of amino acids with no intervening sequences (e.g., an ORF from a cDNA) as well as ORFs that comprise one or more intervening sequences (e.g., introns) that may be processed from an mRNA containing them (e.g., by splicing) when an mRNA containing the ORF is transcribed in a suitable host cell. ORFs of the disclosure also comprise splice variants of ORFs containing intervening sequences.

ORFs may optionally be provided with one or more sequences that function as stop codons (e.g., contain nucleotides that are transcribed as UAG, an amber stop codon, UGA, an opal stop codon, and/or UAA, an ochre stop codon). When present, a stop codon may be provided after the codon encoding the C-terminus of a polypeptide of interest (e.g., after the last amino acid of the polypeptide) and/or may be located within the coding sequence of the polypeptide of interest. When located after the C-terminus of the polypeptide of interest, a stop codon may be immediately adjacent to the codon encoding the last amino acid of the polypeptide or there may be one or more codons (e.g., one, two, three, four, five, ten, twenty, etc) between the codon encoding the last amino acid of the polypeptide of interest and the stop codon. A nucleic acid molecule containing an ORF may be provided with a stop codon upstream of the initiation codon (e.g., an AUG codon) of the ORF. When located upstream of the initiation codon of the polypeptide of interest, a stop codon may be immediately adjacent to the initiation codon or there may be one or more codons (e.g., one, two, three, four, five, ten, twenty, etc) between the initiation codon and the stop codon.

Polypeptide: As used herein, the term "polypeptide" refers to a sequence of contiguous amino acids of any length. The terms "peptide," "oligopeptide," or "protein" may be used interchangeably herein with the term "polypeptide."

Hybridization: As used herein, the terms "hybridization" and "hybridizing" refer to base pairing of two complementary single-stranded nucleic acid molecules (RNA and/or DNA) to give a double stranded molecule. As used herein, two nucleic acid molecules may hybridize, although the base pairing is not completely complementary. Accordingly, mismatched bases do not prevent hybridization of two nucleic acid molecules provided that appropriate conditions, well known in the art, are used. In some aspects, hybridization is said to be under "stringent conditions." By "stringent conditions," as the phrase is used herein, is meant overnight incubation at 42.degree. C. in a solution comprising: 50% formamide, 5.times.SSC (750 mM NaCl, 75 mM trisodium citrate), 50 mM sodium phosphate (pH 7.6), 5.times. Denhardt's solution, 10% dextran sulfate, and 20.mu.g/ml denatured, sheared salmon sperm DNA, followed by washing the filters in 0.1.times.SSC at about 65.degree. C.

Feature: As used herein, the term "feature" refers to a segment of a biomolecule that provides a specific function. For example, a "feature" can be a region of a polypeptide or polynucleotide that has a specific function. In an illustrative example, a feature is a region of a vector that has a specific function. For example, a feature on a vector includes, but is not limited to, a restriction enzyme site, a recombination site, or a tag-encoding sequence.

An exemplary list of vectors that can be used in the in silico design methods, includes the following: BaculoDirect Linear DIMA; BacuiloDirect Linear; DNA Cloning Fragment DNA; BaculoDirect N-term Linear DNA_verA; BaculoDirect™ C-Term Baculovirus Linear DNA; BaculoDirect™ N-Term Baculovirus Linear DNA; Champion™ pET100/D-TOPO®; Champion™ pET 101/D-TOPO®; Champion™ pET 102/D-TOPO®; Champion™ pET 104/D-TOPO®; Champion™ pET104-DEST; Champion™ pET151/D-TOPO.COPYRGT.; Champion™ pET 160/D-TOPO®; Champion™ pET 160-DEST; Champion™ pET 161-DEST; Champion™ pET200/D-TOPO®; pAc5.1/V5-His A, B, and C; pAd/BLOCK-iT-DEST; pAd/BLOCK-f!."-DEST_verA_sz; pAd/CMVA/5 DEST; pAd/PL-DEST; pAO815; pBAD/g111 A, B, and C; pBAD/H is A, B, and C; pBAD/myc-His A, B, and C; pBAD/Thio-TOPO®; pBAD 102/D-TOPO®; pBAD20/D-TOPO®; pBAD202/D-TOPO®; pBAD DEST49; PBAD-TOPO; PBAD-TOPO®; pBC1; pBLOCK-fT3-DEST pBLOCK-iT6-DEST pBlueBac4.5 pBlueBac4.5A/5-His TOPO®; pBlueBacHis2 A, B, and C; pBR322; pBudCE4.1; pcDN3.1A/5-His-TOPO; pcDNA3.1(−); pcDNA3.1(+); pcDNA3.1(+)/myc-HisA; pcDNA3.1(+)/myc-His A, B, C; pcDNA3.1(+)/myc-His B; pcDNA3.1(+)/myc-HisC; DcDNA3.1/CT-GFP-TOPO; pcDNA3.1/His A; pcDNA3.1/His B; pcDNA3.1/His C; pcDNA3.1/Hygro(−); pcDNA3.1/Hygro(+); pcDNA3.1/NT-GFP-TOPO; pcDNA3.1/nV5-DEST; pcDNA3.1A/5-His A; pcDNA3.1A/5-His B; pcDNA3.1A/5-His C; pcDNA3.1/Zeo(−); pcDNA3.1/Zeo(+); pcDNA3.1/Zeo(+); pcDNA3.1DA/5-His-TOPO; pcDNA3.2N5-DEST; pcDNA3.2A/5-GW/D-TOPO; pcDNA3.2-DEST; pcDNA4/His A; pcDNA4/His B; pcDNA4/His C; pcDNA4/HisMAX A, B & C; pcDNA4/HisMax-TOPO; pcDNA4/HisMax-TOPO; pcDNA4/myc-His A, B, and C; pcDNA4/TO; pcDNA4/TO; pcDNA4/TO/myc-His A; pcDNA4/TO/myc-His A, B, C; pcDNA4/TO/myc-His B; pcDNA4/TO/myc-His C; pcDNA4N5-His A, B, and C; pcDNAS/FRT; pcDNAS/FRT; pcDNA5/FRT/TO/CAT; pcDNA5/FRT/TO-TOPO; pcDNA5/FRT/V5-His-TOPO; pcDNA5/TO; pcDNA6.2/cGeneBLAzer-DEST_verA_sz; pcDNA6 2/cGeneBLAzer-GW/D-TOPO pcDNA6; 2/cGeneBlazer-GW/D-TOPO_verA_sz pcDNA6.2/cLumio-DEST; pcDNA6 2/cLumio-DE STverAsz pcDNA6.2/GFP-DEST_verA_sz; pcDNA6.2/nGeneBLAzer-DEST pcDNA6 2/nGeneBLAzer-DEST_verA_sz pcDMA6 2/nGeneBlazer-GW/D-TOPO_verA_s2 pcDNA6.2/nLumio-DEST; pcDNA6 2/nLumio-DEST_verB_sz; pcDNA6.2A/5-DEST pcDNA6.2A/5-GW/D-TOPO pcDNA6/BioEase-DEST verAsz; pcDNA6/H62His A, B, and C pcDNA6/His A, B, and C; pcDNA6/TR; pcDNA6/V5-His A; pcDNA6/V5-His B; pcDNA6/V5-His C; pcDNA6/V5-His C; pcDNA-DEST40; pcDNA-DEST47; pcDNA-DEST53; pCEP4; pCEP4/CAT; pCMV/myc/cyto; pCMV/myc/ER; pCMV/myc/mito; pCMV/myc/nuc; pCMVSPORT6 NotI-SalI Cut; pCoBlasi; pCR Blunt; pCR XL TOPO; pCR® T7/CT TOPO®; pCR® T7/NT TOPO®; pCR2.1-TOPO; pCR3.1; pCR3.1-Uni; pCR4BLUNT-TOPO; pCR4-TOPO; pCR8/GW/TOPO TA; pCR8/GW-TOPO_verA_sz; pCR-Blunt II-TOPO; -pCRII-TOPO; pDEST™ R4-R3; PDEST™10; PDEST™14; PDEST™15; pDEST™17; pDEST™20; pDEST™22; PDEST™24; pDEST™26; pDES™27; pDEST™32; pDEST™8; pDEST™ 38; pDEST™39; pDisplay; pDONR™ P2R P3; PDONR™ P2R-P3; pDONR™ P4-P1R; pDONR™ P4-P1R; pDONR™/Zeo; pDONR™/Zeo; pDONR™201; pDONR™201; pDONR™207; pDONR™207; pDONR™221; pDONR™221; pDONR™222; pDONR™222; pEF/myc/cyto; pEF/myc/mito; pEF/myc/nuc; pEFi/His A, B, and C; pEF1/myc-His A, B, and C; pEF1/V5-HisA, B, and C; pEF4/myc-His A, B, and C; pEF4N5-His A, B, and C; pEFS/FRT V5 D-TOPO; pEF5/FRT/V5-DEST™; pEF6/His A, B, and C; pEF6/myc-His A, B, and C; pEF6/V5-His A, B, and C; pEF6A/5-His-TOPO; pEF-DEST51; pENTR U6_verA_sz; pENTR/Hir-TO_verA_sz; pENTR-TEV/D-TOPO; pENTR™/D-TOPO; pENTR™/D-TOPO; pENTR™/SD/D-TOPO; pENTR™/SD/D-TOPO; pENTR™/TEV/D-TOPO; pENTR™11; pENTR™1A; pENTR™2B; pENTR™3C; pENTR™4; pET SUMO_verA_sz; pET104.1-DEST_verA_sz; pET104-DEST; pET 160/GW/D-TOPO_verA sz pET160-DEST_verA_sz; pET161 D-TOPO; pET 161/G W/D-TOPO_verA_sz; pET161-DEST_verA_sz; pEXPi-DEST pEXP2-DEST pEXP3-DEST; pEXP3-DEST_vefA_sz; pEXP-AD502 pFastBac Dual pFastBad pFastBacHTA pFastBacHT B pFaslBacHT C; pFLDa; pFliTrx; pFRT/lacZeo; pFRT/lacZeo, pOG44, pcDNAS/FRT; pFRT/lacZeo2; pGAPZ A, B, and C; pGAPZa A, B. and C; pGene/V5-His A, B, and C; pGeneBLAzer-TOPO; pGeneBLAzer-TOPOverA sz; pGlow-TOPO; pH)1_-D2; pH1L-S1; pHybLex/Zeo; pHyBLex/Zeo-MS2; pIB/His A, B, and C; pIBA/5-His Topo; pIBA/5-His-DEST; p1BA/5-His-TOPO; p1ZA/5-His; p!ZT/V5-His; pl_en!i4 BLOCK-iT-DEST; pLenti4/BLOCK-iT-DEST; pLenti4/TOA/5-DEST; pLenti4/TOA/5-DEST_verA sz; pLenti4A/5-DEST; pLen114."/5-DEST verA_sz; pLenti6/BLOCK-tT-DEST; pl_entiS/BLOCK-iT-DEST_verA_sz; pLenti6/UbCA/5-DEST; pLenti6/UbC/vSDEST_verA_sz; pLenli6A/5-DEST; pLen!i6A/5-D-TOPO; plex; pMelBac A, B, and C; pMET A, B, and C; pMETa A, B, C; pMIBA/5-His A, B, and C; pMIBA/5-His/CAT; pMT/BioEase-DESTverAsz; pMT/BioEase™-DEST; pMT/BioEase™-DEST; pMT/BiPA/5-His A, B, and C; pMT/V5-His A, B, and C; pMT/V5-His-TOPO; pMT-DEST™ 48; pNMT; pNMT1-TOPO; pNMT41-TOPO; pNMT81-TOPO; pOG44; pPIC3.5K; pPIC6 A, B, and C; pPIC6a A, B, and C; pPICZ A; pPICZ B; pPICZ C; pPICZalpha A; pPICZalpha B; pPICZalpha C; pREP4; pRH3'; pRH5.sup.f; pRSET; pSCRE EN-iT/lacZ-DEST_verA_sz; pSecTag/FRTA/5-His TOPO; pSecTag2 A, B, and C; pSecTag2/Hygro A, B, and C; pSH18-34; pThio-His A, B, and C; pTracer-CMV/Bsd; pTracer-CMV2; pTracer-EF A, B, and C; pTracer-EF/Bsd A, B, and C; pTracer-SV40; pTrcHis A, B. and C; pTrcHis2 A, B, and C; pTrcHis2-TOPO®; pTrcHis2-TOPO®; pTrcHis-TOPO®; pT-Rex-DEST30; pT-Rex-DEST30; pT-Rex-DEST™ 31; pT-REx™-DEST31; pUB/BSD TOPO; pUB6A/5-His A, B, and C; pUC18; pUC19; pUni/V5 His TOPO; pVAX1; pVP22/myc-His TOPO®; pVP22/myc-His2 TOPO®;

pYC2.1-E; pYC2/CT; pYC2/Nt A, B. C; pYC2-E; pYC6/CT; pYD1; pYES2; pYES2.1A/5-His-TOPO; pYES2/CT; pYES2/NT; pYES2/NT A, B, & C; pYES3/CT; pYES6/CT; pYES-DEST™ 52; pYESTrp; pYESTrp2; pYESTrp3; pZeoSV2(−); pZeoSV2(+); pZErO-1; pZErO-2.

Other terms used in the fields of recombinant nucleic acid technology and molecular and cell biology as used herein will be generally understood by one of ordinary skill in the applicable arts.

The present invention, in some embodiments, provides prescribed in silico workflows that empower a user with an easy way to navigate through various subroutines within complex workflows and to view, set, or change parameters within those subroutines. In certain embodiments, for example, all of the subroutines that are used in a workflow are provided to a user within one workspace, which is a separately viewable area on a computer screen. A subroutine within a workflow is a discrete task that can be conveniently completed by a user and provides a convenient stopping point in a workflow, typically in the laboratory implementation of an in silico workflow. For example, where a nucleic acid is amplified during a workflow, an amplification reaction is a subroutine in certain exemplary embodiments of such workflow. The prescribed workflows of the present invention provide a roadmap for a user to help them easily visualize and navigate through the various discrete tasks that are involved in completion of a workflow.

The term "subroutine" as described above and used herein is intended to describe a part of a complex biological/biotechnology workflow, (i.e., a discrete task that can be conveniently completed by a user and provides a convenient stopping point in a workflow, typically in the laboratory implementation of an in silico workflow), and may comprise a series of steps of one or more sub-process of the subroutine. A plurality of subroutines that complete a biological process, which may be performed/executed in a sequential order, make up a biological/biotechnology workflow. The subroutines of an in silico workflow of the present invention, are typically laboratory subroutines, especially biological laboratory subroutines, that is subroutines that are useful for, and sometimes have a direct counterpart in, a biological workflow, such as a biological workflow performed in a biological research laboratory. Accordingly, the term subroutine as used in this specification is different in meaning from the typical software code definition of subroutine.

In an illustrative non-limiting example, a biological workflow can be a cloning workflow, such as TOPO® Cloning, which comprises at least three subroutines exemplified by: "1. Amplify fragments to use in TOPO® reaction;" "2. Create TOPO® clones;" and "3. Preview clones." Each of these three subroutines further comprise one or more steps, for example, the subroutine "1. Amplify fragments to use in TOPO reaction" comprises one or more steps (also referred to as tasks) such as, "1) to select the fragment(s) a user want to amplify by PCR for use in a TOPO cloning reaction; 2) optionally to change the regions to amplify in the selected molecules; 3) load/select PCR settings for the amplification such as Tm, % GC of primer; primer length; type of nucleotide to be amplified (DNA/RNA); etc)." Each step (or task) allows a user to select/set one or more parameters associated with that step, for example in the illustrative example to TOPO Cloning workflow, in the subroutine of "1. Amplify fragments to use in TOPO reaction" and in the step (task) of "1. To select the fragment(s) a user wants to amplify" an example parameter may be "selecting a fragment from a list of fragments provided by the software; or typing in or importing in a fragment known to user that the user desires to amplify. This exemplary cloning workflow and other biotech workflows comprising one or more subroutines, each subroutine comprising one or more steps or tasks, and each step comprising selecting/inputting one or more parameters are described in further detail in other parts of the disclosure (see also FIGS. 3-9).

Exemplary software and/or computer program products of the disclosure may be used to perform a biological workflow in silico. Embodiments also relate to in silico design of a method to produce one or more biomolecules, chemical molecules, or commercial biological products, such as biotechnology products (design of a biological workflow). In silico workflows of the disclosure may be used to make or produce one or more biomolecules, chemical molecules, or commercial biological products such as biotechnology products using one or more computer program products including data collections of the disclosure such as but not limited to clone collections and individual clones; vectors; hosts/modified hosts (for example having modified/designed vectors) to make certain biomolecules and/or biological products or have certain biological properties; polypeptides, such as enzymes, antibodies, hormones; nucleic acids such as various types of RNA, DNA, primers, probes; libraries (e.g., cDNA libraries, genomic libraries, etc.); buffers, growth media, purification systems, cell lines, chemical compounds, fluorescent labels, functional assays, and variety of kits including DNA and protein purification, amplification and modification. These exemplary biomolecules, chemical molecules, and/or commercial products are provided for example only and are not intended to limit the present invention.

Those skilled in the art will recognize that the operations of one or more embodiments of this disclosure may be implemented using hardware, software, firmware, or combinations thereof, as appropriate. For example, some processes can be carried out using processors or other digital circuitry under the control of software, firmware, or hardwired logic. The term "logic" herein refers to fixed hardware, programmable logic and/or an appropriate combination thereof, as would be recognized by one skilled in the art to carry out a recited function(s). Software and firmware can be stored on computer-readable media. Some other processes can be implemented using analog circuitry, as is well known to one of ordinary skill in the art. Additionally, memory or other storage, as well as communication components, may be employed in embodiments of the disclosure.

FIG. 1 illustrates an example of a computing system and client/server environments, database servers, and networks and their interconnections. FIG. 1 provides an exemplary client/server system 100 showing the general architecture for performing methods provided herein. The general architecture includes server functions, including design of biomolecules such as RNAi, and other scripts which are run on a server computer 102 and that can access databases on the server (104, 106, and 108), and web pages 110 that are delivered to the client. Server computer 102 may be connected to the internet via an internet service provider (ISP). Similarly, client computers may be connected to the internet via an ISP connection. Client/server system 100 may include a user list database 104 for storing users of the system. In some embodiments, users may need to login to the system to access information. Client/server system 100 may also include user data database 106 that may include data stored associated with the plurality of users of the system. For example, a customized workflow file may be stored in the user data database 106. Further, client/server system 100 may include a company database 106 and/or a public access database 106 (such as GenBank that a user may use to obtain data from) or a commercial database 106 including databases stored on a cloud that may include product information that a user may use to produce a biomolecule, chemical, and/or commercial product such as a biotechnology product. Further, client/server system 100 may include a company database 108 that may include product information that a user may use to produce a biomolecule, chemical, and/or commercial product such as a biotechnology product. A company may update available products periodically to remove products that may not be available anymore or add new products, for example. Furthermore, other predetermined workflow files may be uploaded to company database 108 to be downloaded or provided to users. Typically, the server computer is maintained by a provider of biological products and of the computer products provided herein, and the client computer is a computer of the customer. In various embodiments, there is a plurality of client computers in communication with server 102. Client computers may display user interfaces such as webpages 110 or molecule viewers 112 according to various embodiments described herein, for example.

In some embodiments, server 102 or another server in communication with client computers may store user data such that a user may download data, including workflows, from the server. Furthermore, a user may store data that may be accessed by other users of the client/server system 100. For example, according to some embodiments described herein, a prescribed workflow may be shared with another user or a group of users.

As mentioned above, according to various embodiments, user data may be stored in the user data database 106. User data may include user feedback on a workflow or a biomolecule, chemical molecule, and/or commercial product that results from carrying out a workflow of the invention, for example. In various embodiments, the user data may be further analyzed to generate personalized recommendations for a user, such as commonly used parameters by the user or offer recommendations of commercial products the user may want to purchase. The aggregate of user data may further be analyzed, according to various embodiments, to generate statistics on prescribed workflows or biomolecules, chemical molecules, and/or commercial products that result from carrying out a workflow of the invention.

In another aspect of the invention, a documented Application Programming Interface (API) is provided to a customer that is associated with an in silico design method, an in silico workflow method, and a computer program product. API further can provide product ordering options to a customer such that a customer can route orders through that customer's computer system, such as a business-to-business system.

Figure 2:
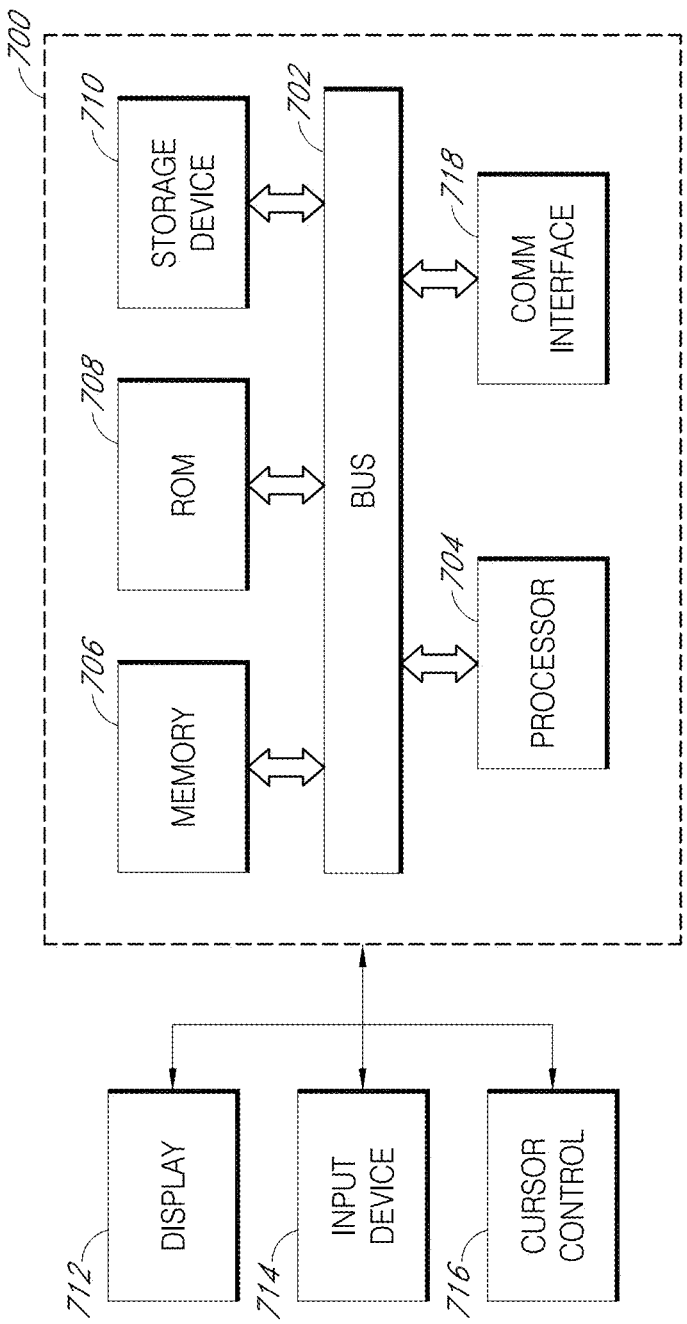
FIG. 2 is a block diagram that illustrates a computer system 700 that may be employed to carry out processing functionality, according to some exemplary embodiments of the disclosure.

FIG. 2 is a block diagram that illustrates a computer system 700 that may be employed to carry out processing functionality, according to various embodiments. Computing system 700 can include one or more processors, such as a processor 704. Processor 704 can be implemented using a general or special purpose processing engine such as, for example, a microprocessor, controller or other control logic. In this example, processor 704 is connected to a bus 702 or other communication medium.

Further, it should be appreciated that a computing system 700 of FIG. 2 may be embodied in any of a number of forms, such as a rack-mounted computer, mainframe, supercomputer, server, client, a desktop computer, a laptop computer, a tablet computer, hand-held computing device (e.g., PDA, cell phone, smart phone, palmtop, etc.), cluster grid, netbook, embedded systems, or any other type of special or general purpose computing device as may be desirable or appropriate for a given application or environment. Additionally, a computing system 700 can include a conventional network system including a client/server environment and one or more database servers, or integration with LIS/LIMS infrastructure. A number of conventional network systems, including a local area network (LAN) or a wide area network (WAN), and including wireless and/or wired components, are known in the art. Additionally, client/server environments, database servers, and networks as illustrated in the example in FIG. 1 are well documented in the art.

Computing system 700 may include bus 702 or other communication mechanism for communicating information, and processor 704 coupled with bus 702 for processing information.

Computing system 700 also includes a memory 706, which can be a random access memory (RAM) or other dynamic memory, coupled to bus 702 for storing instructions to be executed by processor 704. Memory 706 also may be used for storing temporary variables or other intermediate information during execution of instructions to be executed by processor 704. Computing system 700 further includes a read only memory (ROM) 708 or other static storage device coupled to bus 702 for storing static information and instructions for processor 704.

Computing system 700 may also include a storage device 710, such as a magnetic disk, optical disk, or solid state drive (SSD) is provided and coupled to bus 702 for storing information and instructions. Storage device 710 may include a media drive and a removable storage interface. A media drive may include a drive or other mechanism to support fixed or removable storage media, such as a hard disk drive, a floppy disk drive, a magnetic tape drive, an optical disk drive, a CD or DVD drive (R or RW), flash drive, or other removable or fixed media drive. As these examples illustrate, the storage media may include a computer-readable storage medium having stored therein particular computer software, instructions, or data.

In alternative embodiments, storage device 710 may include other similar instrumentalities for allowing computer programs or other instructions or data to be loaded into computing system 700. Such instrumentalities may include, for example, a removable storage unit and an interface, such as a program cartridge and cartridge interface, a removable memory (for example, a flash memory or other removable memory module) and memory slot, and other removable storage units and interfaces that allow software and data to be transferred from the storage device 710 to computing system 700.

Computing system 700 can also include a communications interface 718. Communications interface 718 can be used to allow software and data to be transferred between computing system 700 and external devices. Examples of communications interface 718 can include a modem, a network interface (such as an Ethernet or other NIC card), a communications port (such as for example, a USB port, a RS-232C serial port), a PCMCIA slot and card, Bluetooth, etc. Software and data transferred via communications interface 718 are in the form of signals which can be electronic, electromagnetic, optical or other signals capable of being received by communications interface 718. These signals may be transmitted and received by communications interface 718 via a channel such as a wireless medium, wire or cable, fiber optics, or other communications medium. Some examples of a channel include a phone line, a cellular phone link, an RF link, a network interface, a local or wide area network, and other communications channels.

Computing system 700 may be coupled via bus 702 to a display 712, such as a cathode ray tube (CRT) or liquid crystal display (LCD), for displaying information to a computer user. An input device 714, including alphanumeric and other keys, is coupled to bus 702 for communicating information and command selections to processor 704, for example. An input device may also be a display, such as an LCD display, configured with touchscreen input capabilities. Another type of user input device is cursor control 716, such as a mouse, a trackball or cursor direction keys for communicating direction information and command selections to processor 704 and for controlling cursor movement on display 712. This input device typically has two degrees of freedom in two axes, a first axis (e.g., x) and a second axis (e.g., y), that allows the device to specify positions in a plane. A computing system 700 provides data processing and provides a level of confidence for such data. Consistent with certain implementations of embodiments of the present teachings, data processing and confidence values are provided by computing system 700 in response to processor 704 executing one or more sequences of one or more instructions contained in memory 706. Such instructions may be read into memory 706 from another computer-readable medium, such as storage device 710. Execution of the sequences of instructions contained in memory 706 causes processor 704 to perform the process states described herein. Alternatively hard-wired circuitry may be used in place of or in combination with software instructions to implement embodiments of the present teachings. Thus implementations of embodiments of the present teachings are not limited to any specific combination of hardware circuitry and software.

The term "computer-readable medium" and "computer program product" as used herein generally refers to any media that is involved in providing one or more sequences or one or more instructions to processor 704 for execution. Such instructions, generally referred to as "computer program code" (which may be grouped in the form of computer programs or other groupings), when executed, enable the computing system 700 to perform features or functions of embodiments of the present disclosure. These and other forms of computer-readable media may take many forms, including but not limited to, non-volatile media, volatile media, and transmission media. Non-volatile media includes, for example, solid state, optical or magnetic disks, such as storage device 710. Volatile media includes dynamic memory, such as memory 706. Transmission media includes coaxial cables, copper wire, and fiber optics, including the wires that comprise bus 702.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, PROM, and EPROM, a FLASH-EPROM, any other memory chip or cartridge, a carrier wave as described hereinafter, or any other medium from which a computer can read.

Various forms of computer readable media may be involved in carrying one or more sequences of one or more instructions to processor 704 for execution. For example, the instructions may initially be carried on magnetic disk of a remote computer. The remote computer can load the instructions into its dynamic memory and send the instructions over a telephone line using a modem. A modem local to computing system 700 can receive the data on the telephone line and use an infra-red transmitter to convert the data to an infra-red signal. An infra-red detector coupled to bus 702 can receive the data carried in the infra-red signal and place the data on bus 702. Bus 702 carries the data to memory 706, from which processor 704 retrieves and executes the instructions. The instructions received by memory 706 may optionally be stored on storage device 710 either before or after execution by processor 704. In some embodiments wireless internet connectivity can be used to access and receive data from by remote computer.

Figure 10:
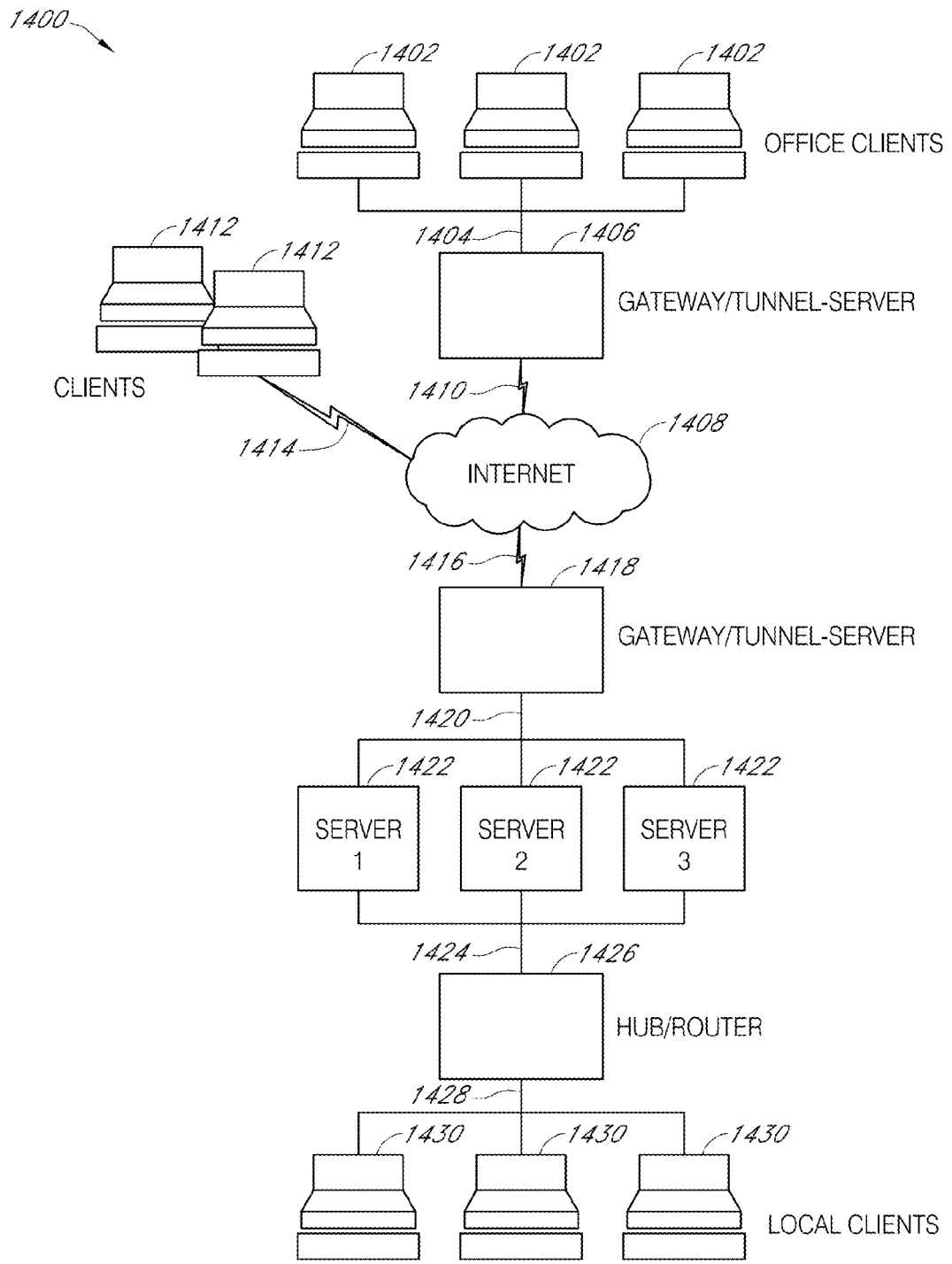
FIG. 10 shows an illustration of a typical internet network configuration where a number of client machines, possibly in a remote local office, are shown connected to a gateway/hub/tunnel-server/etc.

FIG. 10 is a block diagram that illustrates a typical Internet network configuration wherein a number of client machines 1402 possibly in a remote local office, are shown connected to a gateway/hub/tunnel-server/etc. 1410 which is itself connected to the internet 1408 via some internet service provider (ISP) connection 1410. Also shown are other possible clients 1412 similarly connected to the internet 1408 via an ISP connection 1414, with these units communicating to possibly a central lab or office, for example, via an ISP connection 1416 to a gateway/tunnel-server 1418 which is connected 1420 to various enterprise application servers 1422 which could be connected through another hub/router 1426 to various local clients 1430. Any of these servers 1422 could function as a development server for the analysis of potential content management and delivery design solutions as described in the present disclosure, as more fully described below.

It will be appreciated that, for clarity purposes, the above description has described embodiments of the disclosure with reference to different functional units and processors. However, it will be apparent that any suitable distribution of functionality between different functional units, processors or domains may be used without detracting from various embodiments of this disclosure. For example, functionality illustrated to be performed by separate processors or controllers may be performed by the same processor or controller. Hence, references to specific functional units are only to be seen as references to suitable means for providing the described functionality, rather than indicative of a strict logical or physical structure or organization.

In some embodiments of the present disclosure, in silico methods are described that may be performed (executed), by a user, to obtain a biotechnology product comprising one or more steps (e.g., a workflow or in some embodiments multiple workflows to obtain a pipeline of workflows) that may be accessible and controllable by the user via a Graphical User Interface (GUI) that is visible on Display 712. A user may enter data (e.g external data) and/or select options provided in the GUI using Input Device 714 and/or Cursor Control 716. In some embodiments, components of computer system 700 convert input data provided by a user into a computer readable format to one or more computer system components (such as a memory, a database, a processor etc.) to enable interpretation of input data received from a user and to initiate controller instructions to conduct one or more steps of the in silico method.

In some embodiments, user input data may also be used for report generation of the particular in silico method being performed. In some embodiments, components of computer system 700, such as Display 712, may also receive data from one or more processors/sensors/detectors following performing one or more steps of an in silico method that are then converted into a user understood format to enable a user to monitor progress of the workflow steps and/or to obtain additional input from a user to determine the next course/step of the workflow in the in silico method. Input of data from a user or translation of data received from various devices within computer system 700 may be mediated by components of a software (or computer program) of the disclosure (not expressly depicted in FIG. 6) which comprises comprising a computer readable medium comprising computer readable instructions, which, when executed by the computer system, are configured to display on Display 712 (screen, LCD).

A software (or computer program) of the disclosure may be operable to receive user instructions, either in the form of user input into a set parameter fields, e.g., in a GUI, or in the form of pre-programmed instructions such as but not limited to pre-programmed instructions for performing a variety of different specific operations and/or for analyzing various parameters and/or for analyzing one or more data components. A software of the disclosure, in some embodiments, may be operable to convert pre-programmed instructions to appropriate computer language for instructing operation of system 700 to carry out a desired operation. A software of the disclosure, in some embodiments, may be operable to convert data signals or parameters received into appropriate computer language that may then be analyzed by a processor in computer and/or converted into user viewable format for a user to review or analyze.

In some embodiments, a software of the disclosure may comprise functional specifications as well as graphical user interface (GUI) specifications. GUI specifications enable user mediated methods. Exemplary GUI's of the present disclosure may comprise some general GUI specifications. In some embodiments, general GUI specifications may comprise all screens, with the exception of pop-up screens, being 800 pixels wide and 480 pixels high.

Other general GUI specifications may include without limitation, the availability of a Home button in all menu screens where Home button allows a user to navigate to a Main Menu; the availability of Breadcrumbs or a Breadcrumb Trail in all menu screens (breadcrumbs may be abbreviated when they are too long for display); the availability of Time and Date in all menu screens; the availability of a Back button in all menu screens where a Back button allows a user to navigate to a previous screen; the availability of a Save button in screens where a user can change and save one or more fields. Breadcrumbs refer to a navigation aid used in a user interface to show the path that a user has taken to arrive at a screen.

In some embodiments, in a screen where a Save button is available, a Back button may allow a user to either save or cancel a change, if any, before navigating to previous screen. In some embodiments, in a screen where a Save button is available, a Home button allows a user to either save or cancel a change, if any, before navigating to a Home screen. General GUI specifications also include the availability of a Keypad in screens where a user needs to enter an alphanumeric string or special character keys. Some examples of GUI's of the disclosure are described later in this application.

Exemplary software and/or computer program products of the invention can be used to perform in silico design of a method to produce one or more biomolecules, chemical molecules, or biotechnology products (design of a biological workflow). In silico designing to make or produce one or more biomolecules, chemical molecules, or biotechnology products using one or more computer program products of the invention can include production of biomolecules, chemical molecules, or biotechnology products such as but not limited to clone collections and individual clones; vectors; hosts/modified hosts (for example having modified/designed vectors) to make certain biomolecules, chemical molecules, or biotechnology products or have certain biological properties; polypeptides, such as enzymes, antibodies, hormones; nucleic acids such as various types of RNA, DNA, primers, probes; libraries (e.g., cDNA libraries, genomic libraries, etc.); buffers, growth media, purification systems, cell lines, chemical compounds, fluorescent labels, functional assays, and variety of kits including DNA and protein purification, amplification and modification. Further, these exemplary products are provided for example only and are not intended to limit the present invention.

One or more methods of the disclosure can be performed in silico using a computer system comprising a non-transitory computer readable storage medium encoded with instructions, comprising computer readable instructions (such as a computer program), which, are executable by a processor of the computer system. In some embodiments, instructions of a computer readable storage medium of the disclosure may comprise instructions to display on a display screen series of steps that may be performed to obtain a biotechnology product. In some embodiments, the displayed series of steps comprise all the steps that must be performed by a user to obtain a biotechnology product and may be referred to in some embodiments as "prescribed steps" or a "prescribed workflow" or "a subroutine of a biological workflow." A series of "prescribed steps" or "subroutines" may be displayed on a GUI navigation panel (or display pane) where selecting a subroutine (button on GUI) highlights it and takes a user to another navigation panel or GUI screen (or display pane) which provides a list of steps (tasks) that comprise the selected subroutine. Each individual subroutine of a biological workflow generally further comprise a series of steps (sub-steps or tasks) each of which may be executed independently to obtain intermediate products of the biotechnology product. Accordingly, in some embodiments, instructions of a computer readable storage medium of the disclosure may comprise instructions to display on a display screen (such as a second display screen or a second display pane), steps (tasks or sub-steps) of the "subroutine" or "prescribed step" selected by a user using a GUI button in a first display screen or display pane.

Using a GUI a user may customize one or more of these steps (tasks or substeps) by providing user inputs. In some embodiments, user inputs may comprise customized inputs that may be user designed (generated by a user, imported by a user or modified from default parameters by a user). In some embodiments, user inputs may be selected from a set of default inputs that are comprised/stored in the computer program (for example a database having default alternative parameters/values that may be available for the user to select (for example, in the form of a drop down menu)).

In silico methods of the disclosure, in some embodiments, may comprise a user navigating through "prescribed steps" or "subroutines" in a sequential fashion (navigation in ordered steps). In other embodiments, a user may navigate through "prescribed steps" or "subroutines" in no particular sequence and may even go back and forth to input data into various steps out of order (navigation in random steps) prior to performing (executing) the entire prescribed step series.

In some embodiments, a computer-readable storage medium encoded with instructions, executable by a processor, the instructions comprising instructions for: 1) executing individual steps of a "prescribed series of steps" (also called "subroutine"); and 2) instructions for viewing intermediate products obtained by one or more of the steps of the "prescribed steps" thereby allowing a user to view an intermediate biotechnology product and determine if the method step(s) need to be modified to arrive at a final biotechnology product.

Accordingly, the present disclosure provides a user with a tool to review progress of intermediate steps of a biotechnology process by viewing intermediate biotechnology products and providing the ability to change one or more conditions, parameters and/or criteria associated with that intermediate step by inputting/selecting another parameter and/or criteria if the intermediate biotechnology product was not found to be satisfactory or optimum, thereby allowing the user to design a better method for making the final biotechnology product. In some embodiments, a user may be able to determine what parameters to input into a prescribed method based on ability to review the outcome (intermediate product and/or final product) in silico.

A user may conveniently navigate a GUI of prescribed steps in any random or ordered fashion and input a parameter (such as by determining what parameter to input for the best possible outcome as described above). Once a user has made selections and/or input parameters for all steps of a prescribed method, the entire method may be executed in silico and the final product may be viewed.

In some embodiments of the disclosure, a computer-readable storage medium encoded with instructions, executable by a processor, may comprise instructions for: 3) storing each user selected/input parameter associated with each step/sub-step of a biotech method in a memory and 4) instructions for allowing a user to retrieve the stored parameters. Accordingly a user may store and retrieve a log of one or more user-defined method (user defined workflow) comprising information that was input/selected by a user, in the form of a electronic lab note book, thereby accurately capturing all changes made/all parameters input by user in a method. This allows for accurate reproduction and tracking of changes made to a workflow for obtaining a biotechnology product. In some embodiments, a user-defined method (user defined workflow) that is stored may be then converted into user viewable format for display, and/or copying and/or sending to the same or different user in various human readable formats (email, html etc). In some embodiments, optimized methods designed by the in silico methods described herein can be shared by a plurality of users.

Methods of the disclosure can further include performing laboratory steps (corresponding to the in silico steps) to confirm and possibly expand the determinations made using the in silico methods to produce a biotechnology product that is optimal (in quality and/or quantity (yield)) and/or arrive at a biotechnology method with optimal efficiency for producing a biotech product.

In some embodiments, a biotechnology process of the disclosure, may be a computational biology process(es). Biotechnology processes and their analysis is often carried out in multistep processes that can be generalized steps, customized steps and/or a combination of generalized and customized steps.

In some embodiments, steps for a biotechnology process, according to the present teachings may comprise an ordered sequence of steps (wherein step 1 must be followed by step 2). In some embodiments, steps of a biotechnology process may comprise an unordered/random sequence of steps (wherein steps 1, 2, 3, . . . may be performed in no specific order or pattern). In some embodiments of an in silico method, for an unordered series of method steps a final confirmation step comprising a user input provided has to be provided by the user before the final step of the process can be executed.

Figure 3:
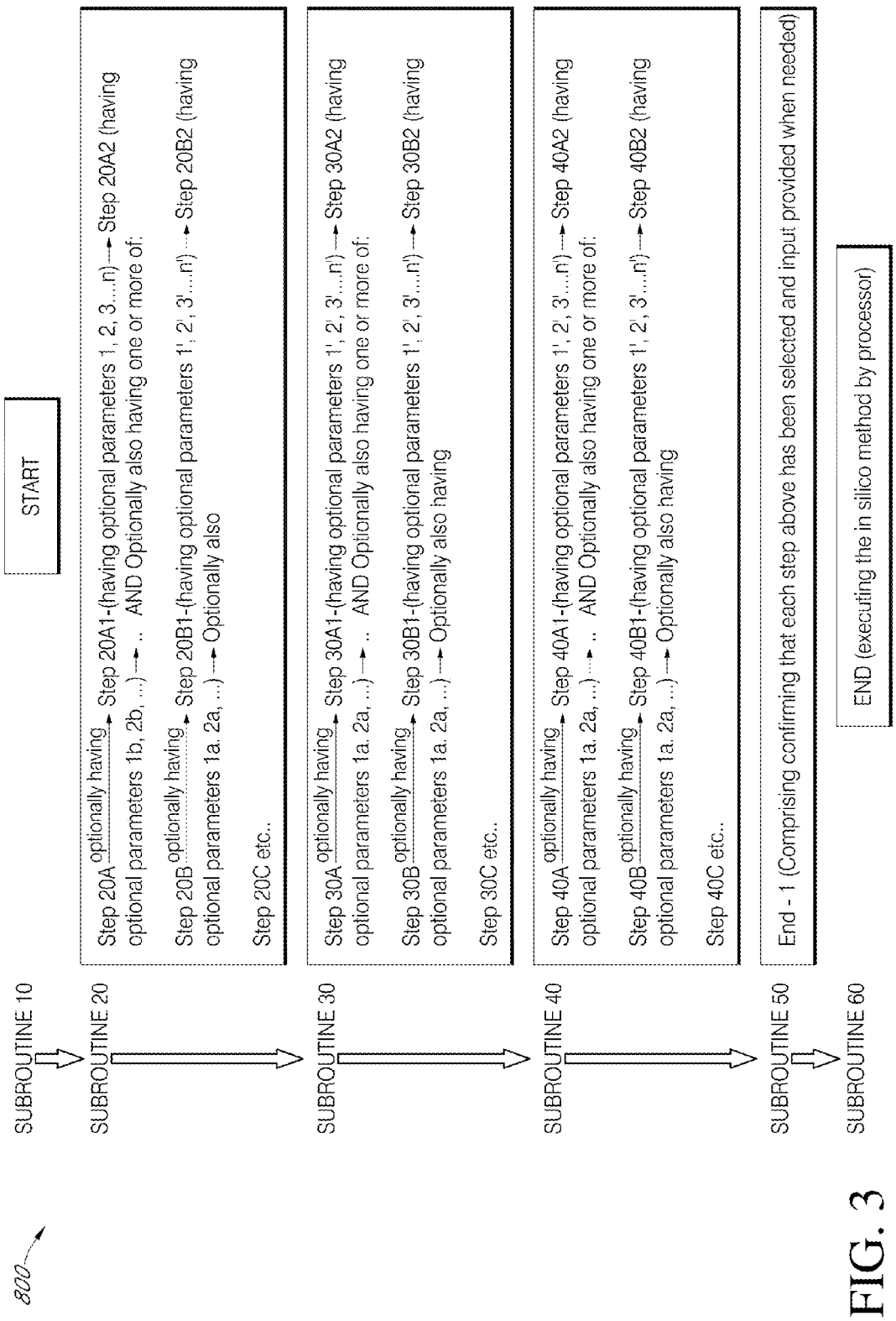
FIG. 3 depicts a flow chart of an example method 800 according to an embodiment of the present disclosure.

FIG. 3 depicts an exemplary in silico method 800 according to one embodiment of the present invention. In silico method 800 includes a plurality of set workflow subroutines in a computer readable format that can include subroutines for a biotechnology process depicted in FIG. 3 as Subroutine 10, Subroutine 2, Subroutine 30 . . . and so on. FIG. 3 is merely an exemplary method and the skilled artisan, in light of this disclosure, will realize that the actual number of subroutines can vary from at least about 2 subroutines to many (e.g. 2-10, 2-20, 2-30, 2-n (where n may be any number of subroutines from 3-100, 3-1000 and so on)). Each set subroutine 10, 20, 30, 40, 50, 60 . . . etc. can include a single step or task, or optionally can include more than 1 step or task (e.g. Steps A, B, C . . . shown as Step 20A, 20B, 20C for Subroutine 2; and as 30A, 30A1, 30A2 for Subroutine 30), also in a computer readable format, and each step can further include additional optional customizable steps or tasks shown in FIG. 3 as Steps A1, A2, B1, B2, C1-C2 . . . (e.g. shown as Step 20A1, 20A2 for Step 20A; and Step 20B1, 20B2 for Step 20B of Subroutine 20; and as Step 30A1, 30A2 for Step 30A; and Step 30B1, 30B2 for Step 30B of Subroutine 30). Each of the optional/customizable steps or tasks can have one or more optional parameters (options) that can be viewed, reviewed, set or customized by a user for example see 1, 2, 3, 1a, 2a1b, 2b, 1', 2' . . . . In some embodiments, an in silico method of the invention includes selection by a user of at least one parameter each for each optional/customizable step of the biotechnological process using a graphical user interface (GUI) to select the at least one parameter for each optional/customizable step. In certain embodiments, every step and every parameter of the subroutines of a workflow are available to a user to view, and optionally edit. Bioinformatics programs typically hide some of these parameters and/or steps from users, which causes user frustration and inefficiency especially when the result of an in silico designed experiment is not the expected result for a user.

An exemplary in silico method of the disclosure illustrated generally in FIG. 3 can be carried out (performed) by generating at least one method file in a computer system, the method file comprising computer readable instructions for a plurality subroutines (10, 20, 30 . . . ) of customizable steps (A, B, C) each of which may have one or more parameters that may be viewed, selected, changed or inputted; and performing the biotechnological process in silico comprising executing the at least one method file comprising computer readable instructions by the computer system to obtain at least one biotechnology product.

In some embodiments, at least one customizable/optional parameter is selected from a default parameter, wherein the default parameter is stored in a component of the computer system (such as storage, database etc.).

Accordingly, in some embodiments, the present disclosure provides a non-transitory computer-readable storage medium encoded with instructions, executable by a processor, the instructions comprising instructions for providing a method for performing a biological workflow in silico comprising: presenting to a user a plurality of subroutines that comprise the biological workflow listed in a sequential order, wherein at least two subroutines of the plurality of subroutines comprise two steps; providing the user ability to navigate to any subroutine of the plurality of sequential subroutines, to select a subroutine and view, set, select, or change one or more parameters associated with a step of the selected subroutine; providing an option to display to the user, one or more biomolecules resulting from execution of one or more of the plurality of subroutines; and providing an option to the user to navigate to a prior subroutine and change a parameter of a step of the prior subroutine, if the user is not satisfied with the one or more displayed biomolecules.

In some embodiments, a method of the disclosure may further comprise, providing an indication to the user of a current subroutine of the method for performing a biological workflow for the user to review. An indication may be provided by highlighting in a GUI the current subroutine. A GUI type display may also be used to display to a user the number of steps in a selected subroutine. In some embodiments, multiple display panes in a GUI may be used, one display pane to show the subroutine step and another display pane to show the steps in that subroutine.

Some embodiments also provide an indication of a current step by highlighting for example a step or task within a subroutine to a user to which a user has navigated.

In some embodiments, a method of the disclosure may further comprise, receiving at least one selection desired by the user, from the user, for one or more parameters associated with at least one step of the plurality of subroutines of the method for performing a biological workflow; and providing to the user an option for storing in a memory a user defined workflow comprising settings selected by the user for parameters used in the biological workflow. A user defined workflow may also be described herein as a user defined method of a biological workflow.

In some embodiments, a method of the disclosure may further comprise providing to the user the ability to rate or comment on the user defined workflow and storing the rating associated with the user defined workflow in the memory.

In some embodiments, a method of the disclosure may further comprise providing to a user, preset settings for parameters based on user defined workflows with the highest ratings or the most positive comments. In some embodiments, a method of the disclosure may further comprise instructions for ability for a plurality of users to provide feedback about parameters selected for optimally performing the biological workflow; and storing feedback received from the plurality of users in a memory. In such embodiments, the software is able to "learn" from its experience based on user input and rating. Software of the disclosure may in some embodiments have neural networks and artificial intelligence capability.

In some exemplary embodiments, analysis of feedback provided by a community of users may be used to determine which parameters may be better suited for a particular step of a subroutine. For example, in a non limiting example of a biological workflow for designing a recombinant biomolecule some example optional parameters that may be selected by users in a step of a subroutine may be selection of a vector from several possible vector choices and selection of one open reading frame. A plurality of vectors and open reading frame choices may be stored in a memory (database) and presented as optional parameters to users (for example in a drop box format in a GUI), thereby allowing the user to design several possible recombinant biomolecules by selecting different combinations of vectors and open reading frames. A user could thus determine, in silico (and also additionally in the lab if desired), which combination would lead to the most optimum recombinant biomolecule and/or therefore determine the most optimum user-defined workflow for making the optimum biomolecule. If multiple users provide comments, rating or feedback that certain vectors are consistently not optimal; and/or a certain open reading frame are consistently not optimal across multiple users; and/or that a certain reading frame in combination with certain vectors do not provide an optimal recombinant biomolecule as desired, the software is designed to "learn" from this input and provide to a future user the information that certain vectors and ORF's may not be optimal for use in a workflow for making the recombinant biomolecule. On the contrary, if previous user input indicates that certain vectors are good, the software may display to a future user a list of vectors (and ORF's) that worked well in workflows for other users.

In some embodiments, the ability of the software to store user feedback and user workflows may allow a provider to make a kit selecting certain parameters (such as specific vectors, and ORF's in the example above), and/or sell or market certain products for use in a corresponding laboratory workflow.

In another exemplary embodiment, a biological workflow may comprise restriction cloning and once a user uploads a DNA fragment to be cloned the software may display options of Restriction Endonucleases (RE) that may be used to cut the DNA fragment from a list of possible enzymes based on the sequence. However, since some RE's are more expensive that others, users will preferentially never select the more expensive RE's from the list if another choice is available. A software of the disclosure is able to learn from repeated selections (and or comments, feedback) from multiple users and be able to suggest to a future user a less expensive choice of a RE, thereby able to generate a cost effective biological workflow for a user.

Accordingly, in some embodiments a non-transitory computer-readable storage medium of the present disclosure, encoded with instructions and executable by a processor may additionally comprise instructions for generating recommendations of parameters based on feedback received from the plurality of users and presenting generated recommendations to future users. In some embodiments, recommendations may be subroutine specific recommendations. In some embodiments, recommendations may be step specific recommendations.

In some embodiments, a method of the disclosure may further comprise providing the user the ability to navigate to any subroutine of the plurality of sequential subroutines to select a subroutine and view, set, or change one or more parameters associated with a step of the selected subroutine, wherein the parameter being viewed, set or changed is a parameter that results from ambiguous user data.

In some illustrative non-limiting exemplary embodiments, ambiguous user data may be generated for example by users during sequencing old DNA. Old DNA may include mummified DNA and/or fossilized DNA wherein the quantity of DNA is limited and the quality of DNA is poor due to the nature of the source of DNA. Typically workflows such as ContigExpress (explained and illustrated in detail in sections below and FIGS. 6 and 9) are used to build contig's of fragments sequenced from such old DNA and comprise several "subroutines" including "Subroutine 1=View Fragments"; "Subroutine 2=Trim ends;" "Subroutine 3=Trim vector contaminations;" "Subroutine 4=Assemble contig;" and "Subroutine 5=View Contig." Prior to the subroutines 1 of "viewing fragments" a user will typically "sequence DNA fragments" and upload them into a molecular viewed of the software. Due to the poor DNA quality there is a lot of "fuzziness" at ends of fragments, which is due to the inability of a DNA sequencing machine to determine accurately the intensity of signal of nucleotides (for example, a capillary electrophoresis machine is unable to detect clearly is a peak is an "A" or "T").

In this example, while performing the "subroutine 1 of View Fragments" typically all bioinformatics software automatically trim off the "fuzzy" end fragments, where the sequence is not clearly readable. Typically, bioinformatics software does this inherent trimming of "fuzzy" ends and provides no indication to a user of the fact that such trimming was done. Typically this frustrates and confuses users as they do not see the expected length of fragment in the display and have no way of knowing what happened (no way of knowing that bioinformatics software typically trims fuzzy ends). The present software, in contrast to existing software, keeps a log(electronic log) of all the steps it executed and a viewer, is confused, can navigate and look at the electronic log and see a Table that will show the nucleotides and positions that were trimmed and a note of why they were trimmed in the example of where a fragment viewed does not have an expected length (for example). The present software also provides in a subroutine options to view, select, change, steps/parameters to not automatically remove such ambiguous user data For example, in this illustrative example, the present software has the ability to allow a user to select a step/parameter that does not trim the fuzzy lengths off.

In some embodiments, a method of the disclosure may further comprise providing the user the ability to navigate to any subroutine of the plurality of sequential subroutines to select a subroutine and view, set, or change one or more parameters associated with a step of the selected subroutine, wherein ever parameter in a workflow that is set based on ambiguous user data can be viewed, set, or changed by the user.

In some embodiments, a method of the disclosure may further comprise providing the user the ability to navigate to any subroutine of the plurality of sequential subroutines to select a subroutine and view, set, or change one or more parameters associated with a step of the selected subroutine, wherein ever parameter in a workflow that is set based on ambiguous user data is highlighted to a user such that the parameter can be viewed, set, or changed by the user.

In some embodiments, the non-transitory computer-readable storage medium also provides to a user the ability to save a log of all selected parameters for each step of the user defined method; and also optionally receive and store from the user at least one comment about the user defined method. Therefore, in some embodiments, an electronic lab notebook function is provided which allows a user to carefully look back at each and every selection and analyze the outcome of a biological workflow.

In some embodiments, the software of the present disclosure also has the capability for storing one or more external files uploaded by the user; and providing to the user or to additional users ability to view the one or more external files uploaded. This may be helpful when multiple users run an experiment. For example, in a cloning workflow, if 5 inserts are desired to be cloned into 5 vectors, an excel file of all possible combinations of vector and inserts may be made and multiple users can enter data an update the excel sheet as a progressive log book of the experiment. Various versions of a file may be uploaded and accessed.

In some embodiments, viewing, selecting, setting, or changing one or more parameters associated with a step of the selected subroutine by the user comprises using a graphical user interface (GUI).

In some embodiments, the one or more parameters viewed, selected, set or changed by the user are from one or more default parameters, wherein default parameters are pre-determined parameters stored in the computer-readable storage medium.

In some embodiments, the one or more parameters viewed, selected, set or changed by the user comprise at least one user input parameter.

In some embodiments, the user input parameter is a modified default parameter, a parameter input by user, or a parameter imported by the user into the computer system, wherein a default parameter is a pre-determined parameter stored in a component of the computer-readable storage medium.

In some embodiments, the one or more parameters viewed, selected, set or changed by the user comprise a combination of one or more default parameters and one or more user defined parameters, wherein default parameters are pre-determined parameters stored in a component of the computer-readable storage medium and wherein the user input parameter is a modified default parameter, a parameter input by user, or a parameter imported by the user into the computer system.

In some embodiments, providing the user ability to navigate to any subroutine of the plurality of subroutines is by a graphical user interface (GUI) which comprises displaying on a first display screen pane all the subroutines of a sequential subroutine comprising the biological workflow and, following selection by the user of any one subroutine, displaying on a second display screen, one or more steps associated with the selected subroutine.

In some embodiments, providing the user ability to navigate to any step of a subroutine is by a graphical user interface (GUI) which comprises displaying on a first display screen pane the subroutine and displaying on a second display screen, one or more steps associated with the selected subroutine.

In some embodiments, providing to the user an option for saving on the computer readable storage medium a user defined method comprising at least one selection desired by the user comprises: receiving selections by the user of one or more parameters for each step of the plurality of subroutines of the biological workflow and saving the selections as a selected plurality of steps, wherein the saved selected plurality of steps comprise the user-defined method; and storing a user defined name for the user-defined method.

In some embodiments, providing to the user an option for saving on the computer readable storage medium a user defined method comprising at least one selection desired by the user comprises: a) displaying on a display screen pane a prescribed plurality of subroutines in a sequential order of the biological workflow, wherein the prescribed plurality of subroutines are comprised in a computer readable format; b) navigation by a user using a graphical user interface (GUI) on the display screen of each subroutine of the prescribed plurality of subroutines of the biological workflow; c) selection by the user of one of the subroutines; d) navigation by a user using a GUI on the display screen of each step of a selected subroutine; e) selection by the user of one or more parameters in each step of a selected subroutine to obtain a modified plurality of steps; f) storing the modified plurality of steps by the user, wherein the stored modified plurality of steps comprise the user defined subroutine; g) repeating steps b)-f) till all the plurality of sub routines are stored as user defined subroutines; and h) saving and executing the plurality of user defined subroutines to perform a user defined biological workflow.

In some embodiments, navigation by a user of any subroutine or step of the workflow is in a sequential order of the steps or the subroutine. In some embodiments, navigation by a user of any subroutine or step of the workflow is in a non-sequential order of the steps or the subroutine.

In some embodiments, an in silico workflow may further comprise executing a first user defined workflow comprising executing in silico all the steps of a first user defined workflow in sequential order; viewing a first biomolecule obtained by executing the first user defined workflow in silico; generation of at least a second user defined workflow, comprising changing the selection of at least one parameter to have a different value relative to the same parameter that was selected in the first user defined workflow; executing in silico the at least second user defined workflow to obtain a second biomolecule; viewing the second biotechnology product in silico; and comparing the first biomolecule with the second biomolecule, thereby allowing a user to determine if the first user defined workflow or the second user defined method is better. In this embodiment, the ability to accurately determine the parameters by means to the stored workflows in a memory, allow changing one parameter in relation to another.

Exemplary non-limiting biological workflow include a cloning method, a recombination method, a ligation method, a vector designing method, a method for synthesis of a nucleic acid, a primer design method, a method for synthesis of a polypeptide, method for analysis of a cloned molecule, method of protein analysis, method for making a modified host.

In some embodiments, a non-transitory computer-readable storage medium of the disclosure, encoded with instructions, executable by a processor, the instructions comprising instructions for: providing a pipeline of a method for performing a biological workflow for display to a user, the pipeline of a method comprising a plurality of methods, each method generating at least one biomolecule that may be used in the next method to produce another biomolecule, wherein subroutines of each of the plurality of methods are listed in a sequential order; and executing the pipeline of the method.

In some embodiments, generation of the at least one method file may comprise selection by a user of at least one default parameter or selection of at least one user input parameter for each step of the biotechnological process, wherein the at least one default parameter is stored in a component of the computer system and wherein the at least one user input parameter is a modified default parameter, a parameter input by user, or a parameter imported by the user into the computer system.

In some embodiments, the generation of the at least one method file may comprises: displaying on a display screen at least two or more sequential subroutines (subroutines 10, 20, 30 . . . as in FIG. 3) of a prescribed workflow of a biotechnological process, wherein the two or more steps are comprised in a computer readable format in the computer system; navigation by a user using a graphical user interface (GUI) on the display screen of each of the two or more subroutines (go to each of subroutines 10, 20, 30, and thereby be able to further navigate and explore steps A comprising steps A1, A2 each of which have options 1, 2, 3 . . . n 1*b*, 2*b*, etc. . . . ) of the biotechnological process; selection by the user of one or more parameters in each step (Step A, Step A1, Step B Step B1 etc. . . . ) of the plurality of subroutines for the biotechnological process to obtain a selected plurality of steps; and storing (saving) the selected plurality of steps (and hence selected subroutines) by the user in a memory, wherein the stored selected plurality of subroutines comprise the at least one user-generated workflow method file.

In some embodiments, the disclosure describes an in silico method comprising a subsystem having a prescribed workflow of a biotechnology process. A prescribed workflow typically comprises a method file in a computer system comprising computer readable instructions of a plurality of subroutines of a biotechnological process, wherein performing each subroutine of the biotechnological process would lead to a biotechnology product. For example, in a non limiting example biotechnology process is a process for cloning, a prescribed workflow of the disclosure may comprise generating a method file in a computer system comprising computer readable instructions for a plurality of subroutines such as, but not limited to: amplifying fragments to use in cloning; inserting a gene of interest into an entry clone; previewing entry clones; using entry clones for cloning into a expression vector; create expression clones; preview expression clones. A sequential subroutine of such a prescribed workflow are presented to a user in a GUI with each step as a link/button on the GUI which when selected by a user leads a user to another GUI screen with further details regarding that particular subroutine. For example, in the process for cloning described above, selecting the subroutine of "amplifying fragments to use in cloning" would lead a user to a screen showing various steps of this subroutine. Each step may further have sub-steps or several parameters each of which may be displayed in a GUI using one or more buttons for each sub-step/parameter, for example using certain primers for the amplification which may be designed for insertion of the amplified product into an entry clone plasmid.

In some embodiments, a prescribed workflow allows a user to view in silico all steps of a workflow to make a biotechnology product. A prescribed workflow also allows a user to in silico navigate to each step and understand what each step entails. One or more advantages of a prescribed workflow of the disclosure are allowing users to view all steps required for a particular biotechnology process thereby providing users with an overview of the process requirements. This may especially help users that are new and users that may not be familiar with that particular biotechnology process. Other advantages of a prescribed workflow of the disclosure is providing to a user a prescribed number of steps to ensure that the workflow is standardized and results are assured to have been processed in a similar fashion to provide consistency between different executions of the method files/protocols.

In some embodiments, a prescribed workflow allows a user to select or input parameters for each step and save and load the workflow so a user may return to the workflow later to review it or to provide it to other users so all users may perform the same workflow.

Figure 4:
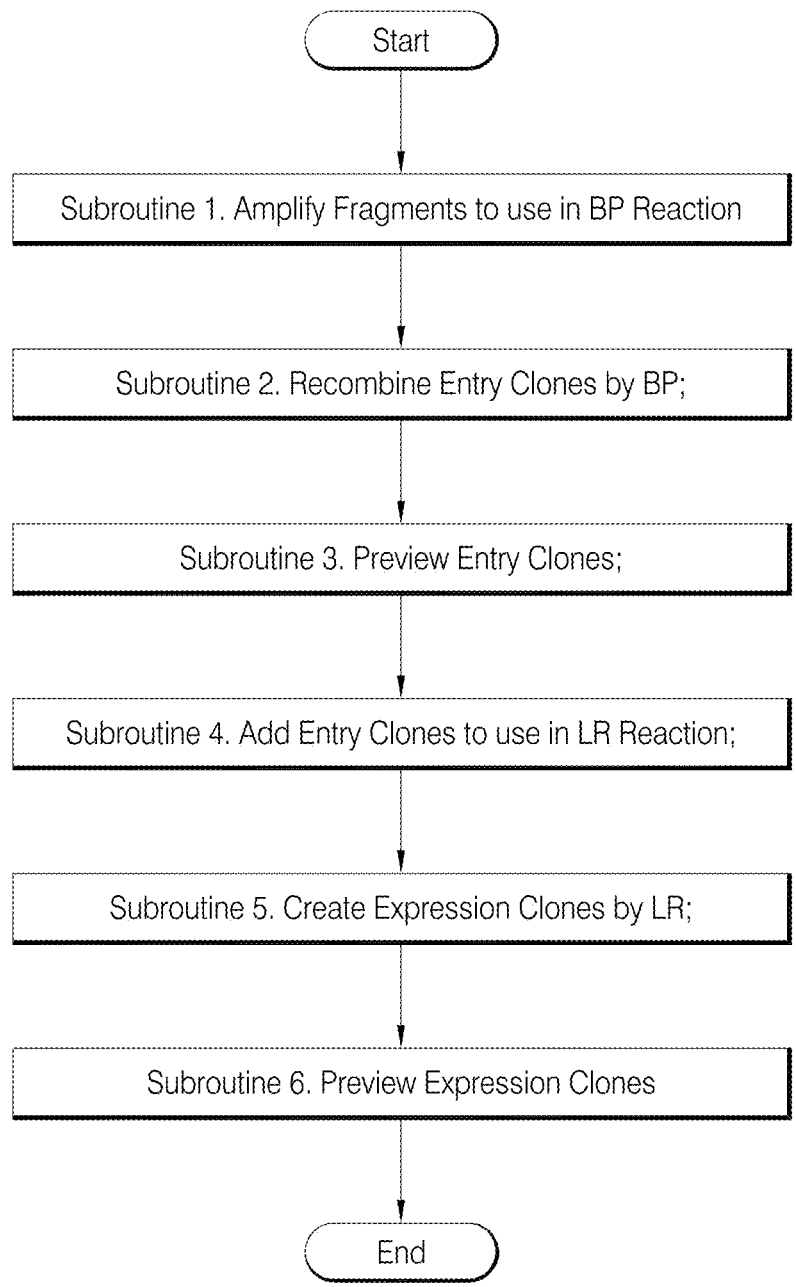
FIG. 4 depicts an example workflow method according to an example embodiment of the present disclosure.

Some example prescribed workflows of the disclosure include a Prescribed Workflow for execution of Gateway® Cloning which is shown for example in FIG. 4. Here, the users are notified via a GUI of a "prescribed workflow" comprising a plurality of sequential subroutines involved in performing Gateway® Cloning which include for example: Subroutine 1. Amplify Fragments to use in BP Reaction; Subroutine 2. Recombine Entry Clones by BP; Subroutine 3. Preview Entry Clones; Subroutine 4. Add Entry Clones to use in LR Reaction; Subroutine 5. Create Expression Clones by LR; and Subroutine 6. Preview Expression Clones. As a user clicks (selects) each step (in order or random order) conditions, parameters and possible options for each step appear as additional GUI screens with Navigation panels to choose, populate, save, return to previous and/or enter one or more parameters or values.

Figure 5:
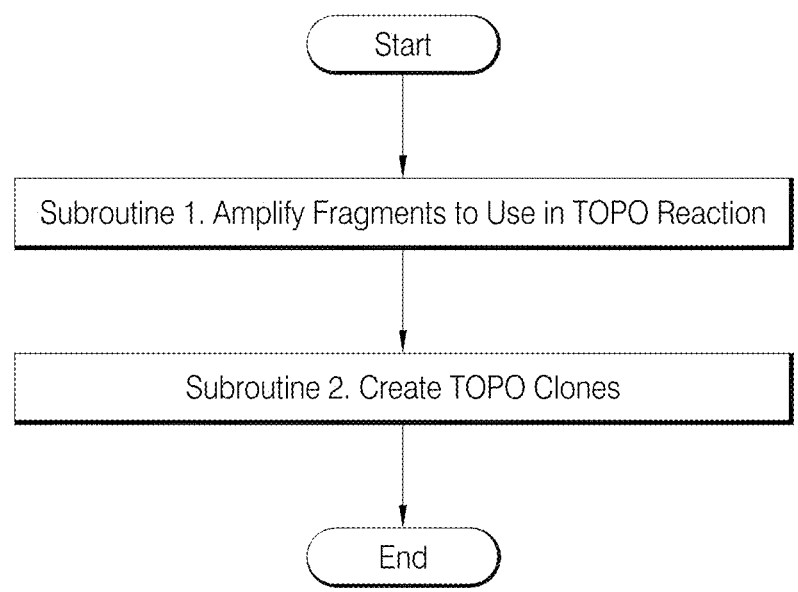
FIG. 5 depicts a flow chart of an example workflow method according to an embodiment of the present disclosure.
Figure 6:
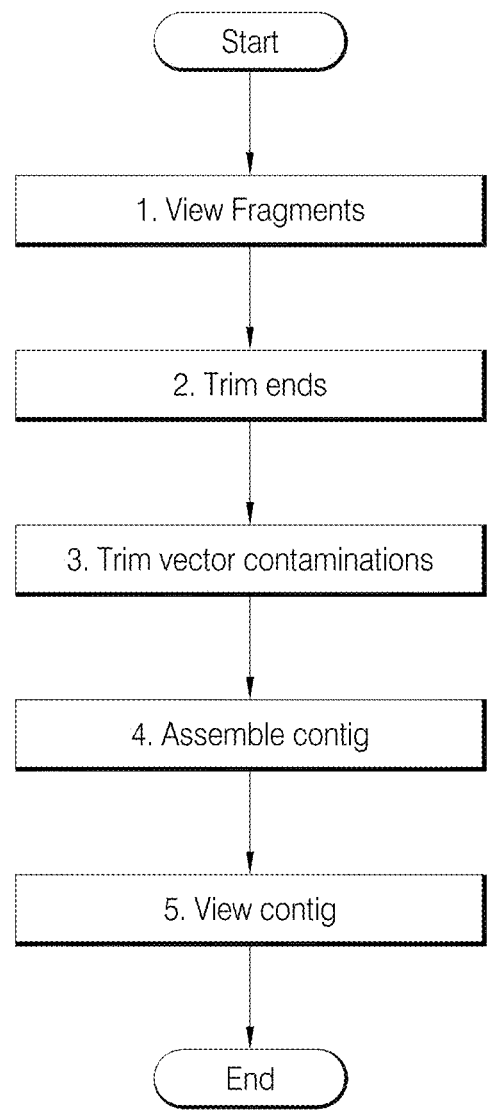
FIG. 6 depicts an example workflow method according to an example embodiment of the present disclosure.

Other non limiting examples of Prescribed Workflows of the disclosure are TOPO® Cloning and ContigExpress® which are depicted in FIG. 5 and FIG. 6 respectively. FIG.

5 depicts an exemplary prescribed workflow of the disclosure for TOPO® Cloning which comprises the following subroutines: Subroutine 1. Amplify fragments to use in TOPO® reaction; Subroutine 2. Create TOPO® clones; and Subroutine 3. Preview clones. Detailed GUIs for each of these steps of the prescribed workflow are shown in FIGS. 8A-8H.

FIG. 6 describes an example prescribed workflow of the disclosure comprising a biological workflow for ContigExpress® and comprises the following subroutines: Subroutine 1. View Fragments; Subroutine 2. Trim ends; Subroutine 3. Trim vector contaminations; Subroutine 4. Assemble contig; and Subroutine 5. View contig. Detailed GUIs for each of these steps of the prescribed workflow are shown in FIGS. 9A-9G.

Figure 7A:
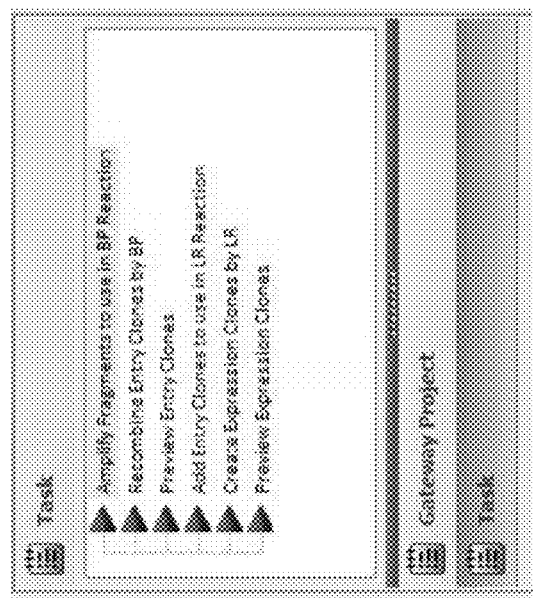
Figure 7B:
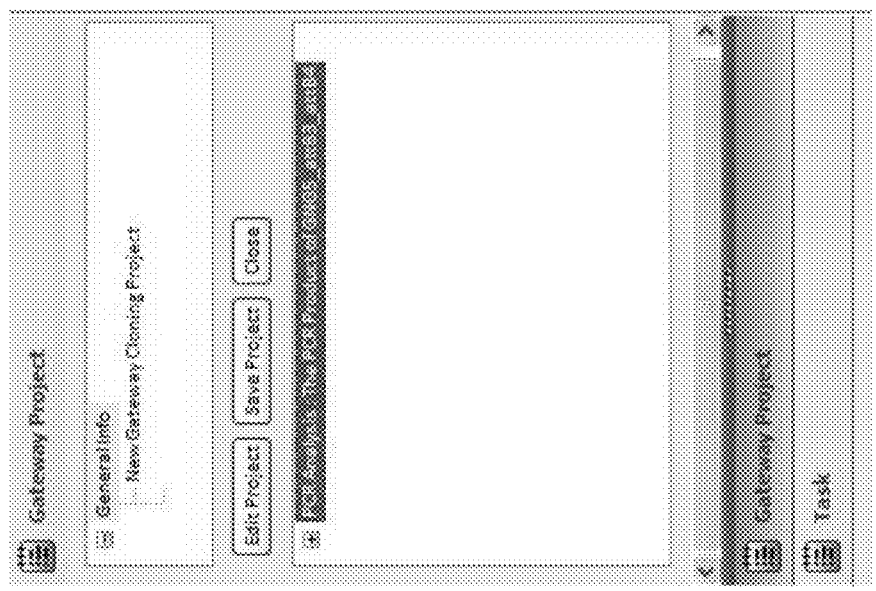
FIG. 7B depicts a Task List GUI.
Figure 7C:
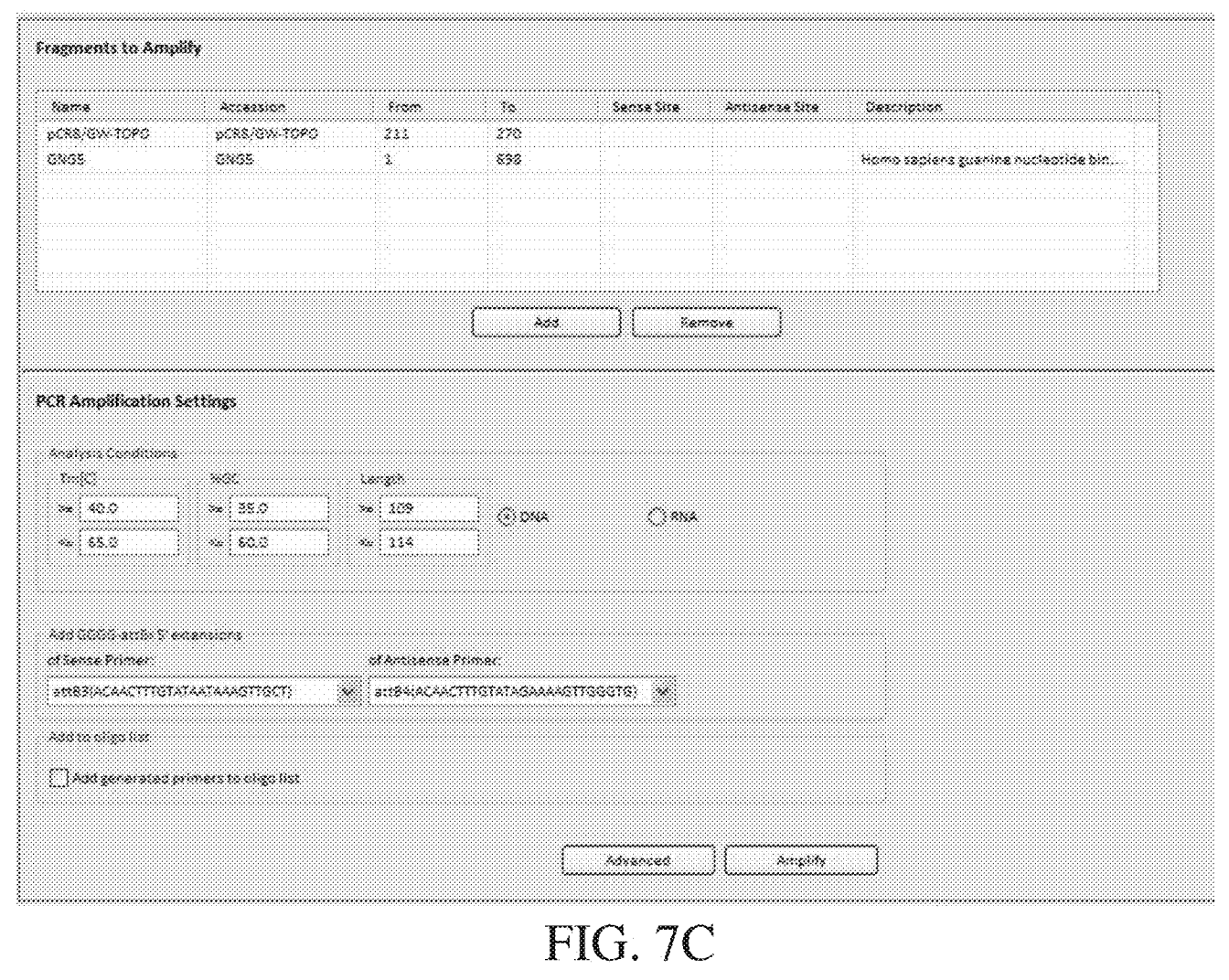
Figure 7D:
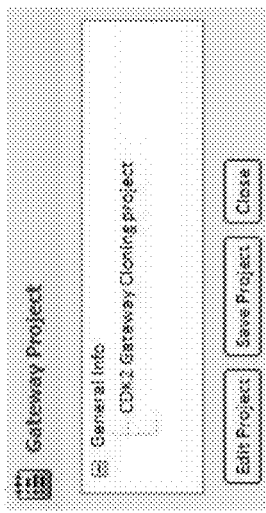
FIG. 7D depicts a Gateway® Project GUI with options for navigating to additional screens such as Saving, Editing and Closing Projects.
Figure 7E:
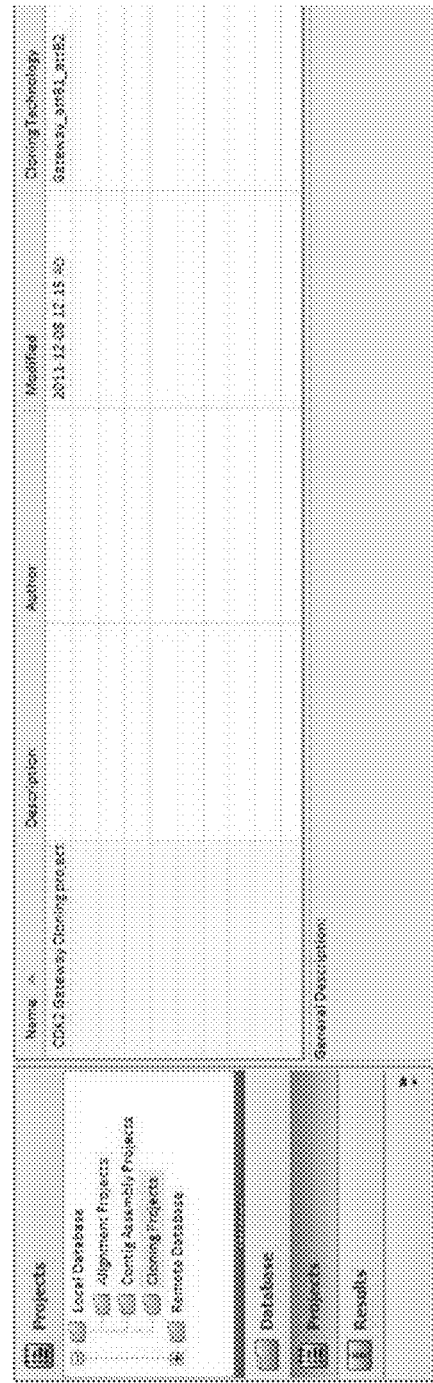
FIG. 7E depicts showing a Projects GUI.
Figure 7F:
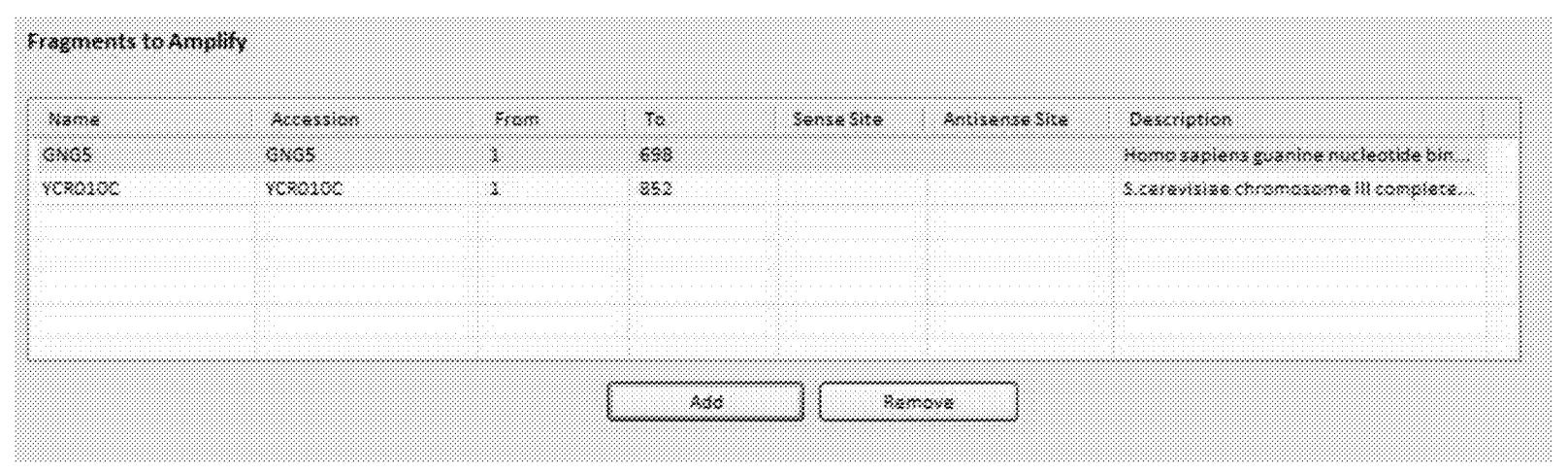
Figure 7G:
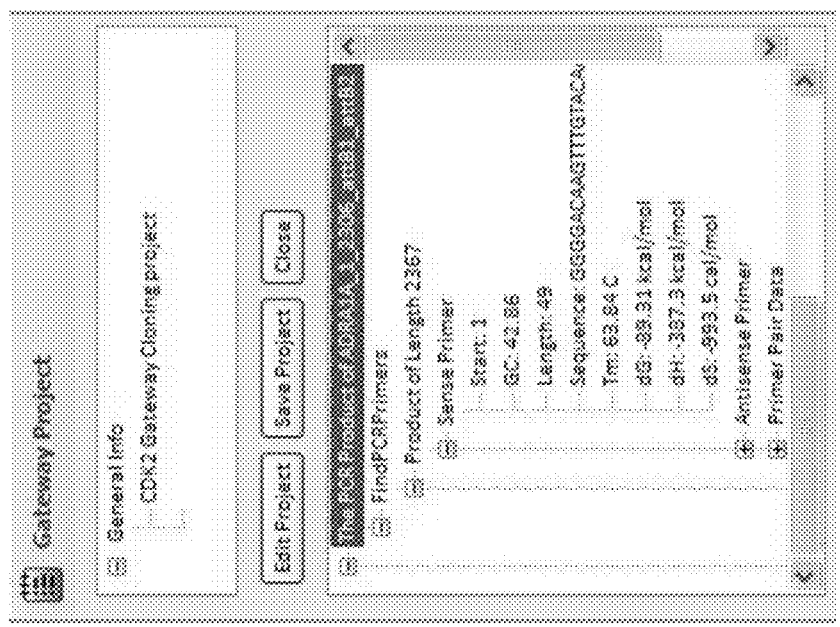
FIG. 7G depicts a GUI when Amplify button is selected (FIG. 7G discloses SEQ ID NO: 3)
Figure 7H:
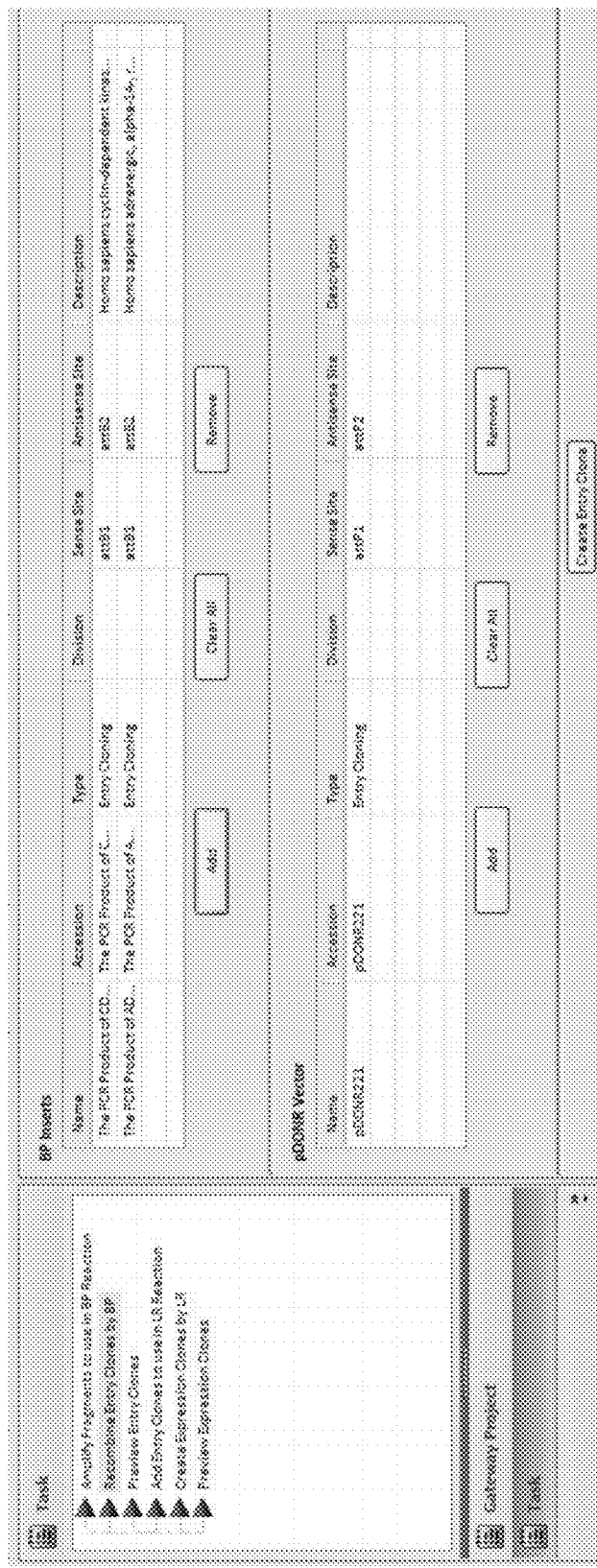
FIG. 7H depicts a Recombine Entry Clone by BP task pane GUI.
Figure 7I:
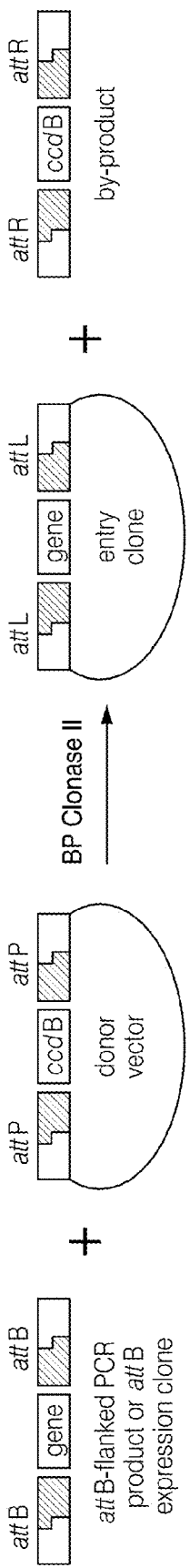
FIG. 7I depicts a pDONR® Vector which is an Gateway® Cloning vector.
Figure 7J:
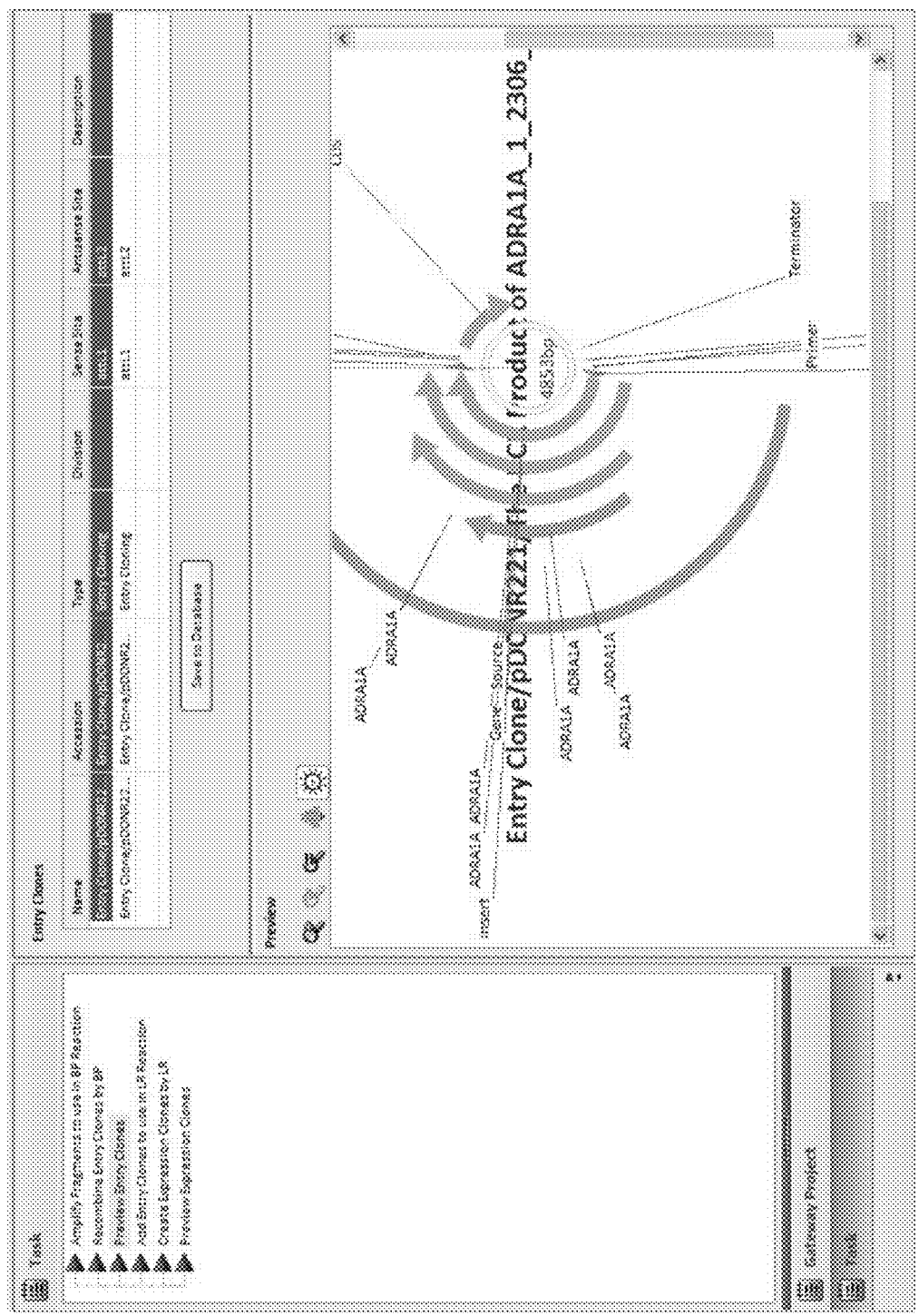
FIG. 7J depicts a Preview Entry Clone task pane GUI.
Figure 7N:
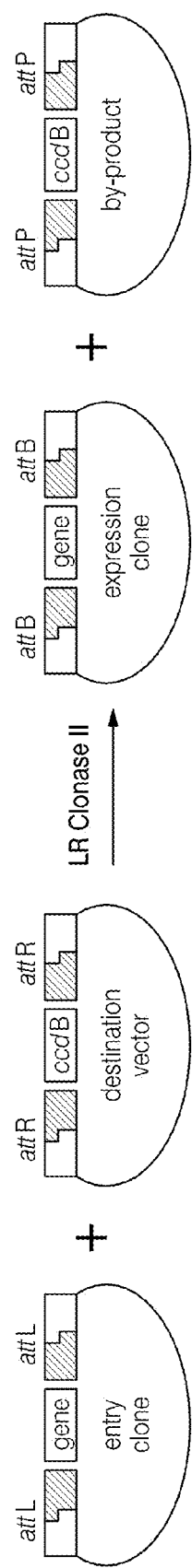
FIG. 7N depicts a pDEST® Vector.
Figure 7O:
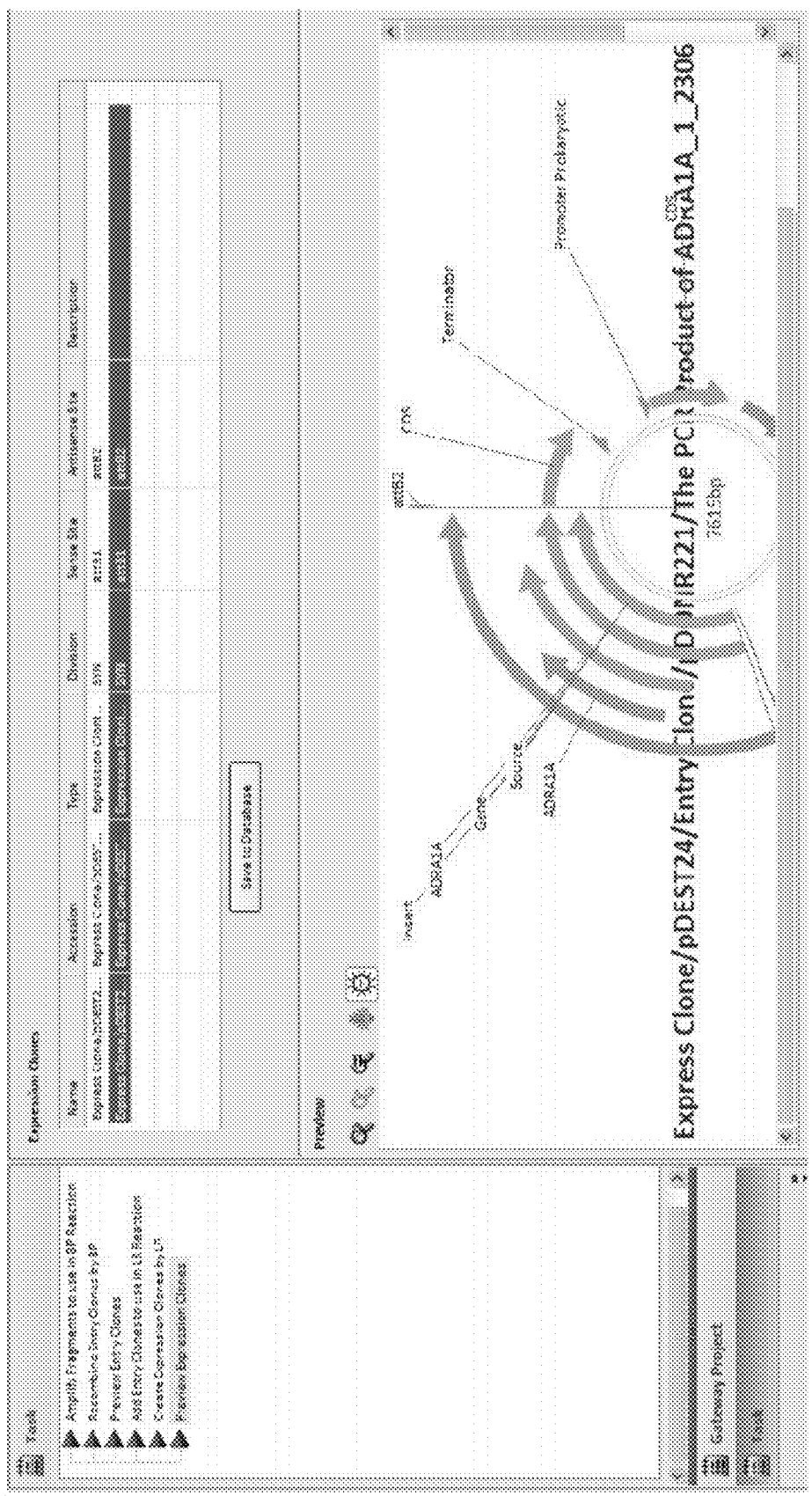

GUIs of prescribed workflows for Gateway Cloning are shown in FIGS. 7A-7O. GUI's of TOPO Cloning are shown in FIGS. 8A-8E and GUI's for ContingExpress are shown in FIGS. 9A-9G. Details of these figures (i.e., subroutines and steps of subroutines of these workflows) are described in sections below.

Gateway® Cloning Technology is a rapid and highly efficient method for the cloning and subcloning of DNA segments. This system is based on the well-characterized bacteriophage lambda-based site-specific recombination system (attLx attR attBx attP). Gateway® Cloning is a 2-step process. In the first step a sequence of interest containing attB sites is recombined with a donor vector containing attP sites into an entry clone, creating attL sites in the process. The second step recombines the attL-containing entry clone with a destination vector containing attR sites, generating an expression clone that can be propagated and expressed in a range of host cells for a given experiment. Additional detailed information on Gateway® Cloning, see the *Gateway® Technology User Guide* or the *Gateway® Technology with Clonase™ II User Guide*, available for download from www.lifetechnologies.com/manuals.

A prescribed workflow of the disclosure for Gateway Cloning may comprise 1) Step 1 comprising creating an entry clone which in some embodiments may comprises creating an entry clone in the Vector NTI Express Gateway® Cloning Tool by a) amplifying a sequence or molecule of interest with attB containing primers designed by the software; b) performing BP recombination with a donor (pDONR) vector to generate an entry clone. This generates a product described as the following:

PCR product(flanked by attB sites)+pDONR vector
(with attP)Entry Clone(with attL)

In some embodiments, Step 1, comprising creating an entry clone, may comprise the following alternative methods:
i. Selecting an existing attB-containing DNA molecule—From within the Gateway® Cloning Tool, a user can select an already existing attB-containing DNA molecule in the database, such as a Gateway®Expression Clone or a pCMVSPORT6 library, for recombination with a donor vector, to create an entry clone; or
ii. Constructing an entry clone by alternative molecule construction methods—A user may alternatively construct his/her own entry clone using other Vector NTI Express molecule construction methods, ensuring that the created clone contains the required attL1 and attL2 sites (labeled as features as described in "Add Entry Clones to Use in LR Reaction"); and saving the molecule in the database; and selecting it directly in the Gateway® Cloning tool.

Step 2 of the prescribed workflow for Gateway Cloning comprises creating an expression clone which may comprise using the Gateway® Cloning Tool, entry clones created from any of the above methods (described under step 1) are recombined with destination (pDEST) vectors in an LR recombination reaction to generate expression clones, which can drive expression of the sequence of interest when transformed into host cells.

The Gateway® Cloning Tool contains settings and functions for assembling a Gateway® construct using the workflow described above, and for creating and managing Gateway®. An example workflow of the disclosure comprising a GUI would begin with Opening the Gateway® Cloning Tool.

There are several ways to open the tool and these may comprise: 1) Clicking on the Gateway Cloning button on the main toolbar; or 2) With a molecule open in Molecule Editor, right-click in the Graphics or Sequence pane and select Launch Gateway.; or 3) Load an existing Gateway® Cloning project as described later in describing the GUI for "Create, save, and load projects."

The tool window is composed of the following panes:
Gateway® Project Pane: This pane displays the name of the current project, and includes controls for editing, saving, and closing projects. It also lists any generated molecules for the current project. Click on the Gateway Project button to display the GUI pane as shown in FIG. 7A The Task List pane: displays the list of tasks in the selected project. Clicking on the Task button of the Gateway Project Pane display the list as shown in FIG. 7B. As a user navigates through the Gateway® Cloning workflow, the Task List displays the current task, and allows a user to move between tasks by clicking on a different task (see FIG. 7B). Current Task pane as depicted in FIG. 7C displays the commands and settings for the currently selected task in the project. As a user navigates through the Task List workflow, the functions in this pane will change.

The Create, save, and load projects are tools for saving, editing, and closing projects are located in the Gateway® Project pane and are depicted in FIG. 7D. To save a new Gateway® Cloning project, a user may click on Edit Project in the Gateway® Project pane. In the dialog, a user may enter a name and any description for the project. To save changes to a project, a user may click on the Save Project button. To close a project, a user may click on the Close Project button. If there are unsaved changes, a user will be prompted to save the project before closing.

To load an existing project, in Database Explorer, a user may navigate to the Projects list as shown in FIG. 7E, double-click on the Projects folder, select the Cloning Projects subfolder from the Local Database, and double-click on the Gateway® Cloning project in the list to open it.

The Task List displays the default Gateway® Cloning workflow comprising the following steps as shown in the flowchart in FIG. 8: Amplify Fragments to Use in BP Reaction; Recombine Entry Clones by BP; Preview Entry Clones; Add Entry Clones to Use in LR Reaction; Create Expression Clones by LR; Preview Expression Clones. Each task in the workflow is described here and illustrated in FIGS. 7F-7O. For example, FIG. 7F depicts the Amplify fragments to Use in a BP reaction GUI. The Amplify Fragments to Use in a BP Reaction task is the first default task displayed when a user first opens the Gateway® Cloning Tool. The first step in this task to select the fragment(s) you want to amplify by PCR for use in a BP cloning reaction. These fragments will be listed in the Fragments to Amplify list.

Loading molecules or fragments in the Fragments to Amplify list: With a molecule open in Molecule Editor, a user may right-click in the Graphics or Sequence pane and select Launch Gateway to load the entire sequence in the list. Alternatively, with a molecule open in Molecule Editor, a user may select a portion of the sequence in the Graphics or Sequence pane, right-click, and select Launch Gateway to load only that part of the sequence in the list. In another alternative embodiment, with the Gateway® Cloning window open, a user can ensure the Amplify Fragments to Use in BP Reaction task is selected and click on the Add button under Fragments to Amplify to select a complete molecule from the database. In some embodiments, to change the regions to amplify in the selected molecules, a user may type a new range in the From and To fields in the Fragments to Amplify subpane.

Amplification settings: With the fragment(s) loaded, a user can select the desired amplification settings under PCR Amplification Settings. The standard options are described in the Table below.

| | |
|---|---|
| Tm(C.) | Enter limits in degrees Celsius for primer melting temperature (Tm) (temperature at which 50% of primer is a duplex) and the difference between Tm for sense and anti-sense primers. |
| % GC | Enter limits in degrees Celsius for primer melting temperature (Tm) (temperature at which 50% of primer is a duplex) and the difference between Tm for sense and anti-sense primers. |
| Primer Length | Defaults to 20-25, recommended for Gateway® Primers |
| DNA/RNA button | Select the type of nucleotide sequence. |
| Add GGGG-attBx 5′ Extensions | The default attB extensions are for single fragment cloning: attB1 for the sense primer and attB2 for the antisense primer. Select from the dropdown list to replace the defaults with other attB sequences for creating Entry Clones for MultiSite Gateway® Cloning projects. |
| Add generated primers to oligo list | Select this checkbox to add the primers a user can generate to the oligo list |

For additional amplification settings, a user may click on Advanced. The advanced amplification settings are identical for all PCR primers, and are similar to Primer Design described previously.

After making the selections as described above a user may click on the Amplify button. The next task pane will be displayed, and the generated PCR product(s) will appear listed in the BP Inserts subpane, and also listed in the Gateway® Project pane as depicted in FIG. 7G.

FIG. 7H depicts the Recombine Entry Clones by BP. In the Recombine Entry Clones by BP task pane, a user can modify the list of fragments with attB sites and select a donor (pDONR) vector or vectors with which to create entry clones.

BP Inserts: The fragments amplified by a user with attB sites are listed in the BP Inserts list at the top of the pane. To add a previously amplified fragment with attB sites, or a fragment designed with attB sites by another means (e.g., restriction-ligation), a user may click on the Add button and select the molecule from the database. To remove a molecule from list, a user may select it and click on Remove. To clear the entire list, a user may click on Clear All.

FIG. 7H depicts a pDONR vector which is a Gateway® Cloning vector that contains attP sites, which are recombined with the fragments containing attB sites to create entry clones. A variety of pDONR vectors are sold by Life Technologies, and in silico sequences for these are installed as part of the default Vector NTI Express installation. To select a pDONR vector a user may Click on the Add button and select the pDONR vector from the database. To remove a vector from list, a user may select it and click on Remove. To clear the entire list, a user may click on Clear All.

Create the Entry Clone pane: When a user has chosen selections, click on Create Entry Clone button will result in opening of the Preview Entry Clones task pane an example of which is depicted in FIG. 7J. Entry clones contain attL1 and attL2 sites, and are used to generate expression clones via an LR reaction.

In the Entry Clones list: a User may Select a clone and click on Save to Database to save it as a DNA molecule in the database. A user may Double-click on a clone to display it in the Preview window.

In the Preview window, magnifying tools depicted in FIG. 7K may be used to zoom in and out of the molecule and a molecule may be displayed as linear or circular by clicking on the buttons shown in FIG. 7L.

Add Entry Clones to Use in LR Reaction task: After creating entry clones, clicking on Add Entry Clones to Use in LR Reaction in the Task List proceed to the next task in the workflow. Any entry clone that is generated from the previous tasks in the workflow will be listed in this window. To select new or additional entry clones in the database, a user may click on the Add button and select from the dialog box. To remove an entry clone from the list, a user may select it and click on the Remove button.

Create Expression Clones by LR task: In the Create Expression Clones by LR task pane, shown in FIG. 7M, a user can modify the list of entry clones and select a destination (pDEST) vector or vectors with which to create expression clones.

Entry Clones: Any entry clones that were generated from the previous tasks in the workflow will be listed in the Entry Clones list. To select new or additional entry clones in the database, a user may click on the Add button and select from the dialog box. To remove an entry clone from the list, a user may select it and click on the Remove button. To clear the list, a user may click on Clear All.

A pDEST vector such as the one depicted in FIG. 7N is a type of Gateway® Cloning vector that contains attR sites, which are recombined with the fragments containing attL sites to create expression clones. A variety of pDEST vectors are sold by Life Technologies, and in silico sequences for these are installed as part of the default Vector NTI Express installation.

Preview Expression Clones: To select a pDEST vector: Click on the Add button and select the pDONR vector from the database. To remove a vector from list, select it and click on Remove. To clear the entire list, click on Clear All.

For the step of Creating the Expression Clone after a user makes selections as described above, a user may click on Create Expression Clone. The Preview Expression Clones task pane will open as depicted in FIG. 7O. A Preview Expression Clones task pane lists all the expression clones created from the entry clones and the destination vector(s) selected, and includes a preview window for viewing an expression clone as shown in an example embodiment in FIG. 7O.

In the Expression Clones list: a user may Select a clone and click on Save to Database to save it as a DNA molecule in the database or a user may Double-click on a clone to display it in the Preview window.

Another set of GUIs are described and depicted in a prescribed workflow relating to TOPO® Cloning in FIGS. 8A-8H. TOPO Cloning. TOPO® Technology is a fast, efficient way to clone. The key to TOPO® Cloning is the enzyme DNA topoisomerase I, whose biological role is to cleave and rejoin DNA during replication. To harness this activity, vectors are linearized and each end is conjugated with topoisomerase on the 3' phosphate. This enables fast ligation of DNA sequences with compatible ends. After 5 minutes at room temperature, the enzyme is released, the ligation is complete and the recombinant molecule is ready for transformation into E. coli. Many Life Technologies expression vectors are adapted for one-step TOPO® Cloning of PCR products in both directional and non-directional formats. Other vectors contain att recombination sequences exterior to the TOPO® cloning sites so that cloned inserts are Ready for entry into the TOPO® system.

TOPO® vectors can be grouped into three categories, based on the nature of their ends: Zero-Blunt vectors have two blunt ends and can accept blunt-ended DNA fragments, including amplicons produced by a proofreading polymerase. Inserts are cloned in both orientations.

T-A vectors have two ends with 3'-T overhangs. They can accept products of PCR amplification with a Taq polymerase, whose terminal transferase activity adds 3'A overhangs to the amplicon. Inserts are cloned in both orientations.

In directional vectors one terminal is blunt ended and the other has a 5'-GGTG overhang on the bottom strand. PCR products are generated with a 5'-CACC extension on one end and this strand when unwound is preferentially annealed to the vector overhang. More than 90% of the clones are in the correct orientation and the time spent in screening colonies is thereby reduced.

The presence of topoisomerase enzyme also helps protect vector ends from degradation, particularly from contaminating nucleases that may be present in ligase preparations. Moreover, the avoidance of restriction site cutback for cloning PCR products means that internal cleavage sites are not a problem.

Any linear, double-stranded DNA sequence of interest may be cloned into a TOPO® vector using Vector NTI Express. In addition, linear sequences with 3'-A overhangs, the products of PCR amplification with a Taq DNA polymerase, may be cloned into TOPO®-TA vectors. Such Taq-generated molecules can be generated in ® silico using the TOPO® Cloning tool.

An exemplary prescribed workflow of the disclosure is described by the TOPO® Cloning Tool. A user may begin this workflow by Opening the TOPO® Cloning Tool. The TOPO® Cloning Tool contains settings and functions for assembling a TOPO® construct using the workflow described above, and for creating and managing TOPO® Cloning projects. There are several ways to open the tool: A user may Click on the TOPO Cloning button on the main toolbar. Alternatively, with a molecule open in Molecule Editor, a user may right-click in the Graphics or Sequence pane and select Launch TOPO® Cloning. Still alternatively, a user may Load an existing TOPO® Cloning project as described in "Create, save, and load projects" buttons later. The TOPO cloning tool window is composed of the following panes:

TOPO® Project Pane: The TOPO® Project pane as depicted in FIG. 8A, displays the name of the current project, and includes controls for editing, saving, and closing projects. It also lists any generated molecules for the current project. Clicking on the TOPO® Project button to display this pane.

Figure 8B:
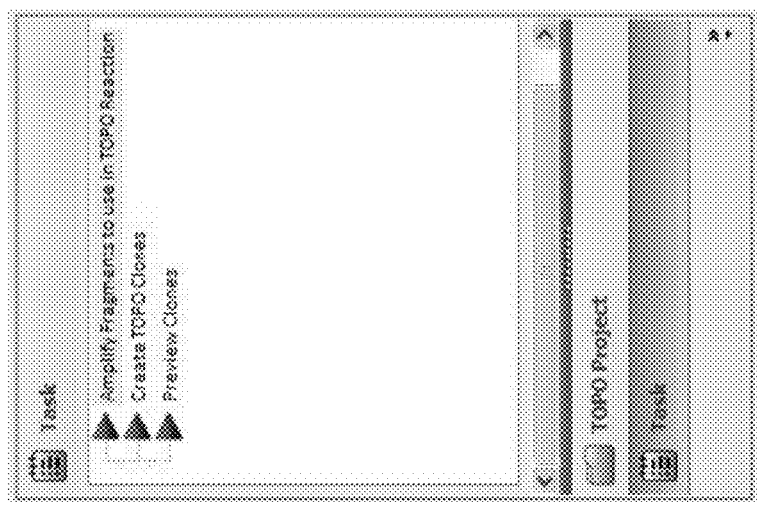
Figure 8A:
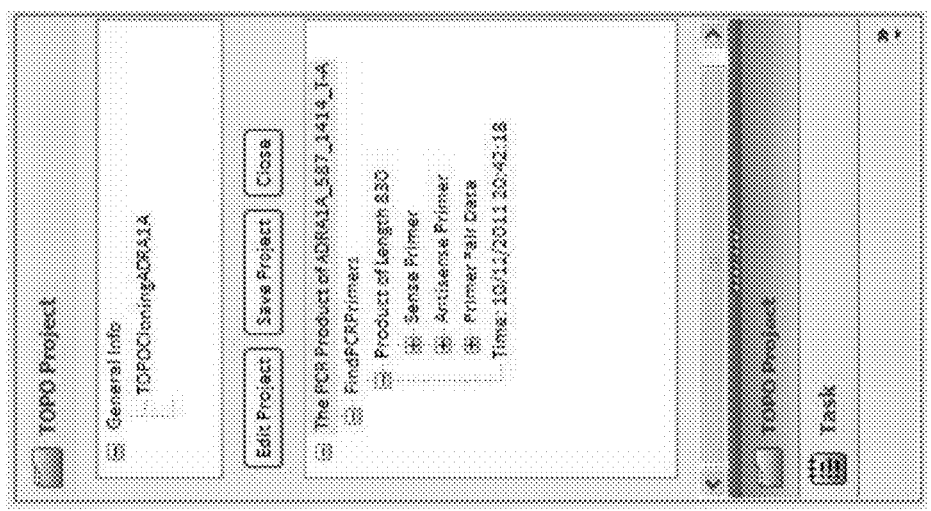

The Task List pane as depicted in FIG. 8B displays the list of tasks in the selected project. Clicking on the Task button to displays the list shown in FIG. 8B. As a user navigates through the TOPO® Cloning workflow, the Task List displays the current task, and allows a user to move between tasks by clicking on a different task.

Figure 8C:
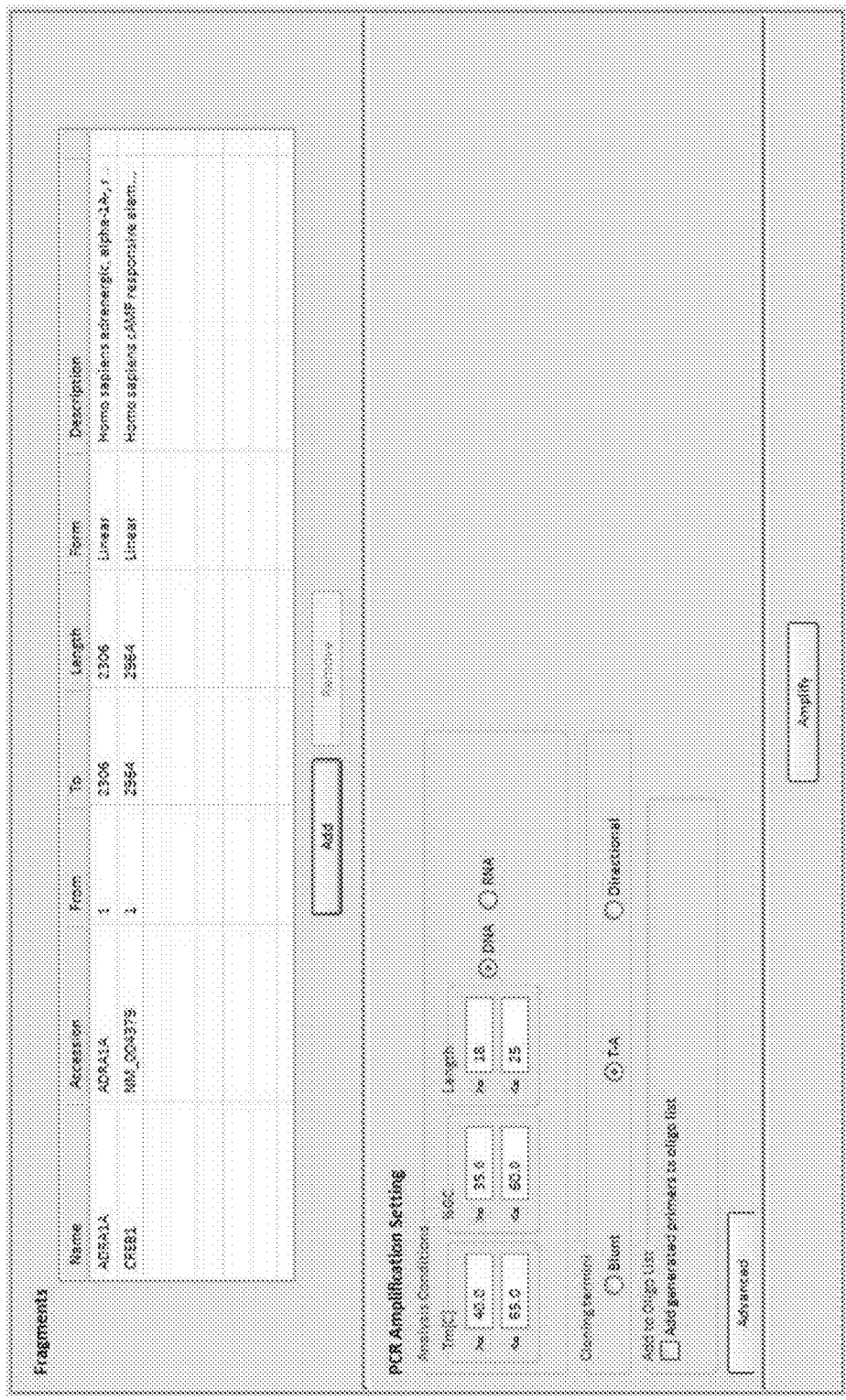

Current Task pane is depicted in FIG. 8C and displays the commands and settings for the currently selected task in the project. As a user navigates through the Task List workflow, the functions in this pane will change.

Figures 8D, 8E:
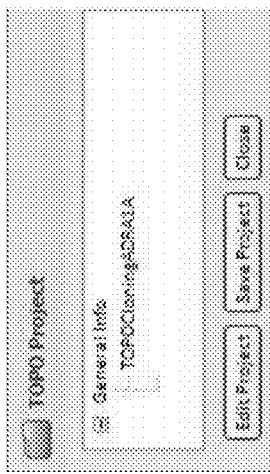

Create, save, and load projects are tools for saving, editing, and closing projects are located in the TOPO® Project pane which is depicted in FIG. 8D. To save a new TOPO® Cloning project, a user may click on Edit Project in the TOPO® Project pane. In the dialog, a user may enter a name and any description for the project. To save changes to a project, a user may click on the Save Project button. To close a project, click on the Close Project button. If there are unsaved changes, you will be prompted to save the project before closing.

To load an existing project, in Database Explorer, a user may navigate to the Projects list, as shown in FIG. 8E and open the Cloning Projects folder in the Local Database, and double-click on the TOPO® Cloning project in the list to open it.

The TOPO® Cloning workflow Task List displays the default TOPO® Cloning workflow and comprises as depicted in the prescribed workflow shown in FIG. 6 the following steps: 1) Amplify Fragments to Use in TOPO Reaction and 2) Create TOPO Clones.

This section describes each task in this prescribed workflow:

Amplify Fragments to Use in the TOPO Reaction pane as depicted in FIG. 8F depicts the Amplify Fragments to use in TOPO Reaction task which is the default task displayed when a user first open the TOPO® Cloning Tool. The first step in this task to select the fragment(s) a user want to amplify by PCR for use in a TOPO cloning reaction. These fragments will be listed in the Fragments list as shown in FIG. 8F.

Load molecules or fragments in the Fragments list: With a molecule open in Molecule Editor, right-click in the Graphics or Sequence pane a user may select Launch TOPO Cloning to load the entire sequence in the list. Alternatively a user may, with a molecule open in Molecule Editor, select a portion of the sequence in the Graphics or Sequence pane, right-click, and select Launch TOPO Cloning to load only that part of the sequence in the list. Yet alternatively, with the TOPO® Cloning window open, a user may ensure the Amplify Fragments to Use in TOPO Reaction task is selected and click on the Add button under Fragments to select a complete molecule from the database.

To change the regions to amplify in the selected molecules, a user may type a new range in the From and To fields in the Fragments to Amplify subpane. PCR Amplification Settings with the fragment(s) loaded, select the desired amplification settings under PCR Amplification Settings. The standard options are described in the Table below.

| Tm(C.) | Enter limits in degrees Celsius for primer melting temperature (Tm) (temperature at which 50% of primer is a duplex) and the difference between Tm for sense and antisense primers. |

| | |
|---|---|
| % GC | Enter limits in degrees Celsius for primer melting temperature (Tm) (temperature at which 50% of primer is a duplex) and the difference between Tm for sense and antisense primers. |
| Primer Length | Defaults to 20-25, recommended for TOPO ® Primers |
| DNA/RNA button | Select the type of nucleotide sequence. |
| Add generated primers to oligo list | Select this checkbox to add the primers a user can generate to the oligo list |

For additional amplification settings, a user may click on Advanced. The advanced amplification settings are identical for all PCR primers, and are similar to Primer Design described previously.

Figure 8G:
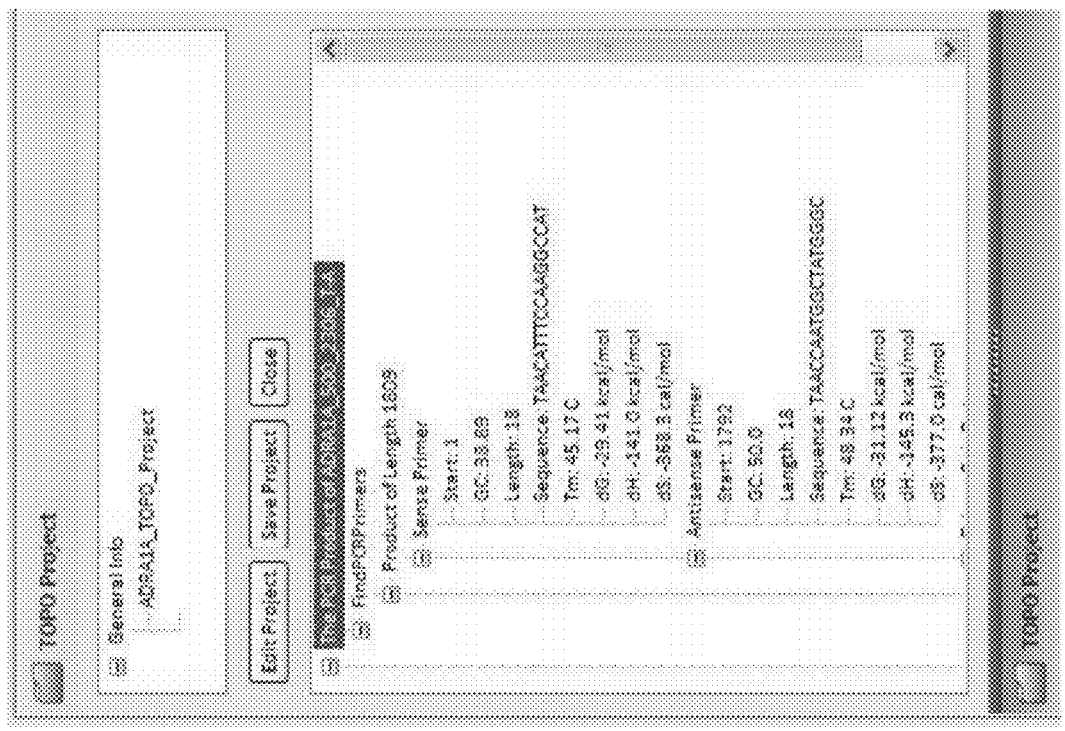

After making the selections as described above a user may click on the Amplify button. The next task pane will be displayed, and the generated PCR product(s) will appear listed in the Inserts subpane, and also listed in the TOPO® Project pane as depicted in FIG. 8G.

Figure 8H:
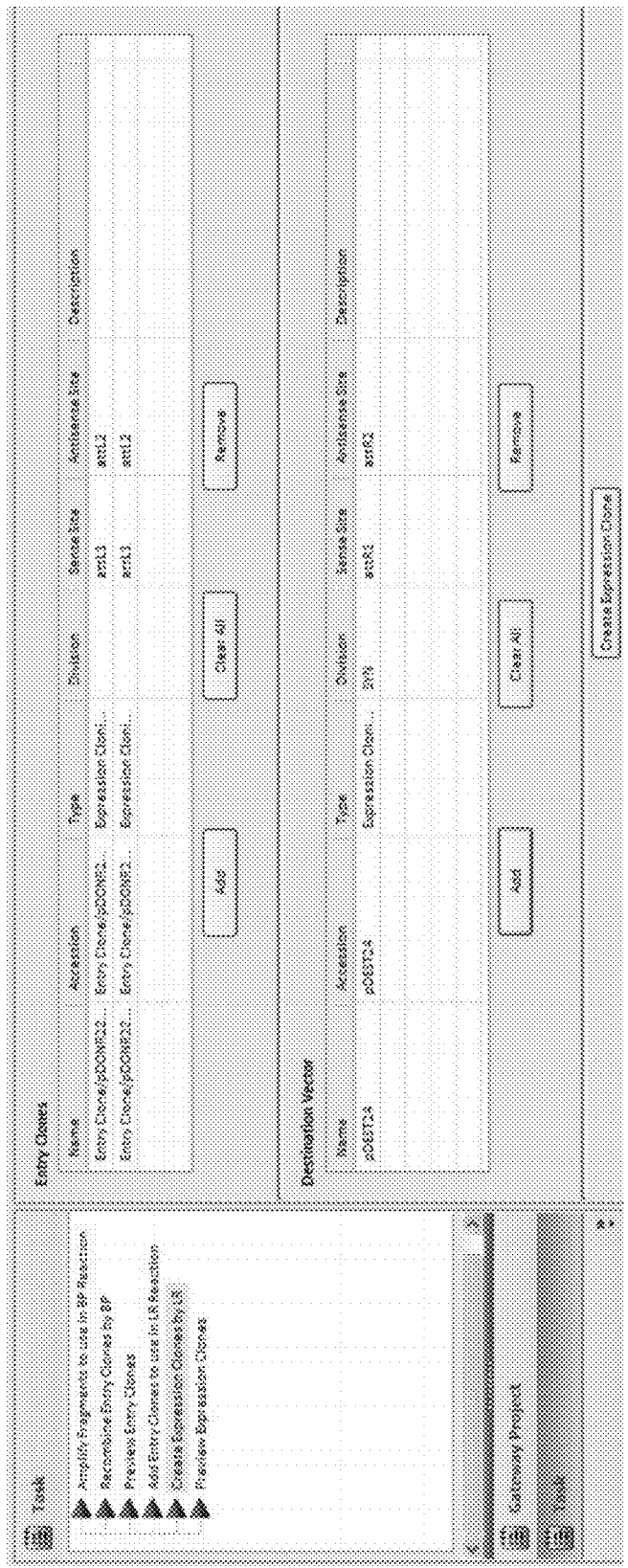

Create TOPO® Clones: In the Create TOPO® Clones task pane as shown in FIG. 8H, a user can modify the list of fragments and select a vector or vectors with which to create TOPO® clones Inserts: The fragments amplified are listed in the Inserts list at the top of the pane. To add a previously amplified fragment or a fragment designed with the necessary overhangs by another means, a user may click on the Add button and select the molecule from the database. To remove a molecule from list, a user may select it and click on Remove. To clear the entire list, a user may click on Clear All.

Vectors: To select a vector: A user may click on the Add button and select the vector from the database. To remove a vector from list, a user may select it and click on Remove Create the TOPO® Clone: when all selections have been made a user may click on Create TOPO® Clone. The Preview Clones task pane will open (not expressly depicted here).

Figure 9A:
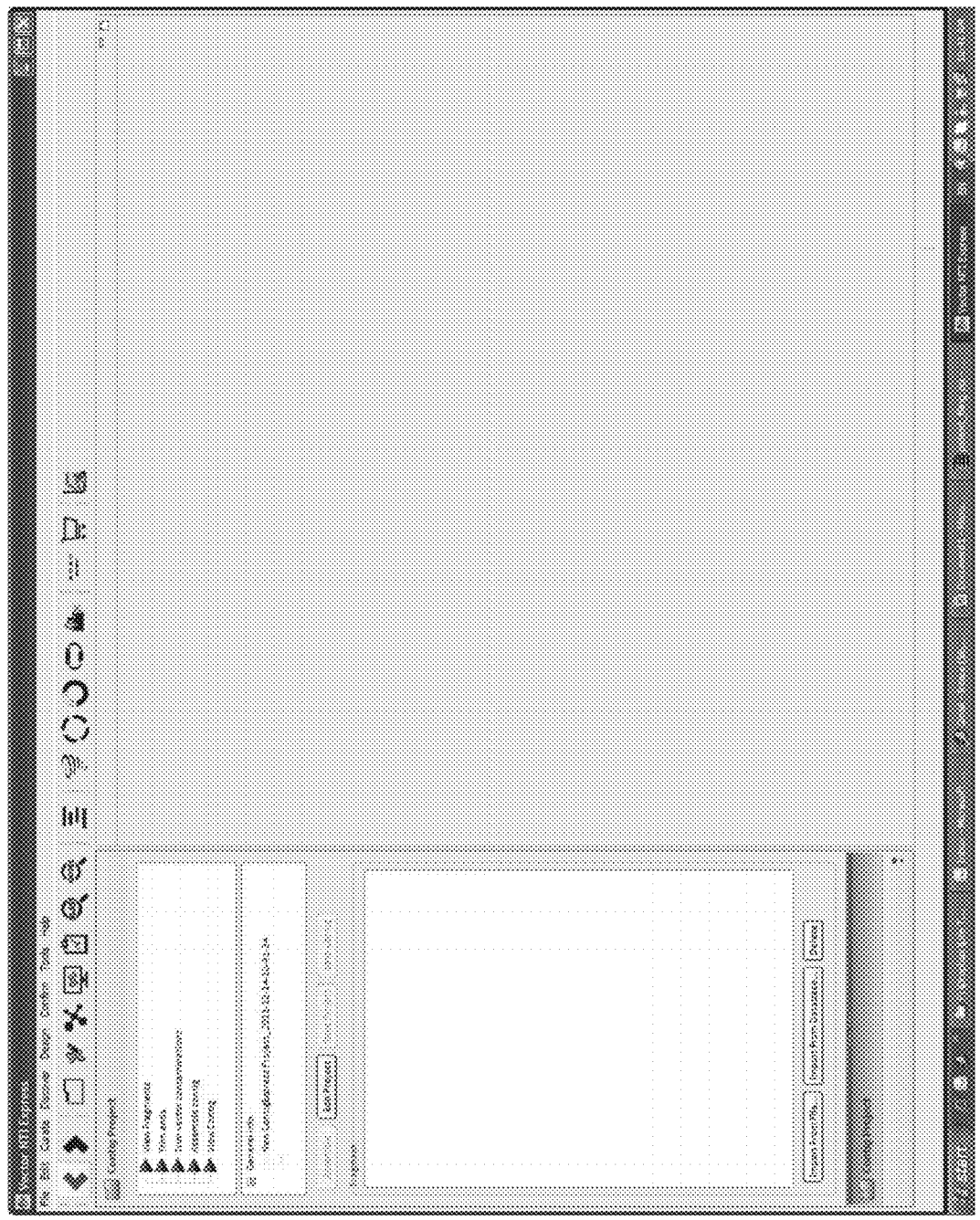

FIGS. 9A-9G depicts a prescribed workflow GUI describing the exemplary workflow shown in FIG. 10 relating to ContigExpress®=Accordingly a default display of all steps will appear upon launching ContigExpress®. Step 1 comprises Lauching Contig Express® which brings up the screen as shown in FIG. 9A which shows all the default steps (Subroutines) of ContigExpress prescribed workflow including 1. View Fragments 2. Trim ends 3. Trim vector contaminations 4. Assemble contig and 5. View contig as shown in the left navigation pane in FIG. 9A.

Figure 9B:
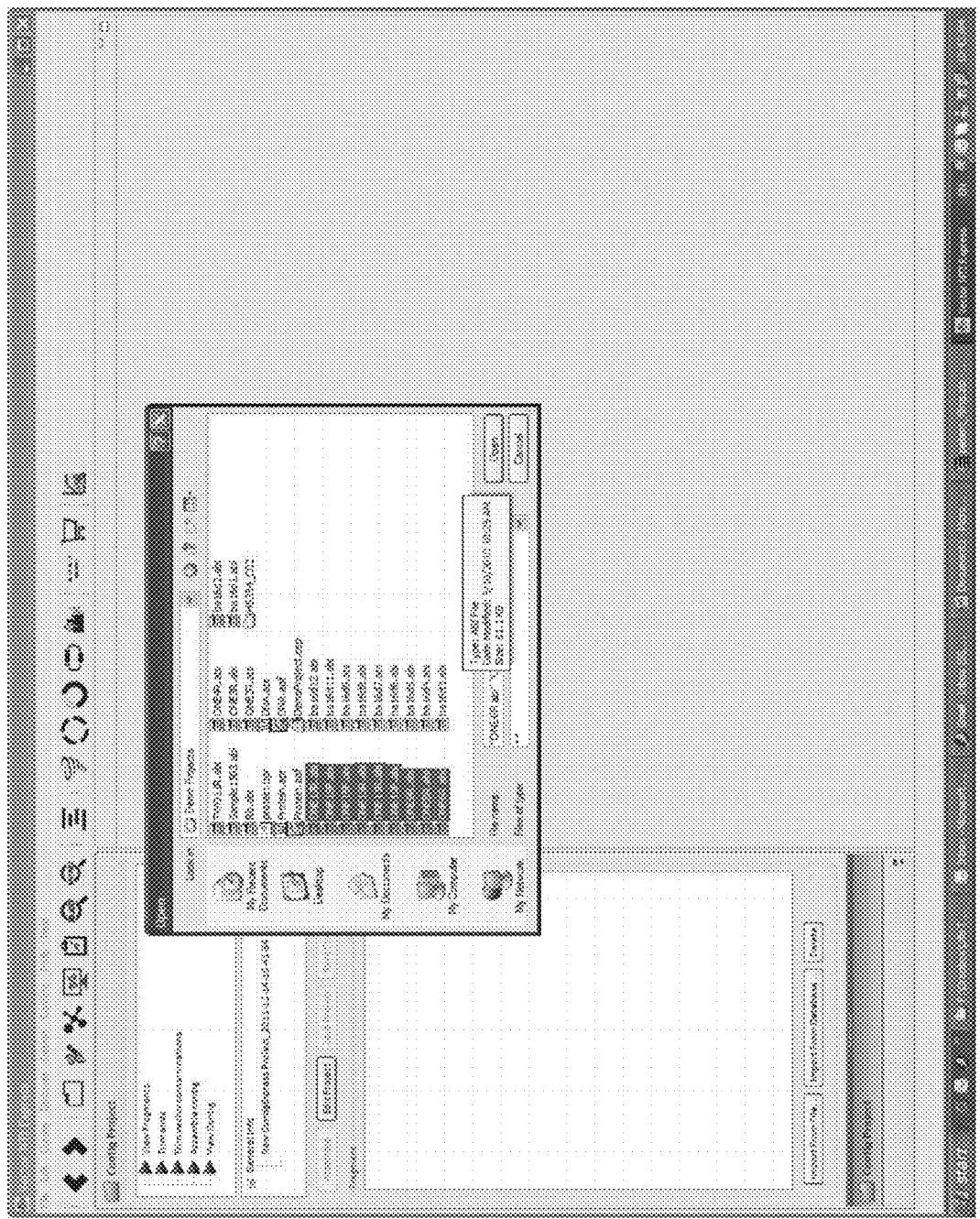
Figure 9C:
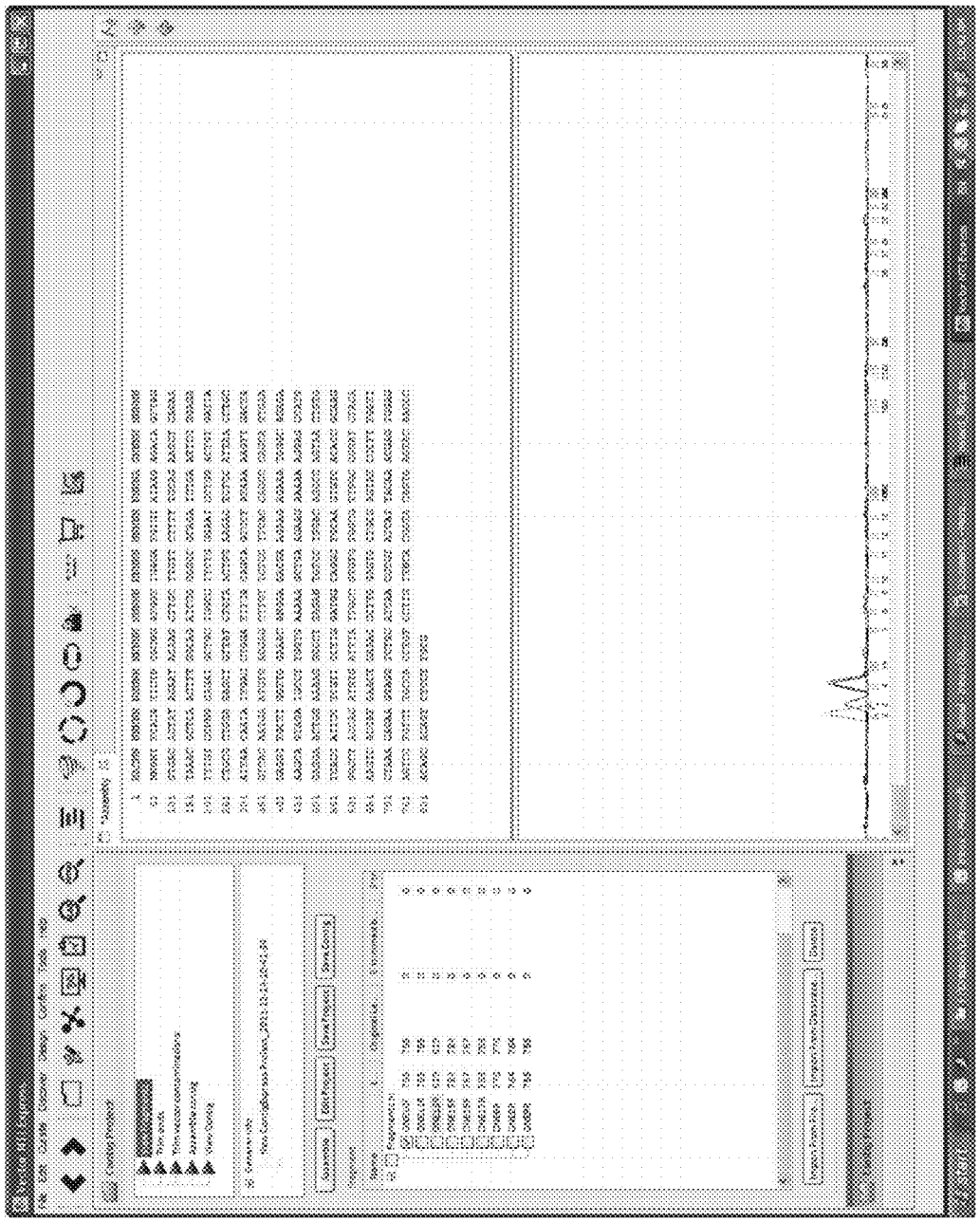
Figure 9D:
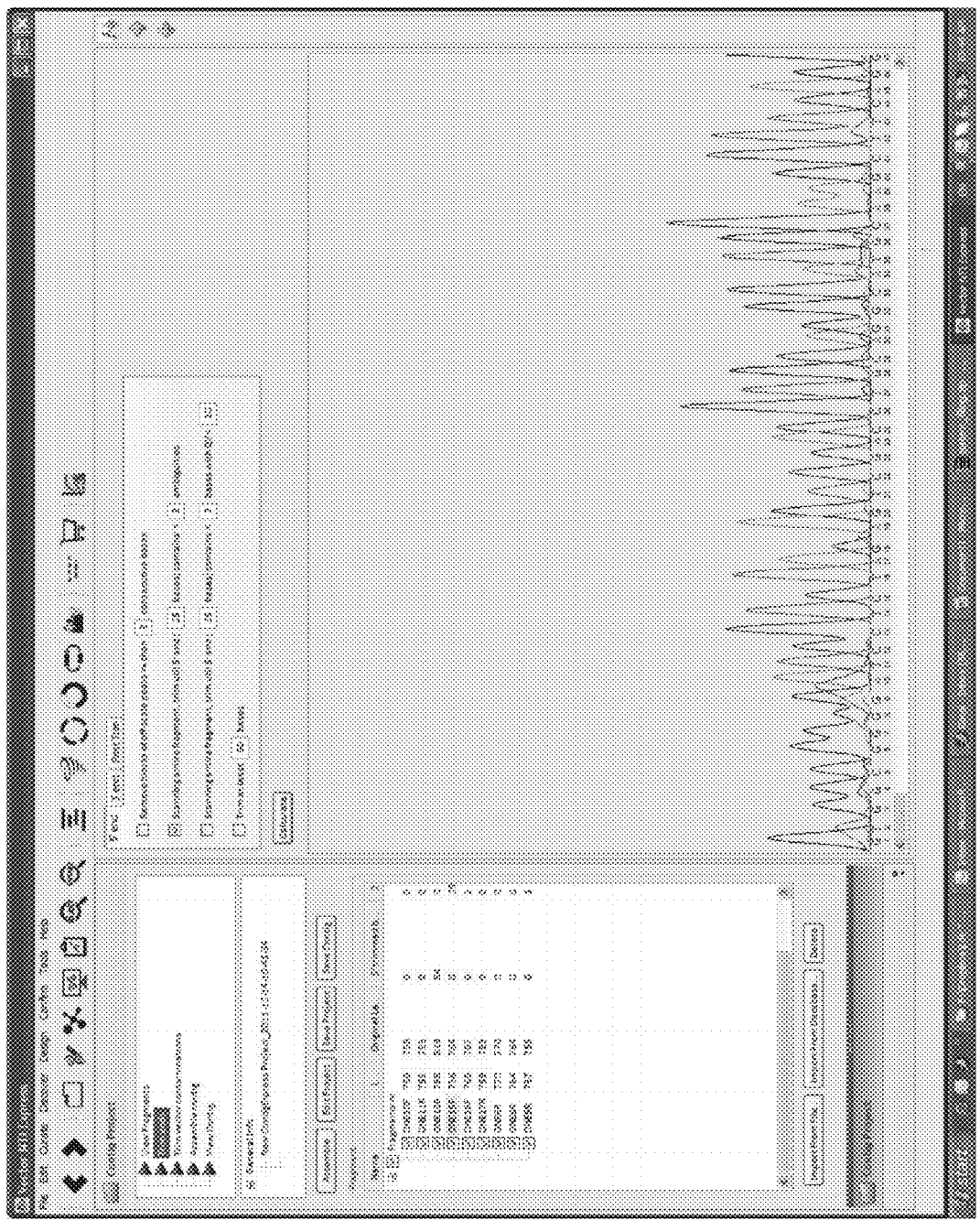
Figure 9E:
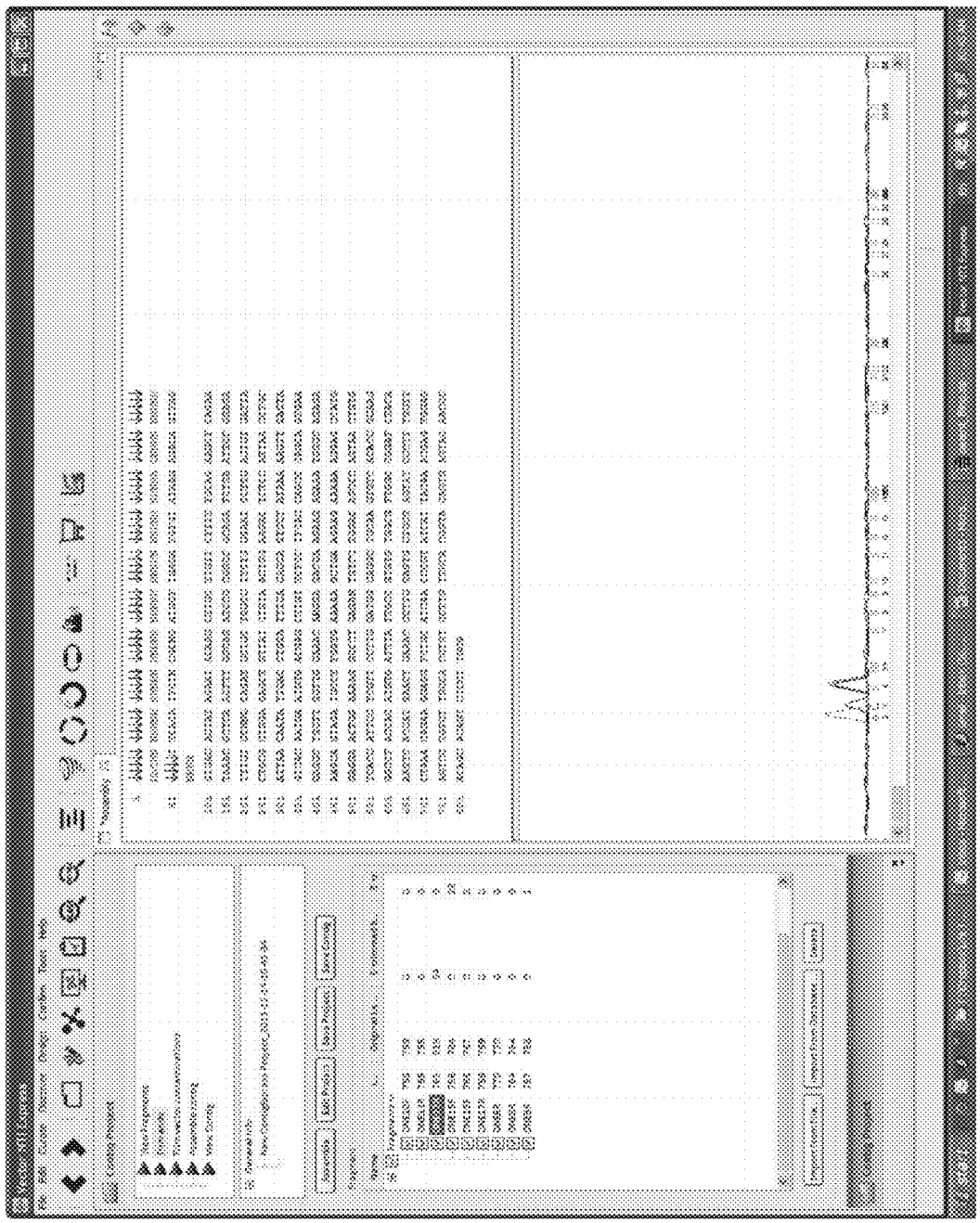
Figure 9F:
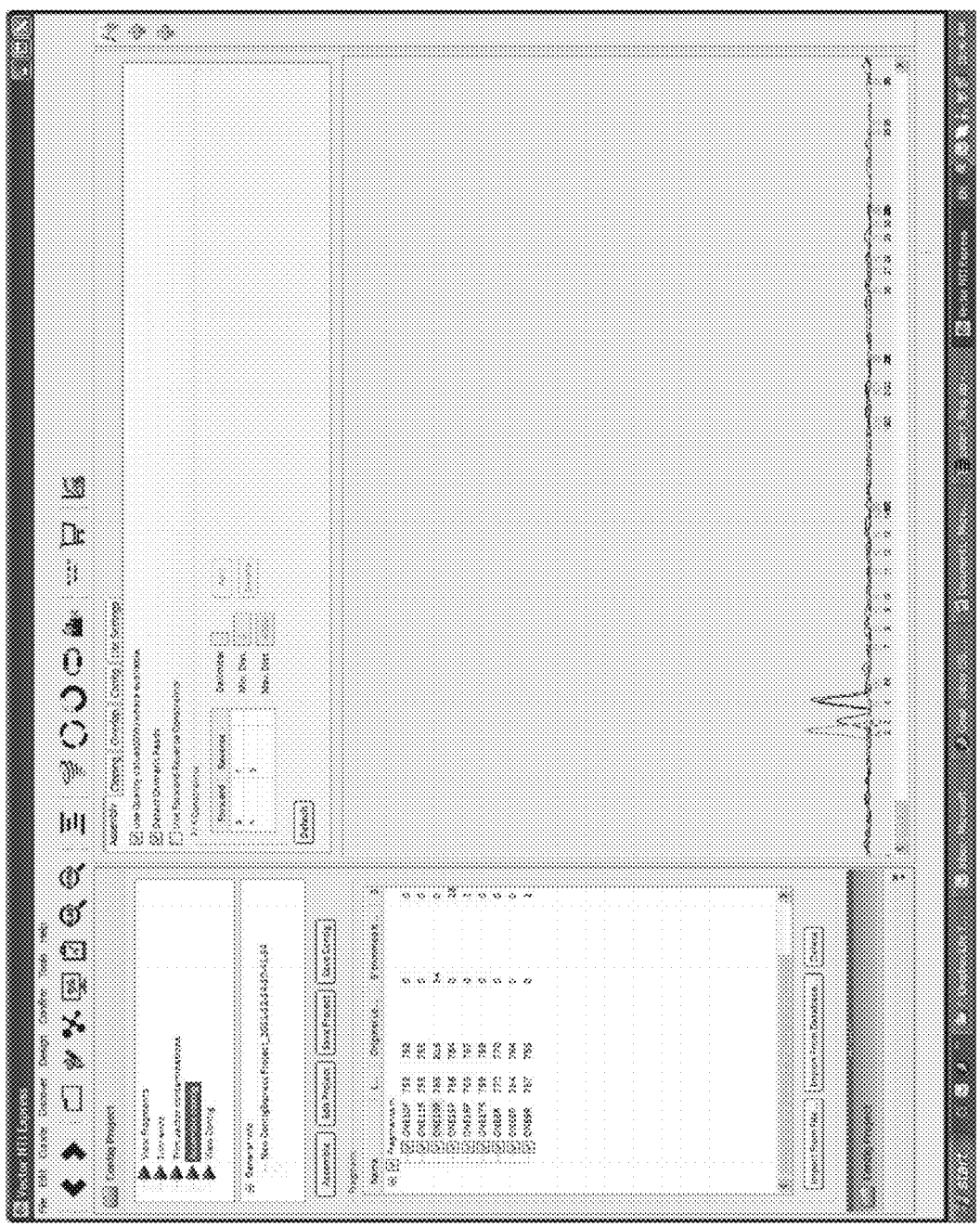
Figure 9G:
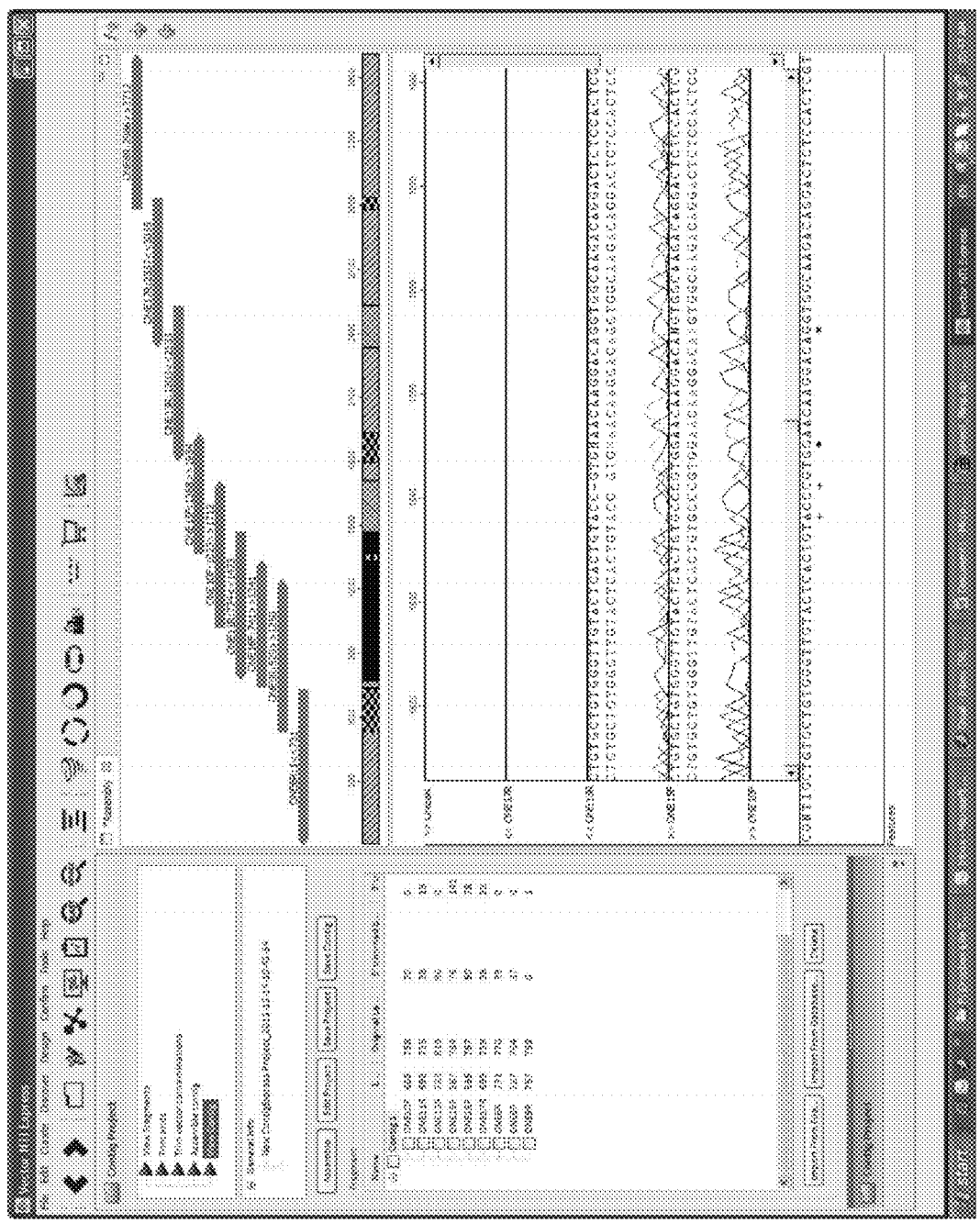

GUI of Step 2 is shown in FIG. 9B which shows Selecting ABI files from the file system Selecting the first subroutine of the prescribed workflow of View Fragments brings the GUI screen as shown in FIG. 9C. Selecting the second subroutine of the prescribed workflow of Trim Ends of all Fragments brings the GUI screen as shown in FIG. 9D. Selecting the third subroutine of the prescribed workflow of Trim Vector Contaminants brings the GUI screen as shown in FIG. 9E. Selecting the fourth subroutine of the prescribed workflow of Assemble Contig brings the GUI screen as shown in FIG. 9F. Selecting the fifth subroutine of the prescribed workflow of View Contig brings the GUI screen as shown in FIG. 9G.

In some embodiments, the disclosure describes an in silico method comprising a subsystem for the creation of a customized workflow of a biotechnology process. In some embodiments, creation of an in silico customized workflow may comprise: generation by a user of at least one method file in a computer system, the method file comprising, computer readable instructions of a plurality of steps of a biotechnological process, wherein the user inputs and/or selects a plurality of parameters associated with each step of the biotechnological process; and performing the biotechnological process comprising executing the at least one method file comprising computer readable instructions by the computer system to obtain at least one biotechnology product. In some embodiments of this method, the step of generation by a user of a method file comprising a plurality of steps may comprise generation of steps that may be in a sequential order or may alternatively comprise generation of steps that are not in any particular order. Typically, all the parameters associated with each step (ordered or random steps) of a method file are selected or inputted by a user prior to execution of the method file. In some embodiments, a navigation panel facilitates a user to input/select parameters associated with each step. In some embodiments, selection or input of user defined parameters in steps may be based on available tools and subsystems in a computer system. In some embodiments, one or more steps may involve inclusion of data which may be user input data. In some embodiments a step may involve pre-processing of data by the system.

In some examples, a user may use a basic prescribed workflow and customize it with user input of various parameters and/or values, save such a workflow as a customized prescribed workflow of the disclosure. A user may save a workflow (prescribed or customized) locally such as on a local hard-drive, a floppy disk, a USB stick, in a .txt file, in an .html format, and/or even be able to send the saved protocol via email.

Prescribed and customized workflows of the disclosure also allow user to analyze an in silico method and steps thereof, wherein the analyzing is executed by the computer system. In some embodiments an in silico method of the disclosure may further comprise generating reports of the workflow wherein the generating reports is executed by the computer system. In some embodiments, reports may be generated based on analysis of the steps customized by a user.

In some embodiments, the disclosure describes in silico methods comprising a subsystem for tracking the progress of a biotechnology process. In some embodiments tracking progress of a biotechnology process may comprise user navigation during the execution of a workflow.

In some embodiments, the present disclosure describes in silico methods for a biotechnology process for achieving an optimal end result. Accordingly a user may change/customize one or more steps parameters using a GUI to input user selections or data and arrive at an optimized procedure for a biotechnology process. In some embodiments, a user may check the in silico method by performing experiments in the lab. The ability to save each parameter change as a separate in silico method enables a user to review results of each method and arrive at an optimum method.

Some non limiting examples of applications of the in silico methods of the disclosure may be to provide other non-skilled users an optimized in silico procedure for a biotechnology process; to provide one standardized customized method to different users to perform similar biotechnology processes to provide a consistent workflow across diverse users; to provide a method whereby one parameter at a time may be varied to arrive at an efficient method.

In some embodiments, an in silico method of the disclosure may comprise combining a plurality of workflows (prescribed or customized) to arrive at custom production workflow. Accordingly, several individual workflow protocols may be combined to consistently produce a biotechnology product, wherein the end product of one workflow (of the plurality of workflows) may for example be used as a start product for another workflow. In a non-limiting example an in silico workflow for making a modified host system in silico may comprise combining at least one workflow for cloning; at least one workflow for making a vector; at least one workflow for selection to arrive at a modified host system expressing a gene of interest.

It will be understood by one of ordinary skill in the relevant arts that other suitable modifications and adaptations to the methods and applications described herein are readily apparent from the description of the invention contained herein in view of information known to the ordinarily skilled artisan, and may be made without departing from the scope of the invention or any embodiment thereof.

EXAMPLE 1

The following example illustrates one specific aspect of the methods and computer systems of the invention.

Overview of VectorDesigner

VectorDesigner is a secure, online tool for clone construction and management. Using VectorDesigner, you can import, view, construct, analyze, and save DNA and protein sequences in a Web-based environment, and then export your molecule constructions as standalone files to share with colleagues.

VectorDesigner provides a secure Web-based database for storage and management of your clone sequences and designs. It includes interactive tools for identifying ORFs and restriction sites, translating sequences, generating PCR primer designs, searching public sequence databases, and performing other types of molecule analysis. You can design complex cloning experiments using proprietary Gateway® and TOPO® technologies or common methodologies such as restriction-ligation and PCR. You can analyze your sequences using other Invitrogen tools (BLOCK-iT™ RNAi Designer, CloneRanger™, OligoPerfect™ Designer, LUX™ Designer) and import the results back into VectorDesigner.

VectorDesigner is based on Vector NTI Advance™, a software suite for sequence analysis and molecular data management, available for Windows® and Macintosh® operating systems. Files created and saved using VectorDesigner can be opened seamlessly in Vector NTI Advance™, which provides more powerful analysis tools and enhanced databasing capabilities. See FIG. 5 for a comparison of the functionalities of VectorDesigner™ and Vector NTI Advance™. See also, Invitrogen's Bioinformatics Software Web page for more information about Vector NTI Advance™

Database Operations VectorDesigner Database Browser

The VectorDesigner database contains DNA, RNA, and protein molecule files in a hierarchy of folders and subfolders. The Database Browser provides access to the entire contents of the database.

Click on the Browse Database tab in VectorDesigner to view the Database Browser. The Browser window is divided into two main panes: the "Folder tree" and the "Molecules list".

The Folder tree displays the database folder structure. Use the folder tree to navigate through the database. Click on a folder name to view its contents. Click on the .+−.button next to each folder name to expand or collapse the folder.

Note: The Folder tree is only visible if you approved the signed security certificate when VectorDesigner first opens.

The Molecules list displays the contents of the currently selected folder. Click on a molecule name in the list to open the molecule file. Select the checkbox next to the molecule name to rename, move, or delete the molecule file. Click on the Import button to enter a new molecule sequence or import a molecule file from another source.

Database Folders

The Database Browser window displays the folder structure of the VectorDesigner database. The database has five main folders—three user folders (DNA/RNAs, Proteins, and Primers) and two read-only folders (Invitrogen Vectors and Examples)

User Folders

User folders are private, secure folders that contain molecule files that you create or modify (e.g., DNA/RNAs; Proteins; Primers). The contents of these folders are created and controlled by the user, are keyed to your user name and password, and cannot be viewed by other users. The molecule files in these folders can be edited, renamed, deleted, moved, and exported for collaboration with other users.

You can create new folders within the three main user folders. However, you cannot delete or move the three main user folders, and you cannot add new main user folders.

Each main user folder can contain only molecules of the specified type (DNA/RNAs, Proteins, and Primers). For example, you cannot store DNA molecule files in the Proteins folder.

Read-Only Folders

Read-only folders contain molecule files created by Invitrogen: Invitrogen Vectors, which contains sequences and maps of vectors sold by Invitrogen, including Gateway® and TOPO® vectors; and Examples, which contains sequence-verified example files of common DNA, protein, and primer molecules. These folders and files cannot be modified or deleted and are accessible to all users. You can copy the molecule files in these folders into your private user folders and edit them.

Editing Folders

You can add folders within the main user folders. Click on a folder name to select it and click on the Create a New Folder button to create a subfolder within that folder. To delete a folder that you created, click on the folder name to select it and click on the Delete Folder button. Note: Deleting a folder will also delete all its contents.

You can rename the main user folders or any of their subfolders. Click on the folder to select it, and click on the Rename Folder button. Enter the new name in the pop-up box and click on OK. Note that renaming a user folder will not change the file type restriction for that folder.

Folder Restrictions

User folders have the following restrictions: The DNA/RNAs folder and Proteins folder can contain up to 100 molecules each; The Primers folder can contain up to 1,000 molecules. DNA and protein molecules are restricted to 350,000 base pairs or amino acids in length; Primers are restricted to 250 bases in length; Each folder can contain only molecules of the specified type (e.g., you cannot store DNA molecule files in the Proteins folder); Each main user folder can have only 10 subfolders; Molecules with the same name cannot be saved in the same folder.

Database Capacity

The VectorDesigner database has the following limits: The DNA/RNAs folder and Proteins folder can contain up to 100 molecules each; The Primers folder can contain up to 1,000 molecules; DNA and protein molecules are restricted to 350,000 base pairs or amino acids in length; Primers may be restricted in size (e.g., 250 bases in length).

Molecule Files

A molecule file contains all the information about a molecule, including sequence, name, description, features, references, comments, analysis, etc. Molecule files for DNA/RNA and protein molecules are based on the GenBank/GenPept format, which is an ASCII text-based format, and can be exported as stand-alone files in a variety of formats.

Molecule files that are created, imported, or modified by you are stored in private user folders in the database and are accessible using your user name and password. Example molecule files created by Invitrogen are stored in read-only folders (Invitrogen Vectors and Examples) and are viewable by everyone.

The Database Browser window provides access to all the molecule files in the database. Using the Browser, you can open, rename, move, delete, import, and export the molecule files in your user folders, and you can export molecule files in the read-only folders. Molecule File Types Molecule files in VectorDesigner can contain DNA or RNA sequences, protein sequences, or primer sequences. The type of molecule determines the information contained in the molecule file, which user folder it is stored in, and which viewer it is displayed in. DNA and RNA Molecule Files contain circular or linear nucleotide sequences, are stored in the DNA/RNAs folder in the database, and are displayed in the Molecule Viewer. Protein Molecule Files contain amino acid sequences, are stored in the Proteins folder in the database, and are displayed in the Molecule Viewer. Primer Files contain DNA or RNA primer sequences, are stored in the Primers folder in the database, and are displayed in the Edit Primer Properties window.

Molecule Files in the Database Browser: Molecule files are listed in the right pane of the Database Browser window. Click on a folder name in the Browser to display the molecule files in that folder. If you make changes to the molecules list in the Browser and those changes are not updated in the Browser window, click on the Reload button to refresh the list. If you have more than 50 molecules in the list, use the scroll buttons to scroll through the list.

Opening Molecules

To open a molecule file: 1. Navigate to the appropriate folder in the Database Browser; and 2. Click on the molecule name in the molecules list. For DNA/RNA and protein molecules, the Molecule Viewer window for that molecule will open. For primers, the Edit Primer Properties window will open.

Saving Molecules

You can save changes that you make to molecule files. Changes to molecules opened from read-only folders must be saved under a different file name in your private user folders. Unsaved DNA/RNA/protein molecules are flagged with a "*" in the Molecule Viewer title bar.

Saving DNA/RNA and Protein Molecules

To save a DNA/RNA or protein molecule in the Molecule Viewer, go the Molecule menu and select Save or click on the Save button on the main toolbar. To save a molecule with a different file name or in a different location, go the Molecule menu and select Save As or click on the Save As button on the main toolbar. The Save As dialog will open. In the dialog, rename the file and/or select or create a new folder to save it in.

Saving Primer Molecules To save a standalone primer file, in the Edit Primer Properties dialog, select the Rename or the Overwrite option button, and click on Save. If you selected Rename, the primer file will be automatically saved with a numerical extension appended to the file name (e.g., a file named Primer will saved as Primer (1)).

Importing Molecules

You can import molecule and primer sequences and other information into VectorDesigner in a variety of file formats, including: GenBank/GenPept; EMBL; SWISS-PROT; Vector NTI® (uses the GenBank format); FASTA; Plain text.

Exporting Molecules

You can export molecules from VectorDesigner in a variety of file formats. You can export the data for one or more molecules at a time from the Database Browser, or you can export the data for the current molecule loaded in the Molecule Viewer. You can export one or more molecules from the Database Browser to a file (text format) or to a browser window (HTML format). You can export the data for a DNA, RNA, or protein molecule displayed in the Molecule Viewer to a variety of formats.

Export to Vector NTIO

You can export the molecule data from VectorDesigner to Vector NTI®. In the Molecule Viewer window, click on the Export to Vector NTI button on the main toolbar or select the command from the Molecule menu.

You will be prompted to save the file (.gb extension for DNA/RNA files, .gp extension for protein files) or automatically launch Vector NTI® and display the molecule in the application window. Note that Vector NTI® software must be installed on your computer to automatically launch the application.

Export to GIF

You can export the molecule image as it is displayed in the Molecule Viewer as a GIF image. Note: This command will export only the current view of the molecule. If the displayed information (sequence, graphics, text, etc.) is cut off at the margins of the panes in the Molecule Viewer, the data will appear cut off in the resulting image. Be sure to configure your Molecule Viewer panes as desired for the resulting image.

Export Format

The exported information will vary depending on the export format you select. Each database format (GenBank, EMBL, Vector NTI®, etc.) will include formatting and information compatible with that database. All formats include the molecule sequence. The available formats are: DNA/RNA molecules—GenBank, EMBL, and FASTA; Proteins—GenPept, Protein FASTA, SWISS-PROT; Primers—GenBank, EMBL, FASTA, and Tab-Delimited Moving Molecules To move one or more molecule files the user can (1) Navigate to the appropriate user folder in the Database Browser; (2) Select the checkbox(es) next to the molecule name(s); (2) Click on the Move button; and (3) In the Pick a Folder window, navigate to the desired folder and click on OK. You can only move molecule files within the same main user folder. For example, you cannot move DNA molecule files into the Proteins folder. Molecules with the same name must be stored in separate folders.

Deleting Molecules

You can delete molecule files from the user folders of the VectorDesigner database. Note that deleted molecule files cannot be recovered from the database, and you will be prompted to confirm the deletion. To delete one or more molecule files the user can (1) Navigate to the appropriate user folder in the Database Browser; (2) Select the checkbox(es) next to the molecule name(s); (3) Click on the Delete button; (4) Click on OK to confirm the deletion.

Creating New Molecules

You can create a new molecule based on the molecule currently displayed in the Molecule Viewer. You can create a new molecule from a selected area of the existing molecule, such as a restriction fragment, or from the whole molecule.

For DNA or RNA molecules, you can create DNA/RNA molecules that are the reverse complement of the existing molecule or you can create protein molecules from a translation of the sequence. In the Molecule Viewer, click on the Create New Molecule button on the main toolbar or select the command from the Molecule menu. In the dialog, enter a name for the new molecule in the Name field, and a description (if any) in the Description field. Next, specify which part of the existing molecule to use as the basis for the new molecule. If you selected or marked a region of the existing molecule before you opened the dialog, the Selection or Mark options will be available and selected. Otherwise, select Molecule to select the whole molecule or Specified Range to enter the sequence range in the From and To fields. DNA/RNA molecules only: Select the Reverse Complement checkbox to create a molecule from the complementary sequence. Select Translate to create a protein molecule from a translation of the sequence. When you have made your selections, click on OK. The new molecule will be created and displayed in a new Molecule Viewer window.

Renaming Molecules

You can rename the molecule files in the user folders of the VectorDesigner database. To rename a molecule file: Navigate to the appropriate user folder in the Database Browser; Select the checkbox next to the molecule name in the molecules list; Click on the Rename button; Enter the new file name in the pop-up window and click on OK.

Revert Changes

You can undo all changes that you have made to a DNA/RNA molecule since it was last saved. Go to the Molecule menu and select Revert Changes to execute this command.

Molecule Viewer

The Molecule Viewer displays all the information in the database for DNA/RNA molecules and protein molecules. (Information for primers is displayed in the Edit Primer Properties dialog.) When you open a DNA/RNA or protein molecule file from the Database Browser, the Molecule Viewer will launch and display the molecule.

The Molecule Viewer can display: The molecule sequence; A graphical representation of the molecule; Information about the molecule, including a list of molecule features; The results of analysis performed on the molecule.

The Viewer can be divided into three main panes, the Text Pane, the Graphics Pane, and the Sequence Pane, each with its own set of tools and resources. The Text Pane provides database information about the molecule, including a molecule description, and list of molecule features, database keywords for the molecule, references to literature/other materials, links to resources related to the molecule, fields for user comments, and information about any analysis performed on the molecule (restriction sites, primer designs, etc.). The Graphics Pane displays a feature map of the molecule, and includes interactive tools for adding and editing features, highlighting and marking areas of the sequence, and displaying the molecule. An Analysis Pane can also be displayed in the Graphics Pane.

The Sequence Pane displays the entire nucleotide/amino acid sequence, and includes interactive tools for editing and marking the sequence, adding features, rearranging sequence elements, and copying and pasting the sequence. In this pane you can also toggle between a view of the sequence and a detailed view of the molecule feature list. A Feature List can also be displayed in the Sequence Pane.

The Text Pane in the Molecule Viewer contains textual information about the molecule, including a general description, comments, references, descriptions of molecule features, and the results of any analysis. To change the molecule description, comments, associated genes, keywords, references, etc. in the Text Pane, use the Molecule Properties dialog.

The Text Pane is structured as a directory tree. Click on the .+-.buttons to expand or collapse the branches of the tree. Alternatively, right-click on the branch and select Expand Branch or Collapse Branch.

Copying Text: To copy and paste text from the Text Pane: Click on the branch or feature that you want to copy. To select multiple branches/features, use Shift-Click or Control-Shift key commands To select all branches and features, right-click anywhere in the Text Pane and select Select AH. Next, right-click on the selection and select Copy Text. The text will be copied to the computer clipboard. Paste the text into the application of your choice.

Link Mode

You can link the display in the Graphics and Sequence Panes to the folders that are open in the Text Pane control using the Link Mode command When linked, information from the open folders in the Text Pane is displayed in the Graphics and Sequence Panes, while information in closed folders is not displayed. (Note that the molecule name and length is always displayed in the Graphics and Sequence Panes.)

Protein Parameters (Protein Molecules Only)

The Text Pane for protein molecules includes a table of Protein Parameters, which lists some of the biochemical properties of the protein, such as molecular weight, A280 absorbance, isoelectric point, etc. These properties are automatically calculated by VectorDesigner from the amino acid sequence.

Graphics Pane

The Graphics Pane in the Molecule Viewer contains a graphical representation of the DNA, RNA, or protein molecule, highlighting the results of any analyses such as ORFs, restriction sites, and other defined features. It includes a toolbar below the pane. Additional tools are located on the View menu and on the context menu if you right-click in the Graphics Pane. Defined features in the molecule are shown as colored bars in the Graphics Pane. Directional features (such as coding DNA sequences, or CDSs) are shown as bars with directional arrows. Open reading frames are shown as thin directional arrows. Restriction endonuclease sites are labeled with the name of the enzyme.

Circular and Linear Display of DNA/RNA Molecules

For circular DNA/RNA molecules (as defined in the Molecule Properties dialog), you can toggle between a circular and linear display. Click on the Display as Circular button or the Display as Linear button below the Graphics Pane, or select the commands from the View Graphics Map submenu.

Note that this only changes the molecule display. To change the actual molecule structure from circular to linear or vice versa, use the Molecule Properties dialog.

Showing Labels

To show and hide labels in the Graphics Pane, click on the Show/Hide Labels button below the Graphics Pane, or select the command from the View>Graphics Map submenu. For molecules with more than 80 features, labels are hidden by default.

Link Mode

You can link the display of features (including ORFS, restriction sites, etc.) in the Graphics Pane to folders that are open in the Text Pane using the Link Mode command. When linked, features of open folders in the Text Pane are displayed in the Graphics Pane, while features in closed folders are not displayed.

Standard Arrangement

If you change the displayed labels and features in the Graphics Pane (e.g., using Link Mode), you can reconfigure the pane to make best use of the available space. Go to the View Graphics Map submenu and select Standard Arrangement.

Sequence Pane

The Sequence Pane in the Molecule Viewer shows the sequence of a DNA/RNA or protein molecule in a scrollable, wrap-around field, with the starting base/amino acid number of each line shown to the left. The Sequence Pane uses standard code letters to indicate the bases/amino acids in the sequence. For DNA molecules, by default, both the direct and complementary strands are shown. (See Changing the Sequence Display, below.) Hold your cursor over the sequence to display a popup box showing the base/amino acid number at that point in the sequence.

The Feature List is also displayed in the Sequence Pane. Click on the Feature List button to the left of the Sequence Pane to view the Feature List. Click on the Sequence Pane button to return to a view of the sequence.

To change how the sequence is displayed in the pane, right-click in the Sequence Pane and select Sequence Properties. Various sequence and feature representation styles are available. In the Sequence Properties dialog, you can select the following display options:

Types Filter

To filter the types of features highlighted in the Sequence Pane, right-click in the pane and select Types Filter. In the dialog, all available features will be selected. Deselect the checkboxes next to the filters that you do not want to view in the Sequence Pane, and click on OK to make the changes.

Link Mode

You can link the display of features (including ORFs, restriction sites, etc.) in the Sequence Pane to the folders that are open in the Text Pane using the Link Mode command When linked, features of open folders in the Text Pane are displayed in the Sequence Pane, while features in closed folders are not displayed. To enable this feature, click on the Link Mode button on the main toolbar or select the command from the View menu.

Analysis Pane

The Analysis Pane displays graphical plots of a variety of a DNA and protein sequence analyses. You can display multiple plots at a time in the Analysis Pane. The available analyses depend on the molecule type (DNA/RNA or protein).

The Analysis Pane and the Graphics Pane are displayed in the same pane in the Molecule Viewer. The Graphics Pane is displayed by default. To display the Analysis Pane, click on the Analysis Pane button below the Graphics Pane. To return to a view of the Graphics Pane, click on the Graphics-Pane button.

Graph Format

The graphs in the Analysis Pane display different physiochemical properties of the sequence. Many of properties are based on parameters like charge that exert effects over distance. Other properties represented in the plot depend on the way adjacent bases/amino acids fold in 3-dimensional space, which is a function of the sequence itself.

The vertical (Y) axis in the graph shows the values of the analysis results; the horizontal (X) axis displays either numerical positions in the sequence or residues. At any point along the sequence, the Y value is derived not just from the specific residue at that point but also from adjacent residues. Each analysis algorithm uses an optimum window of adjacent residues to calculate the value for a point. You can adjust this window size in the Plot Properties dialog (see below).

Note: No values may be calculated at the beginning and end of the sequence if there are not enough bases/amino acids to the left or right of each base/amino acid for the algorithm to calculate a value. To calculate values for those regions, you can reduce the window size in the Plot Properties dialog. Plots Setup Use the Plots Setup dialog to select and arrange the analysis graphs to display in the pane. To open the dialog, click on the Plots Setup button below the Analysis Pane or select the command from the right-click menu.

In the Plots Setup dialog, the available analyses are listed in the top window and the selected graphs are listed in the bottom window. Analysis graphs are displayed in panels. You can add one or more analyses to a panel, and display multiple panels in the Analysis Pane.

Plot Properties

The Plot Properties dialog controls how each plot is displayed in the graph. To open the dialog, right-click on an graph in the Analysis Pane and select Plot Properties. The dialog is divided into three tabs. When you have made your selections, click on OK.

Diagram Tab

Click on the Graph Color button to open a dialog in which you can select a plot color and/or adjust the Red-Green-Blue (RGB) values of the color. Select the Draw Type from the dropdown list. Min-Max-Average displays the calculated minimum, maximum, and average values over each analysis region within the sequence as levels of shading along the line of the graph.

Under Preprocess Type, select Linear Interpolation to provide a linear interpolation of the graph line, or No Preprocessing to display the line without interpolation.

Params Tab

Window Size is the size of the processing "window" used to scan the sequence for analysis. Enter a number of bases/amino acids in the Window Size field (see example below). Step Size is the number of bases/amino acids in a sequence that constitute an analysis point in the plot. Enter number of bases/amino acids in the Step Size field (see example below). Example: If you select a % GC Content analysis with a window size of 21 and a step size of 1, the GC content percentage will be calculated for a 21-base region centered on each base in the sequence (10 bases on either side of the base). A step size of 5 would calculate the percentage for a 21-base region centered on each 5-base region in the sequence.

Info Tab

This tab provides information on the type of analysis in the plot, including any references to external literature.

Feature List

The Feature List is list of the defined features in the molecule in an easy-to-read table format.

The Feature List is displayed in the Sequence Pane. Click on the Feature List button (Efs) to the left of the Sequence Pane to view the Feature List. Click on the Sequence Pane button (|i|c<|) to return to a view of the sequence. Click on a column header in the Feature List table to sort the list by that column. Right-click on a feature in the list and select Edit Feature Properties to open the Add/Edit Feature dialog. Right-click on a feature in the list and select Copy Text to copy the feature information to the computer clipboard in a tab-delimited format. Right-click on a feature in the list and select Open Link to access a variety of links to online databases with information about the feature. Note that links are available for only certain types of imported molecules.

Window Manager

Use the Window Manager dialog to switch between multiple open Molecule Viewer windows. To open the Windows Manager, go the Windows menu and select Windows.

All open Molecule Viewer windows will be listed in the dialog. To bring a window to the front, double-click on it in the list. To close a window, select it in the list and click on Close Windows. To close multiple windows, select them using Control+Click and Shift+Click key commands and click on Close Windows. Click on Exit to close the manager.

Molecule Features

Using VectorDesigner, you can label the various features in a DNA/RNA or protein molecule, including promoter regions, open reading frames, binding sites, epitopes, or any other region of interest. The Feature Map folder in the Text Pane of the Molecule Viewer contains a list of labeled features. The Imported Features Not Shown on Map folder contains a list of unlabeled features. You can label as many features in a molecule as you want. Features are listed in the Text Pane and shown in the Graphics and Sequence Panes.

Adding Features

Note: You can label an open reading frame, restriction fragment, or primer as a feature. See Annotating Analysis.

To add a feature to the Feature Map folder: Select the part of the sequence that you want to label as a feature, or mark multiple areas of the sequence that you want to label as a single feature. Click on the Add Feature button or select the command from the Edit menu. (You can also right-click in the Graphics or Sequence Pane and select Add Feature from the context menu.) In the Add/Edit Feature dialog, the Feature Type field lists the available feature types in the database for the molecule. Select a feature type from the list. If you cannot find the precise type you are looking, select Misc. Feature. Note that you cannot add new feature types in VectorDesigner. Enter a name for the feature in the Feature Name field. Select the format to use for defining the sequence region:

Use Start-End Format or Use Start-Length Format. If you selected the feature region or marked multiple regions in the sequence before opening the dialog, the start and length/endpoint(s) of the feature will be automatically entered in the dialog. To change the region, enter the start and length/endpoint(s) in the fields. For features with multiple components (i.e., internal start and endpoints), select Multi-component and enter each start and length/endpoint in the field. Use the following format: <start1> . . . <length/endpoint1>, <start2 . . . length/endpoint2>, etc. Click on Reset to Selection to undo any changes you may have made to a preselected sequence region. Click on Reset to Mark to undo any changes you may have made to a marked sequence region. Select the Complementary checkbox if the feature is located on the complementary molecule strand. Note: VectorDesigner uses the currently accepted convention for calculating the coordinates of complementary features. All coordinates are given as if on the direct strand, from left to right in the sequence. Enter a description for the feature in the Description field. When you have made your selections, click OK to add the feature.

When you click on OK, information about the feature will be added to the Feature Map in the Text Pane, and the feature will be flagged in the Graphics and Sequence Panes as described below.

Viewing and Selecting Features

Text Pane: In the Text Pane, labeled features are listed by type under the Feature Map folder. Note that many of the feature types in VectorDesigner are mapped to keys in the GenBank and GenPept databases.

The user may click on the + button next to each feature type to view all the features of that type. Click on the + button next to each feature name to view the information for that feature, including sequence location, length, description, and any Web links Features with multiple components will list each component separately under the feature information. Double-click on the feature name in the Text Pane to display the feature in the Graphics and Sequence Panes.

Graphics Pane: Features are displayed in the Graphics Pane by large colored arrows. Hold your cursor over feature arrow to display a popup information box for that feature. Click on a feature arrow to select that feature in the Sequence Pane, or right-click on the arrow and select Find in Tree to locate the feature in the Text Pane.

Sequence Pane: In the Sequence Pane, features are marked by colored bars above the sequence. Click on feature bar in the Sequence Pane to select the feature in the Graphics Pane, or right-click on the arrow and select Find in Tree to locate the feature in the Text Pane.

Feature List: The Feature List, displayed in the Sequence Pane, lists each feature in the molecule in an easy-to-read table format. Double-click on the feature name in the Feature List to display the feature in the Graphics Pane.

Editing Features

To edit a feature: Right-click on the feature in the Feature Map folder, Feature List, or Imported Features Not Shown in Map folder; and Select Edit Feature Properties from the context menu. This opens the Add/Edit Feature dialog.

Deleting Features

You can delete the feature definition and information without removing the actual sequence of the feature from the molecule. In the Text Pane or Feature List, right-click on a feature and select Remove Feature. The feature information will be removed from the molecule file, but the sequence will remain unchanged. To undo a feature deletion, right-click in any pane in the Molecule Viewer and select Undo. To remove the sequence of a feature, see Inserting and Deleting Sequences. Marking Features You can mark features in the Sequence and Graphics Panes and combine them into new features.

Molecule Properties

The Molecule Properties dialog contains basic information about a DNA/RNA or protein molecule, including a description, references, associated genes, whether the molecule is circular or linear, and database links. Information entered in this dialog is shown in the Text Pane of the Molecule Viewer. To open the dialog, click on the Molecule Properties button on the main toolbar or select Properties from the Edit menu. The dialog is divided into several tabs.

The General Tab includes database information about the molecule file, including the database ID number and creation date.

Molecule Tab

DNA/RNA molecules: Select Circular or Linear and DNA or RNA from the dropdown lists.

Molecules with compatible overhangs will not circularize by joining the overhangs; rather, the ends will be filled in. Only DNA molecules flagged as Linear in this dialog can be used in the Molecule Construction workspace as inserts or vectors. The user may enter a brief description of the molecule in this field.

For Associated Genes, the user can click on Add Gene to add a gene associated with the molecule to the list. A gene entry is created in the table. Click in the editable text field to enter the gene name. This creates a database link that is useful if you export the molecule file to another format (GenBank, SWISSPROT, Vector NTI, etc.). To delete a gene entry, click on it in the table, then click on Remove Gene. The Comment Tab Enter any comments about the molecule in this field.

Standard Fields

This tab contains two subtabs. DNA/RNA molecules: The first tab is called Division/Organella/Keywords. You can click in the Division column and Organella column to select appropriate categories for the molecule. These will be highlighted for the molecule. Then you can enter the keywords as described below. Keywords: Click on Add Keyword to add a database keyword associated with the molecule to the list. A keyword entry is created in the table. Click in the editable text field (DO) to enter the keyword. This creates a database link that is useful if you export the molecule file to another format. To delete a keyword, click on it in the table, then click on Remove Keyword.

Source Organism: Click on this tab to display a table of organisms associated with the molecule. Click on Add Organism to add an organism associated with the molecule to the table. An organism entry is created in both columns in the table. Click in the editable text field in each column to enter the organism name in Latin and English. This creates a database link that is useful if you export the molecule file to another format (GenBank, SWISSPROT, Vector NTI, etc.). To delete a source organism, click on it in the table, then click on Remove Organism.

References Tab

Enter any references for the molecule in the field under this tab. This is a simple text-entry field. If you want to export the molecule in a particular format (e.g., GenBank), be sure to enter text in that format.

Feature List

The Feature List is list of the defined features in the molecule in an easy-to-read table format. The Feature List is displayed in the Sequence Pane. Click on the Feature List button to the left of the Sequence Pane to view the Feature List. Click on the Sequence Pane button to return to a view of the sequence. Click on a column header in the Feature List table to sort the list by that column. Right-click on a feature in the list and select Edit Feature Properties to open the Add/Edit Feature dialog. Right-click on a feature in the list and select Copy Text to copy the feature information to the computer clipboard in a tab-delimited format. Right-click on a feature in the list and select Open Link to access a variety of links to online databases with information about the feature. Note that links are available for only certain types of imported molecules.

Selecting a Sequence

Nucleotide and amino acid sequences are displayed in the Sequence Pane of the Molecule Viewer. In the Viewer, you can select part or all of a sequence, copy it, flag it as a feature, and otherwise analyze it.

Selecting Part or All of a Sequence

There are a number of ways to select part or all of a sequence. In the Molecule Viewer with the molecule displayed: Drag your cursor in the Sequence Pane or Graphics Pane. The selected part of the sequence will appear highlighted in both panes. Click on a defined feature, ORF, or restriction site in the Graphics or Text Pane, or double-click on a defined feature in the Feature List. The sequence of that feature will appear selected in the Sequence Pane. From the View menu or main toolbar, select Set Selection. In the Set Selection dialog, define the selection area and click on OK. The defined area will appear selected in the Graphics and Sequence Panes. Right-click in the Sequence Pane and select Select All to select the entire sequence.

Displaying Only the Selected Part of a Sequence

You can filter the display to show only the selected portion of the sequence. With the selection made, go to the View menu and select View Selection or click on the View Selection button on the main toolbar. To return to a full view of the molecule, go to the View menu and select View Entire Molecule or click on the View Entire Molecule button on the main toolbar.

Finding a Sequence

To find a molecule sequence within a larger sequence, right-click in the Sequence Pane in the Molecule Viewer and select Find Sequence. In the, dialog, type or paste the sequence you want to find, specify the search direction (Up or Down), and click on Find Next. Click on Find Next again to find the next occurrence of the sequence within the larger sequence. Click on Close to close the dialog.

Inserting and Deleting Sequences DNA and Protein Molecules

You can insert a new DNA or protein sequence into an existing DNA or protein molecule in the Molecule Viewer. Note that this command will only insert a new sequence at the insertion point; it will not overwrite any part of the existing sequence. With the molecule displayed, locate the point in the sequence where you want to insert the new sequence. Click on that point in the Sequence Pane. From the Edit menu or main toolbar, select Insert Sequence. The Insert Sequence dialog will open. In the dialog, note the insertion point listed below the field. Type or paste the new sequence into the field and click on OK. Note: Use only standard code letters when entering the sequence. Nonstandard characters will be marked with a ? in the Insert Sequence dialog and you will be prompted to remove them before adding the new sequence. If you are adding the sequence within a defined feature, the Feature Map is Updated dialog will open, listing the features in the molecule that will be affected by the insertion. In this dialog you can remove any or all of the defined features that will be changed. Note that this will not alter the change that you are making to the sequence; it will only remove the defined feature(s) affected by the change. Click on OK to make the changes. The sequence will be added to the molecule. If you flagged a feature for deletion in the Feature Map is Updated dialog, that feature will be removed.

To delete part of a sequence in the Molecule Viewer: With the molecule displayed, drag the cursor in the sequence or Graphics Pane to select the part of the sequence that you want to delete. From the View menu or main toolbar, select Delete Sequence. Note: You cannot delete the entire sequence in the Molecule Viewer. If you are deleting the sequence within a defined feature, the Feature Map is Updated dialog will open, listing the features in the molecule that will be affected by the deletion. In this dialog you can remove any or all of the defined features that will be changed. Note that this will not alter the change that you are making to the sequence; it will only remove the defined feature(s) affected by the change. Click on OK to make the changes. The sequence will be deleted from the molecule. If you flagged a feature for deletion in the Feature Map is Updated dialog, that feature will be removed.

For primers, the user can type, paste, and delete sequences directly in the Sequence field of the Edit Primer Properties dialog.

Copying a Sequence

You can copy a selected sequence to the computer clipboard. In the Sequence Pane of the Molecule Viewer Select the sequence. Right-click on the selected sequence in the sequence pane and select Copy. The sequence will be copied to the computer clipboard. You can then paste the copied sequence into your application of choice.

Marking a Sequence

You can mark regions of interest in a DNA or protein sequence with shading for easy comparison and reference. You can also mark multiple regions (e.g., the exons of a gene of interest) and label them as a single multi-segmented feature. In the Sequence Pane or Graphics Pane of the Molecule Viewer, select the region you want to mark, or click on the feature, ORF, or other defined element that you want to mark. Click on the Mark Selection button on the main toolbar, or select the command from the View menu or context menu (if you right-click in the Graphics Pane). The selected region will appear shaded-in the Sequence and Graphics Panes. Repeat the steps above to mark multiple regions in the sequence. You can then label them as a feature.

To unmark the sequence region: Select the marked region in the Sequence or Graphic Pane; Click on the Unmark Selection button on the main toolbar, or select the command from the View menu or context menu (if you right-click in the Graphics Pane); and Click on Unmark All to remove all the marks in the sequence.

Sequence Translation

You can use Vector Designer to translate the nucleotide sequence in a DNA molecule into amino acids. Note that only the Standard Genetic Code is available for translation. In the Molecule Viewer with a nucleotide sequence displayed: Select the part of the sequence that you want to translate. To select the entire sequence, right-click in the Sequence Pane and select Select AH. To translate the direct strand, click on the Translate Direct button on the main toolbar, or select the command from View>Translation menu. To translate the complementary strand, click on the Translate Complementary button on the main toolbar, or select the command from View>Translation menu. The translation will appear in the Sequence Pane as amino acid codes above the nucleotide sequence. To toggle between single-letter and three-letter amino acid codes, click on the 1 Letter/3 Letter Code button from the main toolbar or select the command from the View>Translation menu. To clear the translation from the display, click on the Clear Translations button on the main toolbar or select the command from the View>Translation menu.

Designing Primers and PCR Products Designing Primers

You can use VectorDesigner to design primers for a target sequence, or you can search for existing primers that are compatible with the sequence. The resulting PCR products can then be used in a variety of applications, including TOPO® Cloning, Gateway® Cloning, and standard PCR analysis or molecule construction. If you want to search for existing primers, the primers must be saved in the Primers folder of the database as separate primer files. The primer design settings are located in the PCR Analysis dialog of the Molecule Viewer.

In the dialog, you specify the parameters for designing or selecting the primers. Then VectorDesigner identifies one or more primer designs. You can then: Save the primer designs with the molecule or as separate files. Order the primers direct from Invitrogen. Save the PCR product generated by the primers as a separate molecule for further analysis. Evaluate the PCR product in a cloning or molecule construction strategy.

To identify primers for a molecule sequence: In the Molecule Viewer, select the region of the molecule for which you want to design primers. Alternatively, if you are searching for existing primers that are compatible with the molecule, you do not have to select any region (available for TOPO® Cloning and molecule construction applications only). Go to the Cloning menu, select the appropriate subfolder for your application—TOPO® Cloning, Gateway Cloning, or Molecule Construction. Select Design Primers to Amplify Selection to design primers for the selected sequence, or Find Amplicon in Sequence Using Existing Primers to evaluate existing primers for use with the molecule or selected sequence (available on the TOPO Cloning and Molecule Construction submenus only). The PCR Analysis dialog will open. The default values and available options will differ slightly depending on the application you selected (these differences are noted in the steps below). Under the Primer Definition and Construction tab, the From and To fields define the region that will be analyzed for primer designs. You can change the numbers in these fields. Next, enter the primer design parameters, or select the folders containing the saved primers that you want to evaluate for compatibility with the molecule sequence.

The following fields are only available if you selected Design Primers to Amplify Selection: To include primer design regions before and after the target sequence, enter a number of bases in the Before and After fields. Maximum # of Outputs: Enter the maximum number of primer pair designs to generate. Note that VectorDesigner may generate fewer designs if no more can be found. Tm: Enter the limits in degrees Celsius for primer melting temperature (Tm) (temperature at which 50% of primer is a duplex) in the Minimum and Maximum fields. Designs with Tm's outside this range will be excluded. % GC: Enter the maximum and minimum percent GC content for the primers in the fields. Designs with a percent GC content outside this range will be excluded. (The percent GC of any extensions are ignored.) Length: Enter the maximum and minimum length (in bases) of each primer in the fields. Designs that fall outside this range will be excluded. Nucleotide sequences such as RENs attached to a primer's 5' end are included when calculating primer length. Exclude Primers with Ambiguous Nucleotides: If your sequence includes ambiguous bases (i.e., code letters other than A,G,C,T), select this checkbox to exclude regions containing these bases from the primer design search.

The following fields are only available if you selected Find Amplicon in Sequence Using Existing Primers: Click on the Direct button to select the folder containing the direct primer sequences that you want to evaluate, and click on Complementary to select the folder containing the complementary primer sequences to evaluate. The Browse to Primer Folder dialog will open when you click on each button. Select the folder and click on OK. The primers must be saved in the Primers folder or subfolders as separate primer files. Enter a percentage similarity in the Similarity>=Threshold field. Each primer sequence must be at least this similar to the molecule sequence to be selected by the designer. Select the checkbox next to Last Nucleotides Must Have 100% Similarity to specify a number of nucleotides at the 3' end of each primer that must be 100% similar to the target sequence. Enter a number of nucleotides in the field. Next, select the conditions of the PCR reaction you are performing. If you are unsure of these values, use the default values: Salt cone: The salt concentration of the PCR reaction, in mMol. If you are unsure, use the default value of 50.0. Probe cone: The final concentration of the template in the reaction, in pMol. If you are unsure, use the default value of 250.0. dG temp: The temperature of the free energy value of the reaction, in degrees Celsius. If you are unsure, use the default value of 25.0.

Under Cloning Termini, select the type of PCR product you are generating. The available options will vary depending on your cloning application. Click on an application below for more information on how the primer and/or PCR product will be modified based on your selection: TOPO® Cloning PCR Products; Gateway® Cloning PCR Products; Molecule Construction PCR Products.

For cloning applications, under Cloning strand, select the strand whose sequence will be expressed: Direct or Complementary. Note that this will affect the primer strand to which Directional TOPO®, Gateway®, and other primer additions are added.

Next, select any sequence additions to each primer. This is optional. Primer additions (such as RENs) can be used to add sequences to the final PCR product for downstream applications such as restriction-ligation and protein expression. Click on the Browse button next to the Direct and/or Complementary fields. The Choose Direct/Complementary Strand Addition dialog will open. Select the strand additions in the dialog and click on OK. The additions will be listed in the appropriate field. Additions to the primer sequence will not be used in calculations of primer Tm, % GC, etc. If you change the Cloning Strand (step 5 above) after selecting the primer additions, the additions will switch to the other strand.

Click on the Pairing, Structure and Uniqueness tab to access additional primer specifications. Max. Tm Difference: Specify the maximum difference in melting temperature between sense and antisense primers in degrees Celsius. Max. % GC Difference: Specify the maximum percentage difference in GC content between sense and antisense primers. Note the differences in GC content between the two primer regions of the sequence when specifying this difference; a difference that is too small may result in no primers being found. Primer-Primer Complementarity: Permitted with dG>=: Select this checkbox and enter the minimum permitted value for free energy of a primer-primer duplex. Primer pairs which have a free energy value>/=to this number will be accepted. Primer-Primer Complementarity: 3' End Permitted with dG>=: Select this checkbox and enter the minimum permitted value for free energy of complementarity between the 3'-end of the primers (the final 5 bases of each primer will be evaluated). Primer pairs which have a 3'-end complementarity free energy value>/=to this number will be accepted. Exclude Primers With: In the Repeat field, enter the maximum number of base-pair repeats allowed in each primer. In the Palindrome field, enter the maximum permitted length of palindromes in each primer sequence. In the Hairpin Loops field, enter the minimum permitted value for free energy of hairpin loops within each primer. Primer Uniqueness: Select this checkbox to reject primers above a certain percentage similarity to secondary sites within either the entire sequence or within the amplicon. Enter an percentage similarity in the field, and select Within Entire Sequence or Within Amplicon Only.

Click on OK to design the primers. You will be prompted to send the PCR product for the first (highest ranked) primer pair directly to the appropriate molecule construction workspace as an insert. If you click on No, all the primer pairs generated will be added to the PCR Primers folder in the Text Pane of the Molecule Viewer. Primer Designs and PCR Products After you have designed primers from a molecule sequence using the tools in the Molecule Viewer, the primer designs and their PCR products will be listed in the PCR Primers folder of the Text Pane. Viewing Primer Designs in the Text Pane In the Text Pane, information about each primer design is included in the PCR Primers folder. Note: Only the designs for most recent target sequence are saved in this folder. If you design primers for a different target sequence, the new designs will replace any old ones. To preserve the primer designs for a particular target sequence, save them as features as described below.

In the PCR Primers folder, the PCR product for each primer pair has its own subfolder: Double-click on the subfolder to select the amplicon region in the graphics and Sequence Panes; Click on the + next to the PCR product folder name view the information for the primer pair; Double-click on each individual primer sequence in the PCR product folder to highlight that sequence in the graphics and Sequence Panes.

Ordering Primers from Invitrogen

Click on the Order from Invitrogen link next to each primer in the Text Pane to order the primer from Invitrogen. You will be prompted to enter a primer name, and the primer sequence will automatically be loaded into Invitrogen's online ordering system. You can specify the details of your order (purity, synthesis scale, etc.) on the Web site.

Adding a PCR Product to a Workspace

To load a PCR product in the TOPO® Cloning, Gateway® Cloning, or Molecule Construction workspace as an insert: In the PCR Primers folder in the Text Pane, right-click on the Product folder for the PCR product and select Add PCR Product to <application> Workspace (Note that specific application workspace listed will depend on which type of PCR analysis was used to generate the product); and the workspace will be displayed in the main VectorDesigner window, and the PCR product will be listed in the Insert field.

Saving the PCR Product as a New Molecule

To open the PCR product as a separate molecule: Right-click on the PCR product folder in the PCR Primers folder and select Open PCR Product in New Molecule Viewer. A new Molecule Viewer will open displaying the amplicon sequence as a linear DNA molecule, with the primers marked as features. Note that the new molecule is not automatically saved in the database; use the Save command in the Viewer to save the new molecule.

Saving Individual Primer Designs as New Molecules

To save the primer designs as individual primers in the database: Right-click on the primer sequence in the Text Pane (i.e., the actual sequence of the specific direct or complementary primer) and select Save Primer into DB. The Save As dialog box will open, prompting you to specify the primer name. Primers may be saved in the Primers folder or subfolders. To open the new primer file, go to the Database Browser window and double-click on the primer in the Primers folder. The Edit Primer Properties dialog will open.

Adding a PCR Product to the Feature Map

To add one more PCR products to the Feature Map: In the PCR Primers folder in the Text Pane, right-click on a Product folder and select Annotate Analysis Item. In the Add/Edit Feature dialog; fill out the information and click on OK to add the PCR product to the feature map. To undo this command, right-click in the Text Pane and select Undo Annotate Analysis. Adding Primer Designs to the Feature Map To add all primer designs to the Feature Map: In the Text Pane, right-click on the PCR Primers folder and select Annotate Analysis. The Annotate Analysis dialog will open; select the feature type and enter a feature name and description, and click on OK. Note that you can only fill out a single name all the primer designs; the individual primers will be given the name plus a numerical extension (<primer name>.sub.-1, <primer name>.sub.-2, etc.).

To add one or more primer pairs to the Feature Map: In the PCR Primers folder in the Text Pane, right-click on the Product folder for a primer pair, or hold down the Control key and click on multiple Product folders to select them and right-click on the selection. Select Annotate Analysis from the context menu. The Annotate Analysis dialog will open; select the feature type and enter a feature name and description, and click on OK. Note that you can only fill out a single name all the primer designs; the individual primers will be given the name plus a numerical extension (<primer name>1, <primer name>.sub.-2, etc.). To add an individual primer sequence to the Feature Map: In the PCR Primers folder in the Text Pane, open the Product folder for the design you want and right-click on the primer sequence (i.e., the actual sequence of the specific direct or complementary primer). Select Annotate Analysis from the context menu. The Annotate Analysis dialog will open; fill out the information and click on OK. The primer sequence will be added. To undo these commands, right-click in the Text Pane and select Undo Annotate Analysis.
Deleting Primer Designs To delete a PCR primer design from the molecule file: In the PCR Primers folder in the Text Pane, right-click on the Product folder and select Remove Site. The information for the primer designs and PCR product will be removed. (Note that the actual molecule sequence will not be affected.) To remove all primer designs from the molecule, right-click on the PCR Primers folder in the Text Pane and select Remove Analysis.
Marking/Highlighting Primer Designs To mark a single PCR product in the Sequence and Graphics Panes with shading: In the PCR Primers folder in the Text Pane, right-click on the Product folder and select Mark Site.

To mark multiple PCR products in the Sequence and Graphics Panes with shading: In the PCR Primers folder in the Text Pane, hold down the Control key and click the Product folders to select-them, then right-click on the selection and select Mark Selected Items.

To mark a single primer sequence in the Sequence and Graphics Panes with shading: In the PCR Primers folder in the Text Pane, open the Product folder for the design, right-click on the specific primer sequence, and select Mark Site. (Note that you must right-click on the actual primer sequence, not the primer name.)

To mark multiple primer sequences in the Sequence and Graphics Panes with shading: In the PCR Primers folder in the Text Pane, open the Product folder(s) containing the primer designs, hold down the Control key and click on the primer sequences to select them, and then right-click on the selection and select Mark Selected Items. (Note that you must select the actual primer sequences, not the primer names.) To undo a marked region, select the PCR product and select View>Unmark Selection.

ORFs and Restriction Mapping Open Reading Frames

You can identify open reading frames (ORFs) in DNA molecules using the ORF Search tool in the Molecule Viewer. ORFs identified by the tool are shown in the Graphics, Sequence, and Text Panes, as described below.
Identifying ORFs Using the ORF Search tool, you can set the minimum ORF size, the start and stop codons to search for, and other parameters, and VectorDesigner will generate a list of defined ORFs. To perform the ORF search: In the Molecule Viewer displaying a DNA molecule, click on the ORF Search button or go to the Tools menu and select ORF Search. In the ORF Search dialog, specify the Minimum ORF Size (in codons) and select the Nested ORFs checkbox if you want to search for nested ORFS(ORFs that have the same stop codon but different start codons). In Start Codons and Stop Codons fields, enter one or more start and stop codons to search for when identifying ORFs. Separate each codon by a space. To reset the fields, click on Reset to Default. Select Include Stop Codon in ORF if you want the stop codon to be considered part of the ORF. Otherwise, the stop codon will not be included in each ORF defined in the sequence. Click on OK to search for the ORFs.

The ORFs will be marked on the sequence in the Graphics and Sequence Panes, and a folder called Open Reading Frames will be created in the Text Pane. If you perform the ORF search again, the existing search results will be overwritten.
Viewing and Selecting ORFs Each pane in the Molecule Viewer has different tools for viewing and selecting ORFs. Graphics Pane: In the Graphics Pane, ORFs are marked by thin directional arrows aligned with the sequence. Hold your cursor over an ORF arrow to display a popup information box for that ORF. Click on an arrow to highlight the ORF in the Sequence Pane. Right-click on an ORF and select Find in Tree to select the ORF in the Text Pane.

Sequence Pane: In the Sequence Pane, ORFs are marked by black bars above the sequence. Click on an ORF arrow in the Graphics Pane or an ORF name in the Text Pane to highlight the sequence in the Sequence Pane.

Text Pane: In the Text Pane, information about identified ORFs is included in a folder called Open Reading Frames. In this folder, each ORF is listed by its position in the sequence. The notation (D1, D2, D3, or C1, C2, C3) refers to the strand containing the ORF and its reading frame in the molecule sequence. For example, in a direct strand sequence beginning ATGTGTACTCCTTA . . . (SEQ ID NO:9), an ORF beginning with ATG would have the notation D1 and an ORF beginning with GTG would have the notation D3. Double-click on an ORF name in the folder to highlight the ORF in the Graphics and Sequence Panes. Click on the + next to each ORF name to view the start codon, stop codon, region of the sequence, and length of each ORF.
Adding ORFs to the Feature Map You can add ORFs to the Feature Map in one of two ways: In the Text Pane, right-click on an ORF in the Open Reading Frames folder and select Annotate Analysis. The Annotate Analysis dialog will open; fill out the information and click on OK to add the ORF to the feature map. Note that this dialog will only enable you to add the ORF sequence as defined by the ORF Search tool. To undo this command, right-click in the Text Pane and select Undo Annotate Analysis. If you want to alter the start and/or endpoint of the ORF before defining it as a feature, right-click on the ORF in the Open Reading Frames folder and select Annotate Analysis Item. This will open the Add/Edit Feature dialog, in which you can change the start/endpoint of the feature. To undo this command, right-click in the Text Pane and select Undo Annotate Analysis.

Deleting ORFs

You can delete an ORF definition and information without removing the ORF sequence from the molecule. In the Text Pane, right-click on an ORF and select Remove Site. The ORF information will be removed from the panes, but the sequence will remain unchanged. To remove all ORF definitions from the molecule, right-click on the Open Reading Frames folder in the Text Pane and select Remove Analysis. To undo an ORF deletion, right-click in any pane in the Molecule Viewer and select Undo. To remove the sequence of an ORF, see Inserting and Deleting Sequences. Marking/Highlighting ORFs You can mark the ORF sequence in the Sequence and Graphics Panes with shading. In the Text Pane, right-click on the ORF and select Mark Site. In the Graphics Pane, right-click on the ORF arrow and select Mark Selection. Or, with the ORF selected in the Sequence Pane, go to the View menu and select Mark Selection. To undo a marked ORF, select the ORF and select View>Unmark Selection. Restriction Analysis Vector Designer can identify the restriction enzyme cut sites in a DNA molecule using a built-in database of restriction enzymes. You can use the cut sites to generate restriction fragments for molecule construction.

Restriction Map Search

To perform restriction analysis: In the Molecule Viewer displaying a DNA molecule, click on the Restriction Map Search button (RMap) or go the Tools menu and select Restriction Map Search. In the Restriction Map Search dialog, select the category of enzymes that you want to use from the Use Enzymes list: Frequently Used Enzymes have been identified by Invitrogen. Click here for a list. 7+Cutters, 6 Cutters, 5 Cutters, etc. refer to the number of base pairs in the recognition site of each enzyme. Enzymes in the 5' Overhang category result in fragments with a 5' overhang; enzymes in the 3' Overhang category result in fragments with a 3' overhang. If you select Customized, click on the Customize button to select the particular enzymes you want to use. The Enzymes List dialog will open.

Next, enter a number in the Display Enzymes with <=Recognition Sites field. The Designer will analyze the sequence and use only those enzymes with less than or equal to that number of cut sites. Alternatively, select Unlimited to not filter the enzyme list by number of cut sites. When you have made your selections, click on OK.

Viewing and Selecting Restriction Sites

Each pane in the Molecule Viewer has different tools for viewing and selecting restriction sites. Graphics Pane In the Graphics Pane, restriction sites are marked by blue-green lines from the site to the name of the restriction enzyme. Hold your cursor over the restriction enzyme name to display a popup information box for that site. Click on a restriction site to highlight the site in the Sequence Pane. Right-click on a restriction site and select Find in Tree to select the site in the Text Pane. See Restriction Fragments for instructions on selecting fragments in the Graphics Pane.

Sequence Pane: In the Sequence Pane, restriction sites are marked by blue bars above the sequence and the name of the enzyme above the bar. Click on the blue bar above the sequence to display a line through the sequence showing the exact cut site and overhang created by the enzyme. See Restriction Fragments for instructions on selecting fragments in the Sequence Pane.

Text Pane: In the Text Pane, information about identified restriction sites is included in a folder called Restriction Map. In this folder, each restriction site is listed by enzyme name. Double-click on a restriction site in the folder to highlight the site in the Graphics and Sequence Panes. Click on the + next to each enzyme name to view the complete name of the organism and the locations in the sequence where it cuts. Click on the Order from Invitrogen link to order the restriction endonuclease from Invitrogen. You will be linked to Invitrogen's online catalog page for the enzyme.

Adding Restriction Sites to the Feature Map

You can add restriction sites to the Feature Map. In the Text Pane, right-click on a restriction site in the Restriction Map folder and select Annotate Analysis. The Annotate Analysis dialog will open; fill out the information and click on OK to add the restriction site. To undo this command, right-click in the Text Pane and select Undo Annotate Analysis. To remove all restriction site definitions from the molecule, right-click on the Restriction Map folder in the Text Pane and select Remove Analysis.

Restriction Fragments Selecting a Restriction Fragment

You can select the region between two restriction enzyme cut sites in the Graphics or Sequence Pane to generate a restriction fragment. See Restriction Analysis for information on generating a list of cut sites. Before proceeding, you may want to limit the display to just the enzymes you are interested in using the Link Mode feature.

In the Graphics Pane with the restriction enzyme cut sites displayed, click on a restriction enzyme name, hold down the Shift key, and click on a second enzyme name. The region between the two cut sites will appear selected in the Sequence Pane.

In the Sequence Pane with the restriction enzyme cut sites displayed, click on the blue bar above a restriction site, hold down the Shift key, and click on a second blue bar. The region between the two cut sites will appear selected. Now you can copy the selected fragment, define it as a feature, or add it to the Molecule Construction workspace as an insert or a vector.

Adding a Fragment to the Molecule Construction Workspace

To add the feature to the Molecule Construction workspace as an insert or a vector: With the fragment selected, go to the Cloning>Molecule Construction menu and select Add Restriction Fragment to Workspace as an Insert or Add Restriction Fragment to Workspace as a Vector. The Molecule Construction workspace will be displayed in the main VectorDesigner window, and the fragment will be listed in the appropriate field (Insert or Vector).

Cloning Tools Molecule Construction

VectorDesigner provides automated tools for in silico construction of DNA molecules (e.g., expression clones) from existing sequences based on conventional cloning methodologies (e.g., restriction-ligation, TA cloning). VectorDesigner also provides tools for in silico molecule construction using Gateway® Cloning and TOPO® Cloning technologies.

Using these tools, you first design and select the sequences/molecules that you want to use to create the new molecule and add them to the Molecule Construction workspace. When you click on Clone, VectorDesigner will automatically select the optimal sites for recombination and generate and display the new design. The tools for in silico molecule construction are located in the Molecule Construction workspace in the main VectorDesigner window. Click on the Molecule Construction tab to view the workspace.

To construct molecules, you must first design and/or select an insert sequence and a vector sequence, as described below. The insert and vector sequences must have compatible ends (e.g., blunt ends or compatible overhangs). VectorDesigner can be used to construct a DNA molecule from one insert and one vector at a time. Vector NTI® software provides a suite of additional tools and options for constructing molecules. Selecting Inserts Inserts must be linear DNA sequences, and must have compatible ends with the vector you select. Examples include the following: Restriction fragments—see Restriction Analysis and Restriction Fragments; PCR products—see Designing Primers and Primer Designs and PCR Products; Linear DNA molecules (blunt-ended or with T-A extensions)

Selecting Inserts in the Molecule Construction Workspace

If the insert has been saved as a molecule in the VectorDesigner database, you can select it in the Molecule Construction workspace. Note that the insert must be saved in the DNA/RNAs folder or a subfolder. Click on the Browse in Insert button in the workspace. The window will expand, displaying navigation tools at the bottom. Using the folder tree in the left-hand part of the window, navigate to the folder containing your insert. Click on the insert name in the right-hand part of the window. The insert will be added to the Insert field in the workspace. (Note that you may need to scroll up in the window to view the Insert field.)
Selecting Inserts in the Molecule Viewer The Molecule Viewer includes a number of tools for generating inserts and transferring them to the Molecule Construction workspace. See Restriction Fragments for instructions on selecting a restriction fragment in the Molecule Viewer and adding it to the Molecule Construction workspace as an insert. See Primer Designs and PCR Products, for instructions on selecting a PCR product in the Molecule Viewer and adding it to the Molecule Construction workspace as an insert.

When you design primers for a molecule sequence using the tools on the Cloning>Molecule Construction menu, you will be prompted to send the PCR product from the primary design directly to the Molecule Construction workspace. (See Designing Primers.) If you select No, the product will be added to the PCR Primers folder in the Text Pane and you can add it to the workspace from there. (See Primer Designs and PCR Products). You can transfer the entire molecule to the workspace as an insert. In the Molecule Viewer, go to the Cloning>Molecule Construction menu and select Add Entire Molecule to Workspace as Insert. Note that the molecule must be linear for this command to be available. When you use any of the methods above, the Molecule Construction workspace window will be displayed and the selected sequence will be listed in the Insert field.
Selecting Vectors Vectors must be linear DNA sequences, and must have compatible ends with the insert you select. Examples include the following: Restriction fragments—see Restriction Analysis and Restriction Fragments; Linear DNA molecules (e.g., linearized vectors; blunt-ended or with T-A extensions)
Selecting Vectors in the Molecule Construction Workspace If the vector has been saved as a molecule in the VectorDesigner database, you can select it in the Molecule Construction workspace. Click on the Browse in Vector button in the workspace. The window will expand, displaying navigation tools at the bottom. Using the folder tree in the left-hand part of the window, navigate to the folder containing your vector. Click on the vector name in the right-hand part of the window. The vector will be added to the Vector field in the workspace. (Note that you may need to scroll up in the window to view the Insert field.)
Selecting Vectors in the Molecule Viewer The Molecule Viewer includes tools for generating restriction fragments that can used as vectors. You can also transfer the entire molecule to the workspace as a vector. See Restriction Fragments for instructions on selecting a restriction fragment in the Molecule Viewer and adding it to the Molecule Construction workspace as a vector. You can transfer the entire molecule to the workspace as a vector. In the Molecule Viewer, go to the Cloning>Molecule Construction menu and select Add Entire Molecule to Workspace as Vector. Note that the molecule must be linear for this command to be available. When you use either of these methods, the Molecule Construction workspace window will be displayed and the selected sequence will be listed in the Vector field.

Incompatible Termini

If you have added inserts and/or vectors with incompatible termini to the workspace, an alert message will appear in the left-hand pane of the Molecule Construction workspace. You will be prompted to: Select different inserts/vectors; Modify the inserts/vectors using restriction enzymes that will result in compatible termini; or Fill/trim any incompatible overhangs.

To modify an insert or vector, open it in the Molecule Viewer and use the editing tools in the Viewer to make the changes. Then re-add it to the Molecule Construction workspace. To fill or trim incompatible overhangs, use the pulldown boxes in the Insert and Vector fields in the Molecule Construction workspace to select the appropriate options (None, Fill, or Trim).
Creating the New Molecule When you have added a compatible insert to the Insert field and a compatible vector to the Vector field, the Clone button in the Molecule Construction workspace will become active. Click on Clone to create the new molecule. The molecule will open in a new Molecule Viewer window. The insert may clone into the vector in both orientations, depending on the compatibility of the terminals. In this case, two new molecules will open. Use the Save command in the Molecule Viewer to save the new molecule.

Information about the New Molecule

Any features from the constituent molecules will be preserved in the new molecule, except for features that may be eliminated or truncated in the reaction. In addition to the standard information provided in the Molecule Viewer, the following information is provided for constructed molecules: In the Text Pane, the Design Description outlines the steps for the appropriate cloning reaction. In the Text Pane, the Component Fragments folder provides a description of each molecule fragment used to construct the molecule. Under each fragment, click on Open in Molecule Viewer to open the fragment in a new Viewer window (note that the fragment in the new Viewer window will not be saved).

Analysis of the New Molecule

You can now analyze the new molecule using analysis tools such as the open reading frame and sequence translation tools in VectorDesigner to verify that the DNA sequence is inserted and will be expressed as intended.

Gateway Cloning Overview of Gateway® Cloning

Gateway® Technology is based on the bacteriophage lambda site-specific recombination system (atth.times.attR<=>attB.times.attP), which involves DNA recombination sequences att sites) and proteins that bring together the target sites, cleave them, and covalently attach the DNA. Gateway® Technology uses lambda recombination to facilitate the transfer of heterologous DNA sequences (flanked by modified att sites) between vectors. Two recombination reactions constitute the basis of the Gateway® Technology: (1) BP Reaction: Facilitates recombination of an attB substrate (attB-PCR product or a linearized attB expression clone) with an att? substrate (donor vector) to create a//L-containing entry clone. This reaction is catalyzed by BP Clonase™ II enzyme mix; and (2) LR Reaction: Facilitates recombination of an attL substrate (entry clone) with an attR substrate (destination vector) to create an aftB-containing expression clone (see diagram below). This reaction is catalyzed by LR Clonase™ II enzyme mix.

More information about Gateway® Technology: Gateway® Technology can be found in the Gateway® Technology manual, which is available on the World Wide Web at invitrogen.com. Gateway® Cloning VectorDesigner provides automated tools for in silico construction of Gateway® entry clones and Gateway® expression clones from existing sequences and vectors. Using VectorDesigner, you can construct a: Gateway® entry clone using an atiB substrate (attB-PCR product or attB-expression clone) and a donor vector (BP reaction); and/or Gateway® expression clone using an entry clone (attL substrate) and destination vector (LR reaction). In VectorDesigner, you first design and select the substrates and vectors that you want to use to create the new entry clone or expression clone and add them to the Gateway® Cloning workspace. When you click on Clone, VectorDesigner will automatically recombine the sequences and generate and display the new molecule. The tools for in silico Gateway® Cloning are located in the Gateway® Cloning workspace in the main VectorDesigner window. Click on the Gateway® Cloning tab to view the workspace.

To construct molecules, you must first design and/or select an insert and a vector: The insert in VectorDesigner is an attB substrate (attB-FCR product or attB-expression clone) if you are generating a Gateway® entry clone (BP reaction) or an entry clone if you are generating a Gateway® expression clone (LR reaction). The vector in VectorDesigner is a Gateway® donor vector if you are generating a Gateway® entry clone (BP reaction) or a Gateway® destination vector if you are generating a Gateway® expression clone (LR reaction). Files of Gateway® vectors are included in the Invitrogen Vectors>Gateway Vectors folder in VectorDesigner.

Selecting Inserts

The type of insert you select will depend on whether you want to perform a BP reaction to generate a Gateway® entry clone or an LR reaction to generate a Gateway® expression clone.

To generate a Gateway® entry clone (BP reaction), inserts can be: attB PCR products—see Designing Primers and Primer Designs and PCR Products for generating and selecting Gateway®-adapted PCR products containing attB sites; any DNA molecule containing attB sites; a Gateway® expression clone.

To generate a Gateway® expression clone (LR reaction), the insert must be a Gateway® entry clone. You can generate an entry clone using the following methods: Perform a BP reaction using an attB substrate and a donor vector; Use TOPO® Cloning or conventional cloning methods to insert your sequence of interest into a pENTR/TOPO® or pENTR vector from Invitrogen. Molecule files of top-selling pENTR/TOPO® vectors are provided in the Invitrogen Vectors>TOPO Vectors>Directional folder, and files of top-selling pENTR vectors are provided in the Invitrogen Vectors>Gateway Vectors>pENTR Vectors folder in VectorDesigner.

Selecting Inserts in the Gateway® Cloning Workspace

If the insert has been saved as a molecule in the VectorDesigner database, you can select it in the Gateway® Cloning workspace. Note that the insert must be saved in the DNA/RNAs folder or a subfolder. Click on the Browse in Insert button in the workspace. The window will expand, displaying navigation tools at the bottom. Using the folder tree in the left-hand part of the window, navigate to the folder containing your insert. Click on the insert name in the right-hand part of the window. The insert will be added to the Insert field in the workspace. (Note that you may need to scroll up in the window to view the Insert field.)

Selecting Inserts in the Molecule Viewer

The Molecule Viewer includes tools for designing Gateway®-adapted PCR products and transferring them to the Gateway® Cloning workspace. See Designing Primers. See Primer Designs and PCR Products for instructions on selecting a PCR product in the Molecule Viewer and adding it to the Gateway® Cloning workspace as an insert. When you design primers for a molecule sequence using the tools on the Cloning>Gateway Cloning menu, you will be prompted to send the resulting attB PCR product directly to the Gateway® Cloning workspace. You can transfer an entire molecule to the workspace as an insert. In the Molecule Viewer, go to the Cloning>Gateway Cloning menu and select Add Molecule to Workspace as Insert. When you use any of the methods above, the Gateway® Cloning workspace window will be displayed and the selected sequence will be listed in the Insert field.

Selecting Vectors

The type of vector you select will depend on whether you want to perform a BP reaction to generate a Gateway® entry clone or an LR reaction to generate a Gateway® expression clone: To generate a Gateway® entry clone (BP reaction), you must select a Gateways donor vector. Molecule files of top-selling donor vectors are provided in the Invitrogen Vectors>Gateway Vectors>pDONR Vectors folder in VectorDesigner. Sequences of additional donor vectors can be located by searching the Invitrogen Vectors Web database. To generate a Gateway® expression clone (LR reaction), you must select a Gateway® destination vector. Molecule files of top-selling destination vectors are provided in the Invitrogen Vectors>Gateway Vectors>pDEST Vectors folder in VectorDesigner. Sequences of additional destination vectors can be located by searching the Invitrogen Vectors Web database.

Selecting Vectors in the Gateway® Cloning Workspace

If the Gateway® vector is in the VectorDesigner database, you can select it in the Gateway® Cloning workspace: Click on the Browse in Vector button in the workspace. The window will expand, displaying navigation tools at the bottom. Using the folder tree in the left-hand part of the window, navigate to the folder containing your vector. Click on the vector name in the right-hand part of the window. The vector will be added to the Vector field in the workspace. (Note that you may need to scroll up in the window to view the Insert field.)

Selecting Vectors in the Molecule Viewer

From the Molecule Viewer, you can transfer the Gateway® vector to the workspace. Go to the Cloning>Gateway Cloning menu and select Add Molecule to Workspace as Vector. The Gateway® Cloning workspace window will be displayed and the selected sequence will be listed in the Vector field.

Creating the New Molecule

After you have added a compatible insert to the Insert field and a compatible vector to the Vector field, the Clone button in the Molecule Construction workspace will become active. If you select incompatible inserts and/or vectors, an alert message will appear in the left-hand pane of the Molecule Construction workspace, and you will be prompted to select different inserts/vectors.

Click on Clone to create the new molecule. The molecule will open in a new Molecule Viewer window. Use the Save command in the Molecule Viewer to save the new molecule.

Information about the New Molecule

Any features from the constituent molecules will be preserved in the new molecule, except for features that are eliminated and added in the recombination reaction (e.g., the atth sites in an entry clone and attR sites in a destination vector will be eliminated and replaced by attB sites in the expression clone).

In addition to the standard information provided in the Molecule Viewer, the following information is provided for constructed molecules: In the Text Pane, the Design Description outlines the steps for the appropriate cloning reaction. In the Text Pane, the Component Fragments folder provides a description of each molecule fragment used to construct the molecule. Under each fragment, click on Open in Molecule Viewer to open the fragment in a new Viewer window (note that the fragment in the new Viewer window will not be saved).

Analysis of the New Molecule

You can analyze entry clones and expression clones using the open reading frame and sequence translation analysis tools in VectorDesigner to verify that the sequence has the correct reading frame and translation.

TOPO® Cloning TOPO® technology uses the unique properties of vaccinia DNA topoisomerase I to mediate rapid, joining of PCR products into plasmid vectors. No ligase, post-PCR procedures, or PCR primers containing specific sequences are required. For more information, visit the TOPO® Cloning Web site on the World Wide Web at invitrogen.com.

Zero Blunt® TOPO® Cloning

Each Zero Blunt® TOPO® vector has Topoisomerase I covalently bound to both vector terminals. This allows blunt-end PCR products to ligate efficiently with the vector.

TOPO TA Cloning®

Taq DNA polymerase has a nontemplate-dependent terminal transferase activity that adds a single deoxyadenosine (A) to the 3' ends of PCR products. Each TOPO® TA vector has overhanging 3' deoxythymidine (T) residues and Topoisomerase I covalently bound to the vector terminals. This allows PCR inserts generated with Taq polymerase to ligate efficiently with the vector.

Directional TOPO® Cloning

In this system, PCR products are directionally cloned by adding four bases to the forward primer (CACC). The TOPO®-charged overhang in the cloning vector (GTGG) invades the 5' end of the PCR product, anneals to the added bases, and stabilizes the PCR product in the correct orientation. Inserts can be cloned in the correct orientation with efficiencies equal to or greater than 90%.

TOPO® Cloning VectorDesigner provides automated tools for in silico construction of expression clones from DNA sequences using TOPO® cloning technology. You can construct clones using TOPO® TA Cloning, Directional TOPO® Cloning, and Blunt TOPO® Cloning methods.

In VectorDesigner, you first design and select the sequences (typically PCR products) and TOPO® vectors that you want to use to create the new expression clone and add them to the TOPO® Cloning workspace. When you click on Clone, VectorDesigner will automatically recombine the sequences and generate and display the new molecule.

The tools for in silico TOPO® Cloning are located in the TOPO® Cloning workspace in the main VectorDesigner window. Click on the TOPO® Cloning tab to view the workspace.

To construct molecules, you must first design and/or select an insert and a vector: The insert should be a DNA sequence—typically a PCR product in TOPO® applications—configured for the type of TOPO® Cloning you want to perform (e.g., TA, Directional, Blunt). The vector should be an appropriate TOPO® vector. Files of TOPO® vectors are included in the Invitrogen Vectors>TOPO Vectors folder in VectorDesigner. Selecting Inserts Inserts must be linear DNA sequences. They can be: PCR products—see Designing Primers and Primer Designs and PCR Products for generating and selecting TOPO®-adapted PCR products; Linear DNA molecules—If you select a molecule with Blunt ends, use a Zero Blunt® TOPO® Vector; with 3' A overhangs, use a TOPO® TA Vector; or with a CACC sequence at one end, use a Directional TOPO® Vector or Zero Blunt® TOPO® Vector.

Selecting Inserts in the TOPO® Cloning Workspace

If the insert has been saved as a molecule in the VectorDesigner database, you can select it in the TOPO® Cloning workspace. Note that the insert must be saved in the DNA/RNAs folder or a subfolder. Click on the Browse in Insert button in the workspace. The window will expand, displaying navigation tools at the bottom. Using the folder tree in the left-hand part of the window, navigate to the folder containing your insert. Click on the insert name in the right-hand part of the window. The insert will be added to the Insert field in the workspace. (Note that you may need to scroll up in the window to view the Insert field.)

Selecting Inserts in the Molecule Viewer

The Molecule Viewer includes tools for designing TOPO®-adapted PCR products and transferring them to the TOPO® Cloning workspace. See Designing Primers. See Primer Designs and PCR Products for instructions on selecting a PCR product in the Molecule Viewer and adding it to the TOPO® Cloning workspace as an insert.

When you design primers for a molecule sequence using the tools on the Cloning>TOPO Cloning menu, you will be prompted to send the resulting PCR product directly to the TOPO® Cloning workspace. You can transfer an entire molecule to the workspace as an insert. In the Molecule Viewer, go to the Cloning>TOPO Cloning menu and select Add Molecule to Workspace as Insert. Note that the molecule must be linear for this command to be available. When you use any of the methods above, the TOPO® Cloning workspace window will be displayed and the selected sequence will be listed in the Insert field.

Selecting Vectors

Vectors must be linear TOPO® vectors, and must have compatible ends with the insert you select. Molecule files of top-selling TOPO® vectors are provided in the Invitrogen Vectors>TOPO Vectors folder in VectorDesigner.

Selecting Vectors in the TOPO® Cloning Workspace

If the TOPO® vector is in the VectorDesigner database, you can select it in the TOPO® Cloning workspace. Click on the Browse in Vector button in the workspace. The window will expand, displaying navigation tools at the bottom. Using the folder tree in the left-hand part of the window, navigate to the folder containing your vector. Click on the vector name in the right-hand part of the window. The vector will be added to the Vector field in the workspace. (Note that you may need to scroll up in the window to view the Insert field.)

Selecting Vectors in the Molecule Viewer

From the Molecule Viewer, you can transfer the TOPO® vector to the workspace. Go to the Cloning>TOPO® Cloning menu and select Add Molecule to Workspace as Vector. The TOPO® Cloning workspace window will be displayed and the selected sequence will be listed in the Vector field.

Creating the New Molecule

After you have added a compatible insert to the Insert field and a compatible vector to the Vector field, the Clone button in the Molecule Construction workspace will become active. If you select inserts and/or vectors with incompatible termini, an alert message will appear in the left-hand pane of the Molecule Construction workspace, and you will be prompted to select different inserts/vectors. Click on Clone to create the new expression clone. The molecule will open in a new Molecule Viewer window. Use the Save command in the Molecule Viewer to save the new molecule. Information about the New Molecule Any features from the constituent molecules will be preserved in the new molecule, except for features that may be eliminated in the recombination reaction (e.g., a TA overhang feature).

In addition to the standard information provided in the Molecule Viewer, the following information is provided for constructed molecules: In the Text Pane, the Design Description outlines the steps for the appropriate cloning reaction. In the Text Pane, the Component Fragments folder provides a description of each molecule fragment used to construct the molecule. Under each fragment, click on Open in Molecule Viewer to open the fragment in a new Viewer window (note that the fragment in the new Viewer window will not be saved). Analysis of the New Molecule You can now analyze the expression clone using the open reading frame and sequence translation analysis tools in VectorDesigner to verify that the DNA sequence is inserted and will be expressed as intended. CloneRanger™

You can search Invitrogen's online clone collection for a specific DNA target sequence using the online Web tool CloneRanger™. VectorDesigner can link to CloneRanger™ and automatically enter a selected target sequence into the search field.

To use CloneRanger™, in the Molecule Viewer dialog: Select the part of the molecule sequence that you want to search for, or make no selection if you want to search for the entire molecule sequence. Click on the CloneRanger button (CloneRanger) on the main toolbar, or select the command from the Tools menu. The CloneRanger™ Web site will open, and a BLAST search for the sequence will be automatically initiated. When the search is complete, the BLAST search results page will be displayed. At this point, you can: Use the tools in CloneRanger™ to select and order the desired clone; select the desired clone and click on Send to VectorDesigner to import the clone sequence back into VectorDesigner. See Importing Clones for more information. Importing Clones from CloneRanger™

If you have identified one or more clones containing your sequence of interest in Invitrogen's CloneRanger™ Web tool, you can click on Send to VectorDesigner in the CloneRanger™ results page to import the clone sequence(s) into VectorDesigner for analysis.

After you click on Send to VectorDesigner in CloneRanger™, the Import Clones window will open in VectorDesigner. In the window, the Clone ID, Sequence, and Collection for each clone will be displayed in the right-hand pane. In the left-hand folder tree, select the folder or subfolder in which to save the clone sequence(s). Clone sequences can be saved as DNA molecules in the DNA/RNAs main user folder or subfolders. To create a new folder, select the Create a New Folder checkbox and enter the folder name in the field. Select the appropriate option under If Object Already Exists—Rename, Overwrite, or Do Not Import. If you select Rename, and the object name already exists in the database, VectorDesigner will automatically rename the new molecule with a numerical extension (1, 2, 3, etc.). When you have made your selections, click on Import. The Import Results page will confirm the results of the import. Click on Return to Database Browser to go to the Database Browser window. At this point you can navigate to the folder in which you saved the clone(s) and open each clone in a Molecule Viewer window. Clones are imported as linear DNA molecules.

OligoPerfect™ Designer

You can design primers for molecule construction and other applications using tools within VectorDesigner (see Designing Primers), or you can send a target DNA sequence from VectorDesigner to the online Web tool OligoPerfect™ Designer to design and order primers. OligoPerfect™ Designer has its own primer design algorithms and procedures. See the OligoPerfect™ Web page and online Help for detailed information and instructions.

To input a target sequence into OligoPerfect™, in the Molecule Viewer dialog: Select the part of the molecule sequence for which you want to design primers, or make no selection if you want to design primers for the entire molecule sequence. Click on the OligoPerfect button (OligoPerfect) on the main toolbar, or select the command from the Tools menu. The OligoPerfect™ Web site will open, and the sequence you selected will be entered in the Target Sequence field. Your login name and the name of the target sequence will also be automatically entered. The OligoPerfect™ Designer will guide you through the primer design process.

In the primer design results page, you can: Select and order the desired primer designs. Select the desired primer designs and click on Send to VectorDesigner to import the primer sequence(s) back into VectorDesigner. See Importing Primers for more information.

Importing Primers from OligoPerfect™

If you have identified primer designs for your sequence of interest using Invitrogen's OligoPerfect™ Designer, you can click on Send to VectorDesigner in the OligoPerfect™ results page to import the primer sequence into VectorDesigner for analysis.

After you click on Send to VectorDesigner in OligoPerfect™, the Import Primers window will open in VectorDesigner. In the window, the primer name, sequence, and other information from OligoPerfect™ will be displayed in the right-hand pane. In the left-hand folder tree, select the database folder or subfolder in which to save the primer sequence(s). Primers can be saved in the Primers main user folder or subfolders. To create a new folder, select the Create a New Folder checkbox and enter the folder name in the field. Select the appropriate option under If Object Already Exists—Rename, Overwrite, or Do Not Import. If you select Rename, and the object name already exists in the database, VectorDesigner will automatically rename the new molecule with a numerical extension (1, 2, 3, etc.). When you have made your selections, click on Import. The Import Results page will confirm the results of the import. Click on Return to Database Browser to go to the Database Browser window.

At this point you can navigate to the folder in which you saved the primers and open them in the Edit Primer Properties dialog.

Performing a BLAST Search

BLAST (Basic Local Alignment Search Tool) searches compare the similarity of a particular DNA or protein sequence to verified gene and protein sequences in multiple public databases. For detailed information on BLAST search types, settings, parameters, search databases, etc., see the BLAST search information page at NCBI.

Using VectorDesigner, you can automatically perform a BLAST search of NCBI databases for all or part of a nucleotide or protein molecule sequence. In the Molecule Viewer window: Select the part of the sequence that you want to search for, or make no selection if you want to search for the entire molecule sequence. Click on the BLAST Search button (blast) on the main toolbar, or select the command from the Tools menu. The BLAST Search dialog will open. In the dialog, under Sequence Range, select Whole Sequence to search for the whole sequence, or Selection Only to search for a portion of the sequence you have selected. Under Sequence Strand, select Direct to search for the direct strand sequence, or Complementary to search for the complementary strand sequence. Under BLAST Page, select the type of database you want to search. See the NCBI BLAST search page for more information on the different search types. For protein sequences, you can search Proteins or Translations databases. For nucleotide sequences, you can search Translations, Nucleotides, or MegaBLAST databases. When you have made your selections, click on OK. The search window for the selected NCBI database will open, and the sequence will appear pasted in the search field. Select any additional search parameters in this window and perform the search.

Analysis Pane

The Analysis Pane displays graphical plots of a variety of a DNA and protein sequence analyses.

You can display multiple plots at a time in the Analysis Pane. The available analyses depend on the molecule type (DNA/RNA or protein). The Analysis Pane and the Graphics Pane are displayed in the same pane in the Molecule Viewer. The Graphics Pane is displayed by default. To display the Analysis Pane, click on the Analysis Pane button below the Graphics Pane. To return to a view of the Graphics Pane, click on the Graphics Pane button Graph Format The graphs in the Analysis Pane display different physiochemical properties of the sequence. Many of properties are based on parameters like charge that exert effects over distance. Other properties represented in the plot depend on the way adjacent bases/amino acids fold in 3-dimensional space, which is a function of the sequence itself.

The vertical (Y) axis in the graph shows the values of the analysis results; the horizontal (X) axis displays either numerical positions in the sequence or residues. At any point along the sequence, the Y value is derived not just from the specific residue at that point but also from adjacent residues. Each analysis algorithm uses an optimum window of adjacent residues to calculate the value for a point. You can adjust this window size in the Plot Properties dialog (see below).

Plots Setup

Use the Plots Setup dialog to select and arrange the analysis graphs to display in the pane. To open the dialog, click on the Plots Setup button below the Analysis Pane or select the command from the right-click menu. In the Plots Setup dialog, the available analyses are listed in the top window and the selected graphs are listed in the bottom window. Analysis graphs are displayed in panels. You can add one or more analyses to a panel, and display multiple panels in the Analysis Pane.

To add analyses to panels: Click on an analysis name in the Available Analyses window to select it. To select multiple graphics, use Control+Click and Shift+Click key combinations. Click on the Copy Analyses button next to the top window. In the bottom window, click on a panel name in the folder tree or create a new panel by clicking on the Create New Panel button. The panel will be selected in the tree. Click on Paste Analyses to Panel to add the analysis or analyses to the panel. Note that if you paste multiple analyses to the same panel, they will be displayed in the same graph in the Analysis Pane. To remove a panel: Click on the panel in the bottom window. Click on Remove Panel (ELJ). All the analyses in the panel will be removed as well.

To copy an analysis between panels: Select the analysis to copy in the bottom window. Click on the Copy Analyses button next to the bottom window. Select the panel you want to copy the analysis to, and click on Paste Analyses to Panel.

To delete an analysis from a panel: Click on the analysis to select it. Click on Remove Analysis. To reorder panels in the Analysis Pane: Click on a panel in the bottom window. Use the arrow buttons next to the bottom window to reorder the panels. When you have arranged the analyses and panels in the dialog, click on OK to display them in the Analysis Pane.

Displaying Analyses in the Analysis Pane

The Analysis Pane window includes various viewing tools: To select a region of the sequence in both the Analysis Pane and the Sequence Pane, drag your cursor over the sequence in either pane. Double-click on a feature in the Text Pane to select that region of the sequence in the Analysis Pane. To zoom in on the graphs, click on the Zoom In button. To zoom out, click on the Zoom Out button. To magnify a region of the graphs, drag your cursor to select the region, then click on the Zoom Selection to Window button. To fit the graphs lengthwise to the current window, click on Fit to Window button. To fit the graphs vertically to the current window, right-click in the pane and select Fit to Size. To make the panels all the same size within the window, right-click in the pane and select Distribute Panels. To hide or show the axes in the graphs, click on the Hide/Show Axes button. To change the display of each plot in the Analysis Pane, see Plot Properties, below.

Plot Properties

The Plot Properties dialog controls how each plot is displayed in the graph. To open the dialog, right-click on an graph in the Analysis Pane and select Plot Properties. The dialog is divided into three tabs. When you have made your selections, click on OK.

Diagram Tab: Click on the Graph Color button to open a dialog in which you can select a plot color and/or adjust the Red-Green-Blue (RGB) values of the color. Select the Draw Type from the dropdown list. Min-Max-Average displays the calculated minimum, maximum, and average values over each analysis region within the sequence as levels of shading along the line of the graph. Under Preprocess Type, select Linear Interpolation to provide a linear interpolation of the graph line, or No Preprocessing to display the line without interpolation.

Params Tab: Window Size is the size of the processing "window" used to scan the sequence for analysis. Enter a number of bases/amino acids in the Window Size field (see example below). Step Size is the number of bases/amino acids in a sequence that constitute an analysis point in the plot. Enter number of bases/amino acids in the Step Size field. For example, if you select a % GC Content analysis with a window size of 21 and a step size of 1, the GC content percentage will be calculated for a 21-base region centered on each base in the sequence (10 bases on either side of the base). A step size of 5 would calculate the percentage for a 21-base region centered on each 5-base region in the sequence.

The Info tab provides information on the type of analysis in the plot, including any references to external literature. Links to Resources and Ordering: Links to Additional Resources VectorDesigher includes built-in links to Web tools, Web sites, download pages, and product ordering pages.
Links to Web Tools and Software Downloads From the Software>Desktop Products menu, select: Information on Desktop Software to link to a Web page with information on Invitrogen's suite of bioinformatics software, including Vector NTI Advance™ for molecule construction, analysis, and databasing; Vector Xpression™ for microarray analysis and databasing; and Vector Path-Blazer™ for biological pathways analysis. Download Vector NTI Advance for PC to link to a download page for Vector NTI Advance™ for the Microsoft Windows® operating system. Download Vector NTI Suite for Mac OS X to link to a download page for Vector NTI Suite™ for the Macintosh® OS X operating system. Download Vector Xpression 3.0 to link to a download page for Vector Xpression™ 3.0 software for Microsoft Windows®. Download Vector Path-Blazer to link to a download page for Vector PathBlazer™ software for Microsoft Windows®.

From the Software>Web Tools menu, select: RNAi Designer to design custom RNAi molecules, including Stealth™ RNAi oligos, for gene knockdown experiments; Peptide Designer to design custom peptides from a protein target sequence; LUX Designer to design custom LUX™ Primer sets from a DNA target sequence for real-time quantitative PCR and RT-PCR applications. Additional Web tools are listed under the Tools menu and include the following: BLAST Search; OligoPerfect Designer; ClonEranger.

Links to Molecule Information

Certain types of imported molecules and example molecules from Invitrogen include links to additional information: Text Pane: The Links folder in the Text Page of the Molecule Viewer provides a list of links to additional online resources for the molecule. The Feature Map folder may also contain Links folders in the individual Feature folders with links to information about each feature. The Imported Features Not Shown on Map folder may also contains Links folders for individual features. Double-click on a link to open it. Feature List: Right-click on a feature in the list and select Open Link to access a list of links to online databases with information about the feature. Select a link from the list to open it. A link can launch a new browser window or an email application. Note that you cannot create new links using VectorDesigner.

Links to Invitrogen Products: You can order primers, vectors, restriction enzymes, and related products from Invitrogen using links in VectorDesigner.

For example, the user can order primer designs from the Molecule Viewer, or you can order saved primers from the Database Browser. If you have primer designs in the Molecule Viewer, go to the PCR Primers folder in the Text Pane, open the Product folder containing the designs, and click on the Order from Invitrogen link next to each primer name. You will be prompted to use the existing primer name or enter a new one (this will not change the primer name in the Molecule Viewer), and the primer sequence will automatically be loaded into Invitrogen's ordering system. You can specify the details of your order (purity, synthesis scale, etc.) on the Web site.

If you have saved primers in the VectorDesigner database, go to the Primers folder in the Database Browser, select the checkbox next to each primer that you want to order, and click on the Order button. Each primer sequence will automatically be loaded into Invitrogen's online ordering system. You can specify the details of each primer order (purity, synthesis scale, etc.) on the Web site.
Vectors You can order Invitrogen vectors and related products from VectorDesigner. VectorDesigner also provides ordering links for molecules constructed from Invitrogen vectors. In the Database Browser, an Add to Cart button will be available in the Order column for each Invitrogen vector or vector constructed from an Invitrogen vector. Click on the button to open an Invitrogen catalog page with information about products related to the vector. In the Molecule Viewer, an Invitrogen Products link will be available in the Text Pane for each Invitrogen vector or vector constructed from an Invitrogen vector. Click on the link to open an Invitrogen catalog page with information about products related to the vector.

Restriction Enzymes Restriction enzymes sold by Invitrogen will be flagged by a symbol in the Restriction Map folder of the Text Pane. Click on the Order from Invitrogen link next to the enzyme name to open an Invitrogen catalog page with information about that enzyme.
Registration The user may be prompted to fill out the information in the Registration form and create a User Name and Password to use VectorDesigner. The User Name and Password will give you secure access to all the molecules in the VectorDesigner database. The molecules in your private user folders will only be accessible using your User Name and Password.
Browser and Operating System Requirements VectorDesigner is supported on various operating systems, Internet browsers, and Java systems: Java Applet and Security Warning VectorDesigner uses a Java applet to display viewers and dialog boxes. In order for the Java applet to run, it may require access to files and other resources on your computer. Depending on the permissions settings for your computer or your network system, you may receive a Security Warning when the Java applet initializes.
Security All molecule sequences, user information, and other data are encrypted during transmission and transmitted via a secure socket layer (SSL). They are stored in encrypted form on our secure servers behind multi-tiered firewalls. Sequences in the private user folders are accessible only if you log in with the correct user name and password.

Privacy: For detailed information about Invitrogen's privacy policy, click on the Privacy Policy link at the bottom of any page in the VectorDesigner.
Dialog Boxes and Notes Add/Edit Feature Use this dialog to define the various features in a molecule, including promoter regions, open reading frames, binding sites, epitopes, or any other region of interest. In the dialog, the Feature Type field lists the available feature types in the database for the molecule. Select a feature type from the list. If you cannot find the precise type you are looking, select Misc. Feature. Note that you cannot add new feature types in VectorDesigner. Enter a name for the feature in the Feature Name field. Select the format to use for defining the sequence region: Use Start.End Format or Use Start . . . Length Format. If you selected or marked the feature region in the sequence before opening the dialog, the start and length/endpoint of the feature will be automatically entered in the dialog. To change the region, enter the start and length/endpoint in the fields. For features with multiple components (i.e., internal start and endpoints), select Multicomponent and enter each start and length/endpoint in the field. Use the following format: <start1> . . . <length/endpoint1>, <start2 . . . length/endpoint2>, etc.

Click on Reset to Selection to undo any changes you may have made to a preselected sequence region. Click on Reset to Mark to undo any changes you may have made to a marked sequence region. Select the Complementary checkbox if the feature is located on the complementary molecule strand. Note: VectorDesigner uses the currently accepted convention for calculating the coordinates of complementary features. All coordinates are given as if on the direct strand, from left to right in the sequence. Enter a description for the feature in the Description field. When you have made your selections, click OK to add the feature.

Annotate Analysis Dialog

Use this dialog to define an open reading frame, restriction fragment, or primer as a feature. In the dialog: Select the feature type from the Feature Type dropdown list; enter the feature name in the Feature Name field; enter a description in the Description field; click on OK. The feature will be added to the feature map. For primers and ORFs, if you want to alter the start and/or endpoint of the sequence before defining it as a feature, right-click on the primer or ORF and select Annotate Analysis Item. This will open the Add/Edit Feature dialog, in which you can change the start/endpoint of the feature.

BLAST Search: Use this dialog to perform a BLAST search of NCBI databases for all or part of a nucleotide or protein molecule sequence. In the dialog: Under Sequence Range, select Whole Sequence to search for the whole sequence, or Selection Only to search for a portion of the sequence you have selected. Under Sequence Strand, select Direct to search for the direct strand sequence, or Complementary to search for the complementary strand sequence. Under BLAST Page, select the type of database you want to search. See the NCBI BLAST search page for more information on the different search types. When you have made your selections, click on OK. The search window for the selected NCBI database will open, and the sequence will appear pasted in the search field. Select any additional search parameters in this window and perform the search.

Browse to Primer Folder

Use this dialog to locate the database folder containing the desired primer sequences. Highlight the folder in the directory tree and click on OK to select the folder. Choose Direct/Complementary Strand Addition Use this dialog box to add any additional nucleotides or specific sequences to the 5' end of the direct or complementary primer. Access this dialog by clicking on the Browse button next to the Direct and/or Complementary fields in the PCR Analysis dialog. In the dialog, you can select from any or all of the following options: Type the nucleotides you want to add directly into the field. Double-click on one or more defined sequences in the table below the field. If you double-click on more than one defined sequence, the defined sequences will be added to the field above 5' to 3' in the order in which you select them. You can then edit the complete sequence in the field. To add a restriction endonuclease cut site at the 5' end of the sequence addition, select the Add One REN Site 5' to the Additions Above checkbox, and select the restriction enzyme from the list below. Depending on the length of the cut site sequence, a pop-up box may prompt you to add nucleotides to the site to improve efficiency of the REN cleavage. Note that you can only add a single restriction site to the 5' end of the primer using this method. When you have made your selections, click on OK. The sequence additions will be displayed in the PCR Analysis dialog.

Create New Folder: Use this dialog to create new subfolders within the three main user folders in the database. Enter the new folder name in the Name field and a folder description in the Description field. Click on Save to create the folder.

Molecule: Use this dialog to create a new molecule based on the molecule currently displayed in the Molecule Viewer. You can create a new molecule from a selected area of the existing molecule, such as a restriction fragment, or from the whole molecule. From DNA or RNA molecules, you can create DNA/RNA molecules that are the reverse complement of the existing molecule or you can create protein molecules from a translation of the sequence.

In the dialog: Enter a name for the new molecule in the Name field, and a description (if any) in the Description field. Next, specify which part of the existing molecule to use as the basis for the new molecule. If you selected or marked a region of the existing molecule before you opened the dialog, the Selection or Mark options will be available and selected. Otherwise, select Molecule to select the whole molecule or Specified Range to enter the sequence range in the From and To fields. DNA/RNA molecules only: Select the Reverse Complement checkbox to create a molecule from the complementary sequence. Select Translate to create a protein molecule from a translation of the sequence. When you have made your selections, click on OK. The new molecule will be created and displayed in a new Molecule Viewer window. The new molecule will not be saved. To add the molecule to the database, you must save it.

Edit Primer Properties

The Edit Primer Properties window displays the sequence, name, and description of each primer that has been saved as a separate molecule in the VectorDesigner database. Note that primer designs generated using the tools in the Molecule Viewer are saved with the DNA molecule file (see Primer Designs and PCR Products for more information). Primers saved as separate primer files are stored in the Primers folder in the VectorDesigner database. To open a primer file, click on the primer name in the Primers folder in the Database Browser. The Edit Primer Properties window includes Name, Description, and Sequence fields. You can edit the text in any of these fields.

To order the primer sequence from Invitrogen, click on the Order button in the window. The primer sequence will automatically be loaded into Invitrogen's online ordering system, where you can specify the details of your order (purity, synthesis scale, etc.). To save any changes you make to the name, description, or sequence, select Rename or Overwrite to specify whether you want to rename the saved file or overwrite the existing file. Then click on the Save button. If you select Rename, the primer will automatically be saved with the existing name plus a numerical extension (1, 2, 3, etc.).

Enzymes List Dialog

The Enzymes List dialog enables you to create a custom list of restriction enzymes to use in restriction mapping. In the dialog, the Customized List lists enzymes that have been selected for use, while the All Enzymes list shows the remaining unselected enzymes in the database. The enzymes are listed alphabetically.

To add or remove enzymes from the Customized List. Click on an enzyme in one of the lists to select it. Use Shift-Click and Control-Click key commands to select multiple enzymes in the list. Click on Add to move the selected enzymes from the All Enzymes list to the Customized List. Click on Remove to remove the selected enzymes from the Customized List. Alternatively, click on Add All to move all the enzymes to the Customized List, or Remove All to remove them from the list. Click on OK to accept your changes. Export to File Dialog Use the Export to File dialog to export the data for the molecule to a file (text format) or to a separate browser window (HTML format): In the dialog, select either Show in Browser or Save Single Object to File. Select the export format (GenBank, FASTA, etc.) and click on OK. If you selected Save Single Object as File, you will be prompted to save the file or open it in a application window. The data will be exported as an ASCII text file. If you selected Show in Browser, the exported file will be displayed in HTML format a separate browser window.
Export to GIF Dialog Use the Export to GIF dialog to export the molecule image as it is displayed in the Molecule Viewer as a GIF image. Note: This command will export only the current view of the molecule. If the displayed information (sequence, graphics, text, etc.) is cut off at the margins of the panes in the Molecule Viewer, the data will appear cut off in the resulting image. Be sure to configure your Molecule Viewer panes as desired-for the resulting image. With your molecule displayed in the Viewer, go to the Molecule menu and select Export to GIF. In the Export to GIF dialog, select Whole Viewer to export an image of the entire Molecule Viewer window, or select the specific pane that you want to export. Select Draw Border to include a border line around the image. If you are exporting the Graphics Pane only, select Graphics Only if you do not want to include the toolbar at the bottom of the pane. When you click on OK, you will be prompted to save the GIF file or open it in an application window.
Map is Updated If you make changes to a molecule sequence in the Molecule Viewer, and those changes affect defined features in the molecule, the Feature Map is Updated dialog will open. In this dialog you can remove any or all of the defined features that will be changed. Note that this will not alter the change that you are making to the sequence; it will only remove the defined feature(s) affected by the change.

In the dialog, the affected features are listed. Select a feature in the list and click on Delete to flag it for deletion. To delete all the features in the list, click on Delete All. If you change your mind, select the feature flagged for deletion and click on Keep, or click on Keep All to keep all features. Click on OK to make the sequence change. If you flagged a feature for deletion in the dialog, that feature will be removed.

Find Sequence: Use this dialog to find a sequence within a larger sequence. In the dialog, type or paste the sequence you want to find, specify the search direction (Up or Down), and click on Find Next. Click on Find Next again to find the next occurrence of the sequence within the larger sequence. Click on Close to close the dialog.
Frequently Used Enzymes AccI, AM, ApaI, AvaI, BamHI, BglII, ClaI, Ddel, Dpnl, Dral, EcoRI, EcoRV, HaeIII, Hhal, Hindi, HindIII, Hinfl, Hpal, Hpall, KpnI, Mbol, Mlul, MscI, Msel, NcoI, NdeI, NheI, NotI, Nml, NsiI, PinAI, PstI, Pvul, PvuII, Rsal, Sail, Seal, SmaI, SpeI, SphI, Sspl, SstI, Sstll, StuI, TaqI, XbaI, XhoI
Gateway® Cloning PCR Products In the PCR Analysis: Gateway Cloning dialog, VectorDesigner will add attB extensions to the direct and complementary primers to generate the af/B-PCR product required for BP recombination into a Gateway® entry clone. Note that which extensions are added to the direct and complementary primers will depend on your Cloning Strand selection. Consult the Gateway® Technology manual for more information about designing primers for Gateway® cloning.

Gateway® cloning will automatically add a 5' sequence to the forward primer consisting of four guanine (G) residues at the 5' end followed by a 25-bp attB1 site. It will also add a 5' sequence to the reverse primer consisting of four G residues at the 5' end followed by a 25-bp attB2 site. See Important Note About Reading Frames for details on preserving the reading frame in af/B-PCR products. TABLE-US-00001 (SEQ ID NO:10) attB1 Forward primer: 5'-GGGG-ACA-AGT-TTG-TAC-AAA-AAA-GCA-GGC-T—(template-specific sequence)-3' (SEQ ID NO:11) atiBl Reverse primer: 5'-GGGG-AC-CAC-TTT-GTA-CAA-GAA-AGC-TGG-GT—(template-specific sequence)-3'
Note About Reading Frames For cloning applications, if you want to fuse your PCR product in frame with an N- or C-terminal peptide tag in the vector, you may need to add bases to the PCR primers to maintain a continuous reading frame between the tag and the insert. To add bases to the primers, use the Choose Direct/Complementary Strand Addition dialog box.

Gateway Cloning Examples: In Gateway® cloning, to fuse your a<<B-PCR product in frame with an N-terminal tag, you must add 2 bases immediately after the attB1 addition (i.e., at the 3' end of the addition). These two nucleotides cannot be AA, AG, or GA, because these additions will create a translation termination codon. To fuse your attB-PCR product in frame with an C-terminal tag, you must add 1 base immediately after the attB2 addition (i.e., at the 3' end of the addition), and you must eliminate any stop codons between the a//B2 site and your gene of interest. If you do not want to fuse the PCR product in frame with a C-terminal tag, your gene of interest or the primer must contain a stop codon. To add a stop codon to the primer, use the Choose Direct/Complementary Strand Addition dialog box.
Insert Sequence Use this dialog to insert a new sequence into an existing sequence in the Molecule Viewer. First, be careful to click at the point in the existing sequence where you want to insert the new sequence. In the dialog, note the insertion point listed below the field. Type or paste the new sequence into the dialog and click on OK. Note: Use only standard code letters when entering the sequence. Nonstandard characters will be marked with a ? in the Insert Sequence dialog and you will be prompted to remove them before adding the new sequence. If you are adding the sequence within a defined feature, the Feature Map is Updated dialog will open, listing the features in the molecule that will be affected by the insertion. In this dialog you can remove any or all of the defined features that will be changed. Note that this will not alter the change that you are making to the sequence; it will only remove the defined feature(s) affected by the change. Click on OK to make the changes.

MegaBLAST uses a "gTeedy algorithm" (Webb Miller et al., J Comput Biol February-April; 2000 7(1-2):203-14) for nucleotide sequence alignment searches and concatenates many queries to save time scanning the database. It is optimized for aligning sequences that differ slightly and is up to 10 times faster than more common sequence similarity programs. It can be used to quickly compare two large sets of sequences against each other. MegaBLAST permits searching with batches of ESTs or with large cDNA or genomic sequences.

Molecule Construction PCR Products

In the PCR Analysis: Molecule Construction dialog, under Cloning Termini, if you select: Blunt: No extensions or overhangs will be automatically added; TA: 3' A extensions will be automatically added to both ends of the PCR product, for TA cloning into an appropriate linearized expression vector with T overhangs. Note that no extensions will be added to the primers. Rather, VectorDesigner will account for the nontemplate-dependent terminal transferase activity of Taq DNA polymerase that adds a single deoxyadenosine (A) to the ends of the PCR products.

ORF Search

Use this dialog to identify open reading frames (ORFs) in a DNA molecule. Using the tool, you set the minimum ORF size, the start and stop codons to search for, and other parameters, and VectorDesigner will generate a list of defined ORFs and highlight them in the sequence. In the ORF Search dialog: Specify the Minimum ORF Size (in codons) and select the Nested ORFs checkbox if you want to search for nested ORFS(ORFs that have the same stop codon but different start codons). In Start Codons and Stop Codons fields, enter one or more start and stop codons to search for when identifying ORFs. Separate each codon by a space. To reset the fields, click on Reset to Default. Select Include Stop Codon in ORF if you want the stop codon to be considered part of the ORF. Otherwise, the stop codon will not be included in each ORF defined in the sequence. Click on OK to search for the ORFs. The ORFs will be marked on the sequence in the Graphics Pane and a folder called Open Reading Frames will be created in the Text Pane.

PCR Analysis: Use this dialog to design PCR primers from a target sequence for cloning applications (including TOPO® Cloning and Gateway® Cloning) or PCR analysis of a DNA molecule fragment.

In the dialog, the default values and available options will different slightly depending on the application you selected (these differences are noted below). Under the Primer Definition and Construction tab, the From and To fields define the region that will be analyzed for primer designs. You can change the numbers in these fields.

Next, enter the primer design parameters, or select the folders containing the saved primers that you want to evaluate for compatibility with the molecule sequence. The following fields are only available if you selected Design Primers to Amplify Selection when you opened the dialog: To include primer design regions before and after the target sequence, enter a number of bases in the Before and After fields. Maximum # of Outputs: Enter the maximum number of primer pair designs to generate. Note that VectorDesigner may generate fewer designs if no more can be found. Tm: Enter the limits in degrees Celsius for primer melting temperature (Tm) (temperature at which 50% of primer is a duplex) in the Minimum and Maximum fields. Designs with Tin's outside this range will be excluded. % GC: Enter the maximum and minimum percent GC content for the primers in the fields. Designs with a percent GC content outside this range will be excluded. Length: Enter the maximum and minimum length (in bases) of each primer in the fields. Designs that fall outside this range will be excluded. Nucleotide sequences such as RENs attached to a primer's 5' end are included when calculating primer length. Exclude Primers with Ambiguous Nucleotides If your sequence includes ambiguous bases (i.e., code letters other than A,G,C,T), select this checkbox to exclude regions containing these bases from the primer design search.

The following fields are only available if you selected Find Amplicon in Sequence Using Existing Primers when you opened the dialog: Click on the Direct button to select the folder containing the direct primers that you want to evaluate, and click on Complementary to select the complementary primers to evaluate. The Browse to Primer Folder dialog will open when you click on each button. Select the folder and click on OK. Enter a percentage similarity in the Similarity>=Threshold field. Each primer sequence must be at least this similar to the molecule sequence to be selected by the designer. Select the checkbox next to LastNucleotides Must Have 100% Similarity to specify a number of nucleotides at the 3' end of each primer that must be 100% similar to the target sequence. Enter a number of nucleotides in the field.

Next, select the conditions of the PCR reaction you are performing. If you are unsure of these values, use the default values: Salt conc: The salt concentration of the PCR reaction, in mMol. If you are unsure, use the default value of 50.0. Probe conc: The final concentration of each primer in the reaction, in pMol. If you are unsure, use the default value of 250.0. dG temp: The temperature of the free energy value of the reaction, in degrees Celsius. If you are unsure, use the default value of 25.0.

Under Cloning Termi, select the type of PCR product you are generating. The available options will vary depending on your cloning application. Click on an application below for more information on how the primer and/or PCR product will be modified based on your selection: e.g., TOPO® Cloning PCR Products; Gateway® Cloning PCR Products; Molecule Construction PCR Products.

For cloning applications, under Cloning strand, select the strand whose sequence will be expressed: Direct or Complementary. Note that this will affect the primer strand to which Directional TOPO®, Gateway®, and other primer additions are added.

Next, select additions to each primer. Click on the Browse button next to the Direct and/or Complementary fields. The Choose Direct/Complementary Strand Addition dialog will open. Select the strand additions in the dialog and click on OK. The additions will be listed in the appropriate field. Additions to the primer sequence will not be used in calculations of primer Tm, % GC, etc. If you change the Cloning Strand (step above) after selecting the primer additions, the additions will switch to the other strand.

Click on the Pairing, Structure and Uniqueness tab to access additional primer specifications. Max. Tm Difference: Specify the maximum difference in melting temperature between sense and antisense primers in degrees Celsius. Note the differences in GC content between the two primer regions of the sequence when specifying this difference; a difference that is too small may result in no primers being found. Max. % GC Difference: Specify the maximum percentage difference in GC content between sense and antisense primers. Note the differences in GC content between the two primer regions of the sequence when specifying this difference; a difference that is too small may result in no primers being found. Primer-Primer Complementarity: Permitted with dG>=: Select this checkbox and enter the minimum permitted value for free energy of a primer-primer duplex. Primer pairs which have a free energy value>/=to this number will be accepted. Primer-Primer Complementarity: 3' End Permitted with dG>=_____: Select this checkbox and enter the minimum permitted value for free energy of complementarity between the 3'-end of the primers (the final 5 bases of each primer will be evaluated). Primer pairs which have a 3'-end complementarity free energy value>/=to this number will be accepted. Exclude Primers With: In the Repeat field, enter the maximum number of base-pair repeats allowed in each primer. In the Palindrome field, enter the maximum permitted length of palindromes in each primer sequence. In the Hairpin Loops field, enter the minimum permitted value for free energy of hairpin loops within each primer. Primer Uniqueness: Select this checkbox to reject primers above a certain percentage similarity to secondary sites within either the entire sequence or within the amplicon. Enter an percentage similarity in the field, and select Within Entire Sequence or Within Amplicon Only.

Click on OK to design the primers. You will be prompted to send the PCR product for the first (highest ranked) primer pair directly to the appropriate molecule construction workspace as an insert. If you click on No, all the primer pairs generated will be added to the PCR Primers folder in the Text Pane of the Molecule Viewer.

Plot Properties

The Plot Properties dialog controls how each plot is displayed in the Analysis Pane. The dialog is divided into three tabs. When you have made your selections, click on OK. Diagram Tab. Click on the Graph Color button (mm) to open a dialog in which you can select a plot color and/or adjust the Red-Green-Blue (RGB) values of the color. Select the Draw Type from the dropdown list. Min-Max-Average displays the calculated minimum, maximum, and average values over each analysis region within the sequence as levels of shading along the line of the graph. Under Preprocess Type, select Linear Interpolation to provide a linear interpolation of the graph line, or No Preprocessing to display the line without interpolation.

Params Tab

Window Size is the size of the processing "window" used to scan the sequence for analysis. Enter a number of bases/amino acids in the Window Size field (see example below). Step Size is the number of bases/amino acids in a sequence that constitute an analysis point in the plot. Enter number of bases/amino acids in the Step Size field (see example below).

For example, if you select a % GC Content analysis with a window size of 21 and a step size of 1, the GC content percentage will be calculated for a 21-base region centered on each base in the sequence (10 bases on either side of the base). A step size of 5 would calculate the percentage for a 21-base region centered on each 5-base region in the sequence.

The Info tab provides information on the type of analysis in the plot, including any references to external literature.

Plots Setup: Use the Plots Setup dialog to select and arrange the analysis graphs to display in the Analysis Pane. In the Plots Setup dialog, the available analyses are listed in the top window and the selected graphs are listed in the bottom window. Analysis graphs are displayed in panels. You can add one or more analyses to a panel, and display multiple panels in the Analysis Pane.

To add analyses to panels: Click on an analysis name in the Available Analyses window to select it. To select multiple graphics, use Control+Click and Shift+Click key combinations. Click on the Copy Analyses button next to the top window. In the bottom window, click on a panel name in the folder tree or create a new panel by clicking on the Create New Panel button. The panel will be selected in the tree. Click on Paste Analyses to Panel to add the analysis or analyses to the panel. Note that if you paste multiple analyses to the same panel, they will be displayed in the same graph in the Analysis Pane.

To remove a panel: Click on the panel in the bottom window. Click on Remove Panel. All the analyses in the panel will be removed as well.

To copy an analysis between panels: Select the analysis to copy in the bottom window. Click on the Copy Analyses button next to the bottom window. Select the panel you want to copy the analysis to, and click on Paste Analyses to Panel B To delete an analysis from a panel: Click on the analysis to select it. Click on Remove Analysis.

To reorder panels in the Analysis Pane: Click on a panel in the bottom window. Use the arrow buttons next to the bottom window to reorder the panels. When you have arranged the analyses and panels in the dialog, click on OK to display them in the Analysis Pane.

Restriction Map Search: Use this dialog to identify the restriction enzyme cut sites in a DNA molecule using a built-in database of restriction enzymes. In the dialog: Select the category of enzymes that you want to use from the Use Enzymes list: Frequently Used Enzymes have been identified by Invitrogen. Click here for a list. 7+ Cutters, 6 Cutters, 5 Cutters, etc. refer to the number of base pairs in the recognition site of each enzyme. Enzymes in the 5' Overhang category result in fragments with a 5' overhang; enzymes in the 3' Overhang category result in fragments with a 3' overhang. If you select Customized, click on the Customize button to select the particular enzymes you want to use. The Enzymes List dialog will open. Next, enter a number in the Display Enzymes with <=Recognition Sites field. The Designer will analyze the sequence and use only those enzymes with less than or equal to that number of cut sites. Alternatively, select Unlimited to not filter the enzyme list by number of cut sites. 4. When you have made your selections, click on OK.

Save As

In the Save As dialog: Click in the folder tree to select the folder or subfolder where you want to save the molecule. Note that the molecule type determines which main user folder you can save it in (e.g., DNA/RNA molecules can only be saved in the DNA/RNAs folder or subfolders; primers can only be saved in the Primers folder or subfolders). To create a new subfolder within the main folder, click on Create New Folder and enter the information in the Create New Folder dialog. Enter a name for the molecule and click on OK to save it to the database. The new molecule will be listed in the Database Browser.

Sequence Properties

Use this dialog to change how the sequence is displayed in the pane. The dialog contains following display options:

Sequence Representation Styles

Multiline Fixed: Display a fixed number bases/amino acids per line on multiple lines, regardless of window size. (Dependent on Symbols in Group and Groups in Line settings.). Multiline Variable: Display a variable number of bases/amino acids per line on multiple lines, depending on window size. Single Line: Display a single line of bases/amino acids, regardless of window size. Show Direct Strand Only: DNA molecules only—Select this checkbox to show only the direct DNA strand in the pane. Symbols in Group: Enter the number of bases/amino acids to display in a group for ease of reading; dependent on Insert Gaps Between Groups to view the groups in the display. Groups in Line: Enter the number of groups to display on a line if the Multiline Fixed setting is selected. Insert Gaps Between Groups: Select this checkbox to insert a space between groups in the sequence.

Feature Representation Style

Show Direct Features: For protein molecules, select this checkbox to mark defined features in the sequence with colored bars above the sequence. For DNA molecules, this marks defined features on the direct strand with colored bars above the sequence. Show Complementary Features: For DNA molecules only, select this checkbox to mark defined features on the complementary strand with colored bars below the sequence. Feature Height: Enter a relative height scale (1-5) for feature bars as displayed in the Sequence Pane.

Selection

Use this dialog to select part of the sequence defined by the start and end bases/amino acids. Enter the number of the starting base/amino acid in the Start field and the ending base/amino acid in the End field and click on OK. The defined area will appear selected in the Graphics and Sequence Panes.

TOPO® Cloning PCR Products

In the PCR Analysis: TOPO Cloning dialog, under Cloning Termini, if you Blunt: No extensions or overhangs will be automatically added. PCR products generated using these primers are suitable for Zero Blunt® TOPO® PCR Cloning; TA: 3' A overhangs will be added to both ends of the resulting PCR product. These PCR products are suitable for TOPO® TA Cloning. Note that no extensions will be added to the primers themselves. Rather, VectorDesigner will account for the nontemplate-dependent terminal transferase activity of Taq DNA polymerase that adds a single deoxyadenosine (A) to the ends of the PCR products. If the user selects Directional, a CACC sequence will be added to the 5' end of the direct or complementary strand primer, depending on your Cloning Strand selection. PCR products generated using these primers are suitable for Directional TOPO® Cloning.

Types Filter: Use this dialog to filter the types of features highlighted in the Sequence Pane. In the dialog, deselect the checkboxes next to the filters that you do not want to view in the Sequence Pane, and click on OK to make the changes.

Various embodiments of the present invention have been described above. It should be understood that these embodiments have been presented by way of example only, and not limitation. It will be understood by those skilled in the relevant art that various changes in form and detail of the embodiments described above may be made without departing from the spirit and scope of the present invention as defined in the claims. Thus, the breadth and scope of the present invention should not be limited by any of the above-described exemplary embodiments, but should be defined only in accordance with the following claims and their equivalents.

The invention claimed is:

1. A non-transitory computer-readable storage medium encoded with instructions, executable by a processor, the instructions comprising instructions for in silico design of a method to produce one or more biomolecules comprising:

presenting to a user a plurality of subroutines for laboratory implementation that comprise the biological workflow listed in a sequential order, wherein at least two subroutines of the plurality of subroutines comprise two steps;

providing the user ability to navigate to any subroutine of the plurality of sequential subroutines, to select a subroutine and view, set, or change one or more parameters associated with a step of the selected subroutine;

providing an option to display to the user, one or more biomolecules resulting from execution of one or more of the plurality of subroutines for laboratory implementation wherein each such subroutine generates at least one biomolecule used by the next subroutine to generate another biomolecule;

providing an option to the user to navigate to a prior subroutine and change a parameter of a step of the prior subroutine, if the user is not satisfied with the one or more displayed biomolecules;

providing the user the ability to access a company database with product information that the user may use to produce the one or more biomolecules;

receiving selections by the user of one or more parameters for each step of the plurality of subroutines of the biological workflow and saving the selections as a selected plurality of steps, wherein the saved selected plurality of steps comprise the user-defined method;

storing a user defined name for the user-defined method; and presenting to the user a method for laboratory implementation to produce one or more biomolecules.

2. A non-transitory computer-readable storage medium of claim 1, the method further comprising:
providing an indication to the user of a current subroutine of the method for performing a biological workflow for the user to review.

3. A non-transitory computer-readable storage medium of claim 1, the method further comprising:
providing to the user the ability to rate or comment on the user defined workflow and storing the rating associated with the user defined workflow in the memory.

4. A non-transitory computer-readable storage medium of claim 3, the method further comprising:
providing to the user, preset settings for parameters based on user defined workflows with the highest ratings or the most positive comments.

5. A non-transitory computer-readable storage medium of claim 1, wherein the parameter being viewed, set or changed is a parameter that results from ambiguous user data.

6. A non-transitory computer-readable storage medium of claim 1, wherein every parameter in a workflow that is set based on ambiguous user data can be viewed, set, or changed by the user.

7. A non-transitory computer-readable storage medium of claim 1, the method further comprising:
providing the user the ability to navigate to any subroutine of the plurality of sequential subroutines to select a subroutine and view, set, or change one or more parameters associated with a step of the selected subroutine, wherein every parameter in a workflow that is set based on ambiguous user data is highlighted to a user such that the parameter can be viewed, set, or changed by the user.

8. The non-transitory computer-readable storage medium of claim 1, wherein the instructions further comprise instructions for:
providing to the user the ability to save a log of all selected parameters for each step of the user defined method; and
receiving and storing from the user at least one comment about the user defined method.

9. The non-transitory computer-readable storage medium of claim 1, wherein the instructions further comprise instructions for:
storing one or more external files uploaded by the user; and
providing to the user or to additional users ability to view the one or more external files uploaded.

10. The non-transitory computer-readable storage medium of claim 1, wherein viewing, selecting, setting, or changing one or more parameters associated with a step of the selected subroutine by the user comprises using a graphical user interface (GUI).

11. The non-transitory computer-readable storage medium encoded with instructions, executable by a processor, of claim 1, wherein the one or more parameters viewed, selected, set or changed by the user are from one or more default parameters, wherein default parameters are pre-determined parameters stored in the computer-readable storage medium.

12. The non-transitory computer-readable storage medium encoded with instructions, executable by a processor, of claim 1, wherein the one or more parameters viewed, selected, set or changed by the user comprise at least one user input parameter.

13. The non-transitory computer-readable storage medium encoded with instructions, executable by a processor, of claim 12, wherein the user input parameter is a modified default parameter, a parameter input by user, or a parameter imported by the user into the computer system, wherein a default parameter is a pre-determined parameter stored in a component of the computer-readable storage medium.

14. The non-transitory computer-readable storage medium encoded with instructions, executable by a processor, of claim 1, wherein the one or more parameters viewed, selected, set or changed by the user comprise a combination of one or more default parameters and one or more user defined parameters, wherein default parameters are pre-determined parameters stored in a component of the computer-readable storage medium and wherein the user input parameter is a modified default parameter, a parameter input by user, or a parameter imported by the user into the computer system.

15. The non-transitory computer-readable storage medium encoded with instructions, executable by a processor of claim 14, further comprising:
executing the user defined workflow comprising executing in silico all the steps of the user defined workflow in sequential order;
viewing a first biomolecule obtained by executing the user defined workflow in silico;
generation of at least a second user defined workflow, comprising changing the selection of at least one parameter to have a different value relative to the same parameter that was selected in claim 1;
executing in silico the at least second user defined workflow to obtain a second biomolecule;
viewing the second biotechnology product in silico; and
comparing the first biomolecule with the second biomolecule, thereby allowing a user to determine if the first user defined workflow or the second user defined method produces a preferred biomolecule.

16. The non-transitory computer-readable storage medium encoded with instructions, executable by a processor, of claim 1, wherein providing the user ability to navigate to any subroutine of the plurality of subroutines is by a graphical user interface (GUI) which comprises displaying on a first display screen pane all the subroutines of a sequential subroutine comprising the biological workflow and, following selection by the user of any one subroutine, displaying on a second display screen, one or more steps associated with the selected subroutine.

17. The non-transitory computer-readable storage medium encoded with instructions, executable by a processor, of claim 1, wherein providing the user the ability to navigate to any step of a subroutine is accomplished by a graphical user interface (GUI) which comprises displaying on a first display screen pane the subroutine and displaying on a second display screen, one or more steps associated with the selected subroutine.

18. The non-transitory computer-readable storage medium encoded with instructions, executable by a processor, of claim 1, wherein providing to the user an option for saving on the computer readable storage medium a user defined method comprising at least one selection desired by the user comprises:
a) displaying on a display screen pane a prescribed plurality of subroutines in a sequential order of the biological workflow, wherein the prescribed plurality of subroutines are comprised in a computer readable format;

b) navigation by a user using a graphical user interface (GUI) on the display screen of each subroutine of the prescribed plurality of subroutines of the biological workflow;

c) selection by the user of one of the subroutines;

d) navigation by a user using a GUI on the display screen of each step of a selected subroutine;

e) selection by the user of one or more parameters in each step of a selected subroutine to obtain a modified plurality of steps;

f) storing the modified plurality of steps by the user, wherein the stored modified plurality of steps comprise the user defined subroutine g) repeating steps b)-f) till all the plurality of sub routines are stored as user defined subroutines; and h) saving and executing the plurality of user defined subroutines to perform a user defined biological workflow.

19. The non-transitory computer-readable storage medium encoded with instructions, executable by a processor, of claim 1, wherein the navigation by a user of any subroutine or step of the workflow is in a sequential order of the steps or the subroutine.

20. The non-transitory computer-readable storage medium encoded with instructions, executable by a processor, of claim 1, wherein the navigation by a user of any subroutine or step of the workflow is in a non-sequential order of the steps or the subroutine.

21. A non-transitory computer-readable storage medium encoded with instructions, executable by a processor, of claim 1, wherein the biological workflow comprises a cloning method, a recombination method, a ligation method, a vector designing method, a method for synthesis of a nucleic acid, a primer design method, a method for synthesis of a polypeptide, method for analysis of a cloned molecule, method of protein analysis, method for making a modified host.

22. The non-transitory computer-readable storage medium encoded with instructions, executable by a processor of claim 1, further comprising providing an option to display to the user, one or more biomolecules resulting from reexecution of the subroutines of the workflow.

23. The non-transitory computer-readable storage medium encoded with instructions, executable by a processor of claim 1, further comprising providing the ability to input data from a biological instrument wherein the data is used during execution of a subroutine.

24. A computer-implemented method comprising:

presenting to a user a plurality of subroutines for laboratory implementation that comprise a biological workflow for the in silico design of a method to produce one or more biomolecules, listed in a sequential order, wherein at least two subroutines of the plurality of subroutines comprise two steps;

providing the user ability to navigate to any subroutine of the plurality of sequential subroutines, to select a subroutine and view, set, or change one or more parameters associated with a step of the selected subroutine;

providing an option to display to the user, one or more biomolecules resulting from execution of one or more of the plurality of subroutines for laboratory implementation wherein each such subroutine generates at least one biomolecule used by the next subroutine to generate another biomolecule;

providing an option to the user to navigate to a prior subroutine and change a parameter of a step of the prior subroutine, if the user is not satisfied with the one or more displayed biomolecules;

providing the user the ability to access a company database with product information that the user may use to produce the one or more biomolecules;

receiving selections by the user of one or more parameters for each step of the plurality of subroutines of the biological workflow and saving the selections as a selected plurality of steps, wherein the saved selected plurality of steps comprise the user-defined method; and storing a user defined name for the user-defined method; and presenting to the user a method for laboratory implementation to produce one or more biomolecules.

25. A system comprising:

a processor; and a memory for storing instructions executable by the processor, the instructions comprising instructions for:

presenting to a user a plurality of subroutines for laboratory implementation that comprise a biological workflow for the in silico design of a method to produce one or more biomolecules, listed in a sequential order, wherein at least two subroutines of the plurality of subroutines comprise two steps;

providing the user ability to navigate to any subroutine of the plurality of sequential subroutines, to select a subroutine and view, set, or change one or more parameters associated with a step of the selected subroutine;

providing an option to display to the user, one or more biomolecules resulting from execution of one or more of the plurality of subroutines wherein each such subroutine generates at least one biomolecule used by the next subroutine to generate another biomolecule;

providing an option to the user to navigate to a prior subroutine and change a parameter of a step of the prior subroutine, if the user is not satisfied with the one or more displayed biomolecules;

providing the user the ability to access a company database with product information that the user may use to produce the one or more biomolecules;

receiving selections by the user of one or more parameters for each step of the plurality of subroutines of the biological workflow and saving the selections as a selected plurality of steps, wherein the saved selected plurality of steps comprise the user-defined method;

storing a user defined name for the user-defined method; and presenting to the user a method for laboratory implementation to produce one or more biomolecules.

* * * * *